United States Patent
Mitchell

(10) Patent No.: US 12,245,788 B2
(45) Date of Patent: Mar. 11, 2025

(54) DEVICE AND METHOD FOR REMOVING MATERIAL FROM A HOLLOW ANATOMICAL STRUCTURE

(71) Applicant: AngioDynamics, Inc., Latham, NY (US)

(72) Inventor: James J. Mitchell, Ballston Spa, NY (US)

(73) Assignee: AngioDynamics, Inc., Latham, NY (US)

( * ) Notice: Subject to any disclaimer, the term of this patent is extended or adjusted under 35 U.S.C. 154(b) by 1011 days.

(21) Appl. No.: 17/220,488

(22) Filed: Apr. 1, 2021

(65) Prior Publication Data
US 2021/0220006 A1 Jul. 22, 2021

Related U.S. Application Data

(63) Continuation-in-part of application No. 16/797,188, filed on Feb. 21, 2020, now Pat. No. 11,464,537.
(Continued)

(51) Int. Cl.
*A61B 17/3207* (2006.01)
*A61B 17/22* (2006.01)
(Continued)

(52) U.S. Cl.
CPC .... *A61B 17/320725* (2013.01); *A61B 17/221* (2013.01); *A61B 17/320758* (2013.01);
(Continued)

(58) Field of Classification Search
CPC .......... A61B 17/221; A61B 17/320725; A61B 17/320758; A61B 2017/22038;
(Continued)

(56) References Cited

U.S. PATENT DOCUMENTS

| 1,050,030 A | 1/1913 | Keenan |
| 3,831,587 A | 8/1974 | Boyd |

(Continued)

FOREIGN PATENT DOCUMENTS

| AU | 2015274704 | 10/2016 |
| AU | 2016341439 | 5/2018 |

(Continued)

OTHER PUBLICATIONS

F.A.S.T. Funnel Catheter Proximal Occlusion Embolectomy/Thrombectomy System, Genesis Medical Interventional, 4 pages. (2008).
(Continued)

*Primary Examiner* — Jocelin C Tanner
(74) *Attorney, Agent, or Firm* — Kevin P. Radigan, Esq.; Heslin Rothenberg Farley & Mesiti P.C.

(57) ABSTRACT

A medical device for removing a material from a hollow anatomical structure is provided. The device may include a shaft member. The device may include an expandable centering element near the distal end of the device. The device may include a macerator element either attached to the shaft or independent and freely moveable from the shaft. The device may include an aspiration lumen in for removal of material. The device may include a drive shaft attached to a motor and used to rotate the macerator element.

20 Claims, 34 Drawing Sheets

Related U.S. Application Data which is a continuation of application No. 14/708,355, filed on May 11, 2015, now Pat. No. 10,568,654, which is a continuation of application No. 13/420,913, filed on Mar. 15, 2012, now Pat. No. 9,055,964.

(60) Provisional application No. 61/585,348, filed on Jan. 11, 2012, provisional application No. 61/521,494, filed on Aug. 9, 2011, provisional application No. 61/452,838, filed on Mar. 15, 2011.

(51) Int. Cl.
*A61B 17/221* (2006.01)
*A61B 90/00* (2016.01)

(52) U.S. Cl.
CPC ............... *A61B 2017/22038* (2013.01); *A61B 2017/22067* (2013.01); *A61B 2017/22068* (2013.01); *A61B 2017/2212* (2013.01); *A61B 2017/2215* (2013.01); *A61B 2017/320716* (2013.01); *A61B 2017/320733* (2013.01); *A61B 2017/320775* (2013.01); *A61B 2090/08021* (2016.02); *A61B 2217/005* (2013.01)

(58) Field of Classification Search
CPC ........... A61B 2017/22067; A61B 2017/22068; A61B 2017/2212; A61B 2017/2215; A61B 2017/320716; A61B 2017/320733; A61B 2017/320775; A61B 2090/0821; A61B 2217/005
See application file for complete search history.

(56) References Cited

U.S. PATENT DOCUMENTS

| | | |
|---|---|---|
| 4,033,345 A | 7/1977 | Sorenson |
| 4,046,150 A | 9/1977 | Schwartz |
| 4,273,128 A | 6/1981 | Lary |
| 4,437,856 A | 3/1984 | Valli |
| 4,445,509 A | 5/1984 | Auth |
| 4,469,100 A | 9/1984 | Hardwick |
| 4,646,736 A | 3/1987 | Auth |
| 4,653,496 A * | 3/1987 | Bundy ............... A61B 17/3207 604/164.11 |
| 4,664,112 A | 5/1987 | Kensey |
| 4,671,796 A | 6/1987 | Groshong |
| 4,681,564 A | 7/1987 | Landreneau |
| 4,693,243 A | 9/1987 | Buras |
| 4,696,667 A | 9/1987 | Masch |
| 4,729,763 A | 3/1988 | Henrie |
| 4,747,821 A | 5/1988 | Kensey |
| 4,749,376 A | 6/1988 | Kensey |
| 4,790,812 A | 12/1988 | Hawkins, Jr. |
| 4,834,743 A | 5/1989 | Valerio |
| 4,857,045 A | 8/1989 | Rydell |
| 4,857,046 A | 8/1989 | Stevens |
| 4,886,061 A | 12/1989 | Fischell |
| 4,886,487 A | 12/1989 | Solem |
| 4,892,529 A | 1/1990 | Valerio |
| 4,895,166 A | 1/1990 | Farr |
| 4,895,560 A | 1/1990 | Papantonakos |
| 4,921,478 A | 5/1990 | Solano |
| 4,990,134 A | 2/1991 | Auth |
| 4,990,151 A | 2/1991 | Wallsten |
| 5,011,488 A | 4/1991 | Ginsburg |
| 5,019,089 A | 5/1991 | Farr |
| 5,030,201 A * | 7/1991 | Palestrant ...... A61B 17/320725 600/568 |
| 5,055,198 A | 10/1991 | Shettigar |
| 5,074,841 A | 12/1991 | Ademovic |
| 5,078,677 A | 1/1992 | Gentelia |
| 5,084,052 A | 1/1992 | Jacobs |
| 5,092,839 A | 3/1992 | Kipperman |
| 5,092,877 A | 3/1992 | Pinchuk |
| 5,098,440 A | 3/1992 | Hillstead |
| 5,100,376 A | 3/1992 | Blake, III |
| 5,100,423 A | 3/1992 | Fearnot |
| 5,102,415 A | 4/1992 | Guenther |
| 5,114,399 A | 5/1992 | Kovalcheck |
| 5,115,816 A | 5/1992 | Lee |
| 5,133,703 A | 7/1992 | Boehringer |
| 5,158,533 A | 10/1992 | Strauss |
| 5,158,564 A | 10/1992 | Schnepp-Pesch |
| 5,188,618 A | 2/1993 | Thomas |
| 5,201,703 A | 4/1993 | Gentelia |
| 5,211,651 A | 5/1993 | Reger |
| 5,226,909 A | 7/1993 | Evans |
| 5,234,403 A | 8/1993 | Yoda |
| 5,242,441 A | 9/1993 | Avitall |
| 5,257,974 A | 11/1993 | Cox |
| 5,273,526 A | 12/1993 | Dance |
| 5,306,250 A | 4/1994 | March |
| 5,334,208 A | 8/1994 | Soehendra |
| 5,380,314 A | 1/1995 | Herweck |
| 5,423,799 A | 6/1995 | Shiu |
| 5,464,408 A | 11/1995 | Duc |
| 5,474,563 A | 12/1995 | Myler |
| 5,490,859 A | 2/1996 | Mische |
| 5,520,697 A | 5/1996 | Lindenberg |
| 5,540,707 A | 7/1996 | Ressemann |
| 5,569,275 A | 10/1996 | Kotula |
| 5,571,086 A | 11/1996 | Kaplan |
| 5,588,958 A | 12/1996 | Cunningham |
| 5,628,746 A | 5/1997 | Clayman |
| 5,632,755 A | 5/1997 | Nordgren |
| 5,643,309 A | 7/1997 | Myler |
| 5,653,684 A | 8/1997 | Laptewicz |
| 5,695,489 A | 12/1997 | Japuntich |
| 5,713,853 A | 2/1998 | Clark |
| 5,722,964 A | 3/1998 | Herweck |
| 5,733,302 A | 3/1998 | Myler |
| 5,772,629 A | 6/1998 | Kaplan |
| 5,776,141 A | 7/1998 | Klein |
| 5,785,700 A | 7/1998 | Olson |
| 5,785,715 A | 7/1998 | Schatz |
| 5,788,661 A | 8/1998 | Japuntich |
| 5,800,457 A | 9/1998 | Gelbfish |
| 5,843,103 A | 12/1998 | Wulfman |
| 5,846,251 A | 12/1998 | Hart |
| 5,868,753 A | 2/1999 | Schatz |
| 5,873,882 A | 2/1999 | Straub |
| 5,908,435 A | 6/1999 | Samuels |
| 5,910,144 A | 6/1999 | Hayashi |
| 5,941,895 A | 8/1999 | Myler |
| 6,001,112 A | 12/1999 | Taylor |
| 6,059,745 A | 5/2000 | Gelbfish |
| 6,083,239 A | 7/2000 | Addis |
| 6,106,531 A | 8/2000 | Schatz |
| 6,135,991 A | 10/2000 | Muni |
| 6,159,220 A | 12/2000 | Gobron |
| 6,159,230 A | 12/2000 | Samuels |
| 6,161,547 A | 12/2000 | Barbut |
| 6,187,016 B1 | 2/2001 | Hedges |
| 6,200,276 B1 | 3/2001 | Biesel |
| 6,203,537 B1 | 3/2001 | Adrian |
| 6,206,868 B1 | 3/2001 | Parodi |
| 6,206,898 B1 | 3/2001 | Honeycutt |
| 6,241,738 B1 | 6/2001 | Dereume |
| 6,274,055 B1 | 8/2001 | Zuk, Jr. |
| 6,280,413 B1 | 8/2001 | Clark |
| 6,280,464 B1 | 8/2001 | Hayashi |
| 6,283,940 B1 | 9/2001 | Mulholland |
| 6,287,321 B1 | 9/2001 | Jang |
| 6,364,896 B1 | 4/2002 | Addis |
| 6,394,978 B1 | 5/2002 | Boyle |
| 6,413,235 B1 | 7/2002 | Parodi |
| 6,423,032 B2 | 7/2002 | Parodi |
| 6,443,966 B1 | 9/2002 | Shiu |
| 6,451,036 B1 | 9/2002 | Heitzmann |
| 6,454,775 B1 * | 9/2002 | Demarais .......... A61M 25/0023 606/128 |

(56) References Cited

U.S. PATENT DOCUMENTS

| | | |
|---|---|---|
| 6,454,779 B1 | 9/2002 | Taylor |
| 6,491,712 B1 | 12/2002 | O'Connor |
| 6,500,191 B2 | 12/2002 | Addis |
| 6,508,782 B1 | 1/2003 | Evans |
| 6,540,712 B1 | 4/2003 | Parodi |
| 6,547,754 B1 | 4/2003 | Evans |
| 6,558,341 B1 | 5/2003 | Swisher |
| 6,569,181 B1 | 5/2003 | Burns |
| 6,582,396 B1 | 6/2003 | Parodi |
| 6,592,606 B2 | 7/2003 | Huter |
| 6,602,264 B1 | 8/2003 | McGuckin, Jr. |
| 6,660,014 B2 | 12/2003 | Demarais |
| 6,666,874 B2 | 12/2003 | Heitzmann |
| 6,673,039 B1 | 1/2004 | Bridges |
| 6,676,692 B2 | 1/2004 | Rabkin |
| 6,679,893 B1 | 1/2004 | Tran |
| 6,682,656 B2 | 1/2004 | Rothman |
| 6,685,722 B1 | 2/2004 | Rosenbluth |
| 6,695,858 B1 | 2/2004 | Dubrul |
| 6,702,830 B1 | 3/2004 | Demarais |
| 6,719,717 B1 | 4/2004 | Johnson |
| 6,749,619 B2 | 6/2004 | Ouriel |
| 6,776,770 B1 | 8/2004 | Trerotola |
| 6,802,846 B2 | 10/2004 | Hauschild |
| 6,808,520 B1 | 10/2004 | Fourkas |
| 6,808,531 B2 | 10/2004 | Lafontaine |
| 6,837,901 B2 | 1/2005 | Rabkin |
| 6,852,280 B2 | 2/2005 | Vijay |
| 6,878,153 B2 | 4/2005 | Linder |
| 6,905,490 B2 | 6/2005 | Parodi |
| 6,908,474 B2 | 6/2005 | Hogendijk |
| 6,936,060 B2 | 8/2005 | Hogendijk |
| 6,939,362 B2 | 9/2005 | Boyle |
| 6,945,977 B2 | 9/2005 | Demarais |
| 6,946,099 B2 | 9/2005 | Vijay |
| 6,960,222 B2 | 11/2005 | Vo |
| 6,962,598 B2 | 11/2005 | Linder |
| 7,014,913 B2 | 3/2006 | Pacetti |
| 7,063,707 B2 | 6/2006 | Bose |
| 7,108,704 B2 | 9/2006 | Trerotola |
| 7,118,585 B2 | 10/2006 | Addis |
| 7,153,292 B2 | 12/2006 | Morris |
| 7,153,320 B2 | 12/2006 | Euteneuer |
| 7,172,610 B2 | 2/2007 | Heitzmann |
| 7,175,660 B2 | 2/2007 | Cartledge |
| 7,220,269 B1 | 5/2007 | Ansel |
| 7,223,253 B2 | 5/2007 | Hogendijk |
| 7,229,402 B2 | 6/2007 | Diaz |
| 7,235,088 B2 | 6/2007 | Pintor |
| 7,258,696 B2 | 8/2007 | Rabkin |
| 7,300,458 B2 | 11/2007 | Henkes |
| 7,309,334 B2 | 12/2007 | Von Hoffmann |
| 7,344,549 B2 | 3/2008 | Boyle |
| 7,351,255 B2 | 4/2008 | Andreas |
| 7,353,956 B2 | 4/2008 | Lynn |
| 7,374,560 B2 | 5/2008 | Ressemann |
| 7,429,325 B2 | 9/2008 | Ingvarsson |
| 7,479,147 B2 | 1/2009 | Honeycutt |
| 7,655,016 B2 | 2/2010 | Demarais |
| 7,674,237 B2 | 3/2010 | O'Mahony |
| 7,678,130 B2 | 3/2010 | Mazzocchi |
| 7,682,563 B2 | 3/2010 | Carpenter |
| 7,713,227 B2 | 5/2010 | Wholey |
| 7,766,934 B2 | 8/2010 | Pal |
| 7,771,445 B2 | 8/2010 | Heitzmann |
| 7,771,452 B2 | 8/2010 | Pal |
| 7,776,062 B2 | 8/2010 | Besselink |
| 7,780,696 B2 | 8/2010 | Daniel |
| 7,794,420 B2 | 9/2010 | Perovitch |
| 7,799,046 B2 | 9/2010 | White |
| 7,842,010 B2 | 11/2010 | Bonnette |
| 7,842,055 B2 | 11/2010 | Pintor |
| 7,862,575 B2 | 1/2011 | Tal |
| 7,879,022 B2 | 2/2011 | Bonnette |
| 7,892,273 B2 | 2/2011 | George |
| 7,896,832 B2 | 3/2011 | Zafirelis |
| 7,912,531 B1 | 3/2011 | Chiu |
| 7,938,820 B2 | 5/2011 | Webster |
| 8,034,095 B2 | 10/2011 | Randolph |
| 8,038,704 B2 | 10/2011 | Sherburne |
| 8,075,510 B2 | 12/2011 | Aklog |
| 8,167,903 B2 | 5/2012 | Hardert |
| 8,182,508 B2 | 5/2012 | Magnuson |
| 8,187,465 B2 | 5/2012 | Nierich |
| 8,216,269 B2 | 7/2012 | Magnuson |
| 8,298,252 B2 | 10/2012 | Krolik |
| 8,317,859 B2 | 11/2012 | Snow |
| 8,361,095 B2 | 1/2013 | Osborne |
| 8,377,092 B2 | 2/2013 | Magnuson |
| 8,469,970 B2 | 6/2013 | Diamant |
| 8,470,016 B2 | 6/2013 | Sherburne |
| 8,475,487 B2 | 7/2013 | Bonnette |
| 8,480,702 B2 | 7/2013 | Kusleika |
| 8,586,324 B2 | 11/2013 | Leach |
| 8,613,717 B2 | 12/2013 | Aklog |
| 8,632,584 B2 | 1/2014 | Henkes |
| 8,734,374 B2 | 5/2014 | Aklog |
| 8,777,976 B2 | 7/2014 | Brady |
| 8,777,977 B2 | 7/2014 | Angel |
| 8,784,434 B2 | 7/2014 | Rosenbluth |
| 8,784,441 B2 | 7/2014 | Rosenbluth |
| 8,828,073 B2 | 9/2014 | Sherburne |
| 8,852,205 B2 | 10/2014 | Brady |
| 8,945,141 B2 | 2/2015 | Cahill |
| 8,945,170 B2 | 2/2015 | Paul, Jr. |
| 8,968,330 B2 | 3/2015 | Rosenbluth |
| 9,149,279 B2 | 10/2015 | Paul, Jr. |
| 9,149,609 B2 | 10/2015 | Ansel |
| 9,259,237 B2 | 2/2016 | Quick |
| 9,301,769 B2 | 4/2016 | Brady |
| 9,350,021 B2 | 5/2016 | Ohira |
| 9,351,749 B2 | 5/2016 | Brady |
| 9,351,861 B2 | 5/2016 | Sherburne |
| 9,393,035 B2 | 7/2016 | Yu |
| 9,402,707 B2 | 8/2016 | Brady |
| 9,408,620 B2 | 8/2016 | Rosenbluth |
| 9,439,661 B2 | 9/2016 | Johnson |
| 9,445,829 B2 | 9/2016 | Brady |
| 9,456,834 B2 | 10/2016 | Folk |
| 9,463,036 B2 | 10/2016 | Brady |
| 9,492,263 B2 | 11/2016 | Krolik |
| 9,526,864 B2 | 12/2016 | Quick |
| 9,526,865 B2 | 12/2016 | Quick |
| 9,579,116 B1 | 2/2017 | Nguyen |
| 9,642,635 B2 | 5/2017 | Vale |
| 9,642,639 B2 | 5/2017 | Brady |
| 9,700,332 B2 | 7/2017 | Marchand |
| 9,717,519 B2 | 8/2017 | Rosenbluth |
| 9,801,643 B2 | 10/2017 | Hansen |
| 9,815,038 B2 | 11/2017 | Leach |
| 9,820,769 B2 | 11/2017 | Krolik |
| 9,844,387 B2 | 12/2017 | Marchand |
| 9,855,067 B2 | 1/2018 | Krolik |
| 9,855,071 B2 | 1/2018 | Shaltis |
| 9,907,899 B2 | 3/2018 | Kim |
| 10,004,531 B2 | 6/2018 | Rosenbluth |
| 10,016,206 B1 | 7/2018 | Yang |
| 10,034,680 B2 | 7/2018 | Brady |
| 10,039,900 B2 | 8/2018 | Di Palma |
| 10,045,790 B2 | 8/2018 | Cox |
| 10,080,575 B2 | 9/2018 | Brady |
| 10,098,651 B2 | 10/2018 | Marchand |
| 10,201,360 B2 | 2/2019 | Vale |
| 10,213,582 B2 | 2/2019 | Garrison |
| 10,226,598 B2 | 3/2019 | Chou |
| 10,238,406 B2 | 3/2019 | Cox |
| 10,265,086 B2 | 4/2019 | Vale |
| 10,278,717 B2 | 5/2019 | Brady |
| 10,285,720 B2 | 5/2019 | Gilvarry |
| 10,292,722 B2 | 5/2019 | Brady |
| 10,292,723 B2 | 5/2019 | Brady |
| 10,299,811 B2 | 5/2019 | Brady |
| 10,300,256 B2 | 5/2019 | Aboytes |
| 10,335,186 B2 | 7/2019 | Rosenbluth |

(56) References Cited

U.S. PATENT DOCUMENTS

| | | |
|---|---|---|
| 10,342,571 B2 | 7/2019 | Marchand |
| 10,349,960 B2 | 7/2019 | Quick |
| 10,357,265 B2 | 7/2019 | Brady |
| 10,363,054 B2 | 7/2019 | Vale |
| 10,390,849 B2 | 8/2019 | Kugler |
| 10,390,850 B2 | 8/2019 | Vale |
| 10,420,570 B2 | 9/2019 | Vale |
| 10,441,301 B2 | 10/2019 | Vale |
| 10,456,555 B2 | 10/2019 | Garrison |
| 10,500,330 B2 | 12/2019 | Schwarz |
| 10,517,617 B2 | 12/2019 | Aklog |
| 10,517,622 B2 | 12/2019 | Vale |
| 10,517,708 B2 | 12/2019 | Gorochow |
| 10,524,811 B2 | 1/2020 | Marchand |
| 10,569,066 B2 | 2/2020 | Hayakawa |
| 10,582,939 B2 | 3/2020 | Brady |
| 10,588,648 B2 | 3/2020 | Brady |
| 10,588,649 B2 | 3/2020 | Brady |
| 10,588,655 B2 | 3/2020 | Rosenbluth |
| 10,610,246 B2 | 4/2020 | Brady |
| 10,617,435 B2 | 4/2020 | Vale |
| 10,667,833 B2 | 6/2020 | Vale |
| 10,675,045 B2 | 6/2020 | Brady |
| 10,682,152 B2 | 6/2020 | Vale |
| 10,682,454 B2 | 6/2020 | Coulthard |
| 10,729,459 B2 | 8/2020 | Krolik |
| 10,743,894 B2 | 8/2020 | Brady |
| 10,743,907 B2 | 8/2020 | Bruzzi |
| 10,772,649 B2 | 9/2020 | Hansen |
| 10,779,852 B2 | 9/2020 | Bruzzi |
| 10,792,055 B2 | 10/2020 | Brady |
| 10,792,056 B2 | 10/2020 | Vale |
| 10,799,331 B2 | 10/2020 | Hauser |
| 10,806,559 B2 | 10/2020 | Bonnette |
| 10,813,663 B2 | 10/2020 | Bruzzi |
| 10,842,498 B2 | 11/2020 | Vale |
| 10,874,421 B2 | 12/2020 | Bruzzi |
| 10,898,215 B2 | 1/2021 | Horowitz |
| 10,912,577 B2 | 2/2021 | Marchand |
| 10,952,760 B2 | 3/2021 | Brady |
| 10,953,200 B2 | 3/2021 | Sharma |
| 10,959,749 B2 | 3/2021 | Hatta |
| 11,000,682 B2 | 5/2021 | Merritt |
| 11,026,708 B2 | 6/2021 | Marks |
| 11,026,709 B2 | 6/2021 | Greenhalgh |
| 11,051,928 B2 | 7/2021 | Casey |
| 11,058,445 B2 | 7/2021 | Cox |
| 11,058,451 B2 | 7/2021 | Marchand |
| 11,065,018 B2 | 7/2021 | Buck |
| 11,076,876 B2 | 8/2021 | Vale |
| 11,154,314 B2 | 10/2021 | Quick |
| 11,253,277 B2 | 2/2022 | Buck |
| 11,259,821 B2 | 3/2022 | Buck |
| 11,266,825 B2 | 3/2022 | Peter |
| 11,432,835 B2 | 9/2022 | Shaffer |
| 11,439,799 B2 | 9/2022 | Buck |
| 11,457,936 B2 | 10/2022 | Buck |
| 11,529,495 B2 | 12/2022 | Keating |
| 11,553,935 B2 | 1/2023 | Buck |
| 11,554,005 B2 | 1/2023 | Merritt |
| 11,559,382 B2 | 1/2023 | Merritt |
| 11,607,478 B2 | 3/2023 | Gadrat |
| 11,633,272 B2 | 4/2023 | Buck |
| 11,642,209 B2 | 5/2023 | Merritt |
| 11,883,570 B2 | 1/2024 | Yao |
| 2001/0011179 A1 | 8/2001 | Adams |
| 2001/0031981 A1* | 10/2001 | Evans ............... A61B 17/221 606/200 |
| 2001/0044598 A1 | 11/2001 | Parodi |
| 2001/0049486 A1 | 12/2001 | Evans |
| 2002/0010487 A1 | 1/2002 | Evans |
| 2002/0058964 A1 | 5/2002 | Addis |
| 2002/0072764 A1 | 6/2002 | Sepetka |
| 2002/0087119 A1 | 7/2002 | Parodi |
| 2002/0120277 A1 | 8/2002 | Hauschild |
| 2002/0143387 A1 | 10/2002 | Soetikno |
| 2002/0151918 A1* | 10/2002 | Lafontaine ..... A61B 17/320725 606/159 |
| 2002/0151922 A1 | 10/2002 | Hogendijk |
| 2002/0161377 A1 | 10/2002 | Rabkin |
| 2002/0161427 A1 | 10/2002 | Rabkin |
| 2002/0165574 A1 | 11/2002 | Ressemann |
| 2002/0173815 A1 | 11/2002 | Hogendijk |
| 2002/0173819 A1* | 11/2002 | Leeflang ................. A61F 2/014 606/200 |
| 2002/0188276 A1 | 12/2002 | Evans |
| 2003/0023204 A1 | 1/2003 | Vo |
| 2003/0055445 A1 | 3/2003 | Evans |
| 2003/0093112 A1 | 5/2003 | Addis |
| 2003/0149467 A1 | 8/2003 | Linder |
| 2003/0195537 A1 | 10/2003 | Dubrul |
| 2003/0199890 A1 | 10/2003 | Dubrul |
| 2003/0236533 A1 | 12/2003 | Wilson |
| 2004/0019310 A1 | 1/2004 | Hogendijk |
| 2004/0064179 A1 | 4/2004 | Linder |
| 2004/0082962 A1 | 4/2004 | Demarais |
| 2004/0102728 A1 | 5/2004 | Foster |
| 2004/0147939 A1 | 7/2004 | Rabkin |
| 2004/0176659 A1 | 9/2004 | Peng |
| 2004/0181237 A1 | 9/2004 | Forde |
| 2004/0210298 A1 | 10/2004 | Rabkin |
| 2004/0260333 A1 | 12/2004 | Dubrul |
| 2005/0004594 A1 | 1/2005 | Nool |
| 2005/0080431 A1 | 4/2005 | Levine |
| 2005/0080480 A1 | 4/2005 | Bolea |
| 2005/0177022 A1 | 8/2005 | Chu |
| 2006/0009785 A1 | 1/2006 | Maitland |
| 2006/0041228 A1 | 2/2006 | Vo |
| 2006/0041304 A1 | 2/2006 | Jang |
| 2006/0047266 A1 | 3/2006 | Elkins |
| 2006/0047300 A1 | 3/2006 | Eidenschink |
| 2006/0047301 A1 | 3/2006 | Ogle |
| 2006/0095015 A1 | 5/2006 | Hobbs |
| 2006/0129095 A1 | 6/2006 | Pinchuk |
| 2006/0189930 A1 | 8/2006 | Lary |
| 2006/0195138 A1 | 8/2006 | Goll |
| 2006/0200191 A1 | 9/2006 | Zadno-Azizi |
| 2006/0229645 A1* | 10/2006 | Bonnette ........ A61B 17/320758 606/159 |
| 2006/0253145 A1 | 11/2006 | Lucas |
| 2006/0270974 A1 | 11/2006 | Goff |
| 2007/0027520 A1 | 2/2007 | Sherburne |
| 2007/0038241 A1 | 2/2007 | Pal |
| 2007/0118072 A1 | 5/2007 | Nash |
| 2007/0238917 A1 | 10/2007 | Peng |
| 2007/0239182 A1 | 10/2007 | Glines |
| 2008/0033482 A1 | 2/2008 | Kusleika |
| 2008/0041516 A1 | 2/2008 | Chiu |
| 2008/0065008 A1 | 3/2008 | Barbut |
| 2008/0103439 A1 | 5/2008 | Torrance |
| 2008/0249558 A1 | 10/2008 | Cahill |
| 2009/0018567 A1 | 1/2009 | Escudero |
| 2009/0054918 A1 | 2/2009 | Henson |
| 2009/0099581 A1 | 4/2009 | Kim |
| 2009/0137984 A1 | 5/2009 | Minnelli |
| 2009/0163846 A1 | 6/2009 | Aklog |
| 2009/0222035 A1 | 9/2009 | Schneiderman |
| 2009/0292307 A1 | 11/2009 | Razack |
| 2009/0306702 A1 | 12/2009 | Miloslavski |
| 2010/0030327 A1 | 2/2010 | Chatel |
| 2010/0057184 A1 | 3/2010 | Randolph |
| 2010/0274277 A1 | 10/2010 | Eaton |
| 2011/0009837 A1 | 1/2011 | Schreiner |
| 2011/0054504 A1 | 3/2011 | Porter |
| 2011/0160763 A1 | 6/2011 | Ferrera |
| 2011/0190806 A1 | 8/2011 | Wittens |
| 2011/0213290 A1 | 9/2011 | Chin |
| 2011/0213392 A1 | 9/2011 | Aklog |
| 2011/0275990 A1 | 11/2011 | Besser |
| 2012/0016455 A1 | 1/2012 | Sherburne |
| 2012/0059309 A1 | 3/2012 | Di Palma |
| 2012/0059356 A1 | 3/2012 | Di Palma |
| 2012/0150193 A1 | 6/2012 | Aklog |
| 2012/0197277 A1 | 8/2012 | Stinis |

(56) References Cited

U.S. PATENT DOCUMENTS

| | | |
|---|---|---|
| 2012/0253358 A1 | 10/2012 | Golan |
| 2013/0090624 A1 | 4/2013 | Munsinger |
| 2013/0289694 A1 | 10/2013 | Sherburne |
| 2013/0304082 A1 | 11/2013 | Aklog |
| 2014/0074144 A1 | 3/2014 | Shrivastava |
| 2014/0155908 A1 | 6/2014 | Rosenbluth |
| 2014/0171958 A1 | 6/2014 | Baig |
| 2014/0296868 A1 | 10/2014 | Garrison |
| 2014/0324091 A1 | 10/2014 | Rosenbluth |
| 2014/0350591 A1 | 11/2014 | Sherburne |
| 2014/0364833 A1 | 12/2014 | Christensen |
| 2015/0018859 A1 | 1/2015 | Quick |
| 2015/0127044 A1 | 5/2015 | Cahill |
| 2015/0238207 A1 | 8/2015 | Cox |
| 2015/0305756 A1 | 10/2015 | Rosenbluth |
| 2015/0314057 A1 | 11/2015 | Labib |
| 2015/0352325 A1 | 12/2015 | Quick |
| 2015/0360001 A1 | 12/2015 | Quick |
| 2016/0008014 A1 | 1/2016 | Rosenbluth |
| 2016/0038174 A1 | 2/2016 | Bruzzi |
| 2016/0095744 A1 | 4/2016 | Wolfertz |
| 2016/0106353 A1 | 4/2016 | Schuetz |
| 2016/0143721 A1 | 5/2016 | Rosenbluth |
| 2016/0206344 A1 | 7/2016 | Bruzzi |
| 2016/0262790 A1 | 9/2016 | Rosenbluth |
| 2016/0287276 A1 | 10/2016 | Cox |
| 2017/0079672 A1 | 3/2017 | Quick |
| 2017/0105745 A1 | 4/2017 | Rosenbluth |
| 2017/0112513 A1 | 4/2017 | Marchand |
| 2017/0112514 A1 | 4/2017 | Marchand |
| 2017/0136158 A1 | 5/2017 | Culhane |
| 2017/0189041 A1 | 7/2017 | Cox |
| 2017/0265878 A1 | 9/2017 | Marchand |
| 2017/0325839 A1 | 11/2017 | Rosenbluth |
| 2017/0333076 A1 | 11/2017 | Bruzzi |
| 2018/0042623 A1 | 2/2018 | Batiste |
| 2018/0092652 A1 | 4/2018 | Marchand |
| 2018/0193043 A1 | 7/2018 | Marchand |
| 2018/0256178 A1 | 9/2018 | Cox |
| 2018/0271556 A1 | 9/2018 | Bruzzi |
| 2018/0296240 A1 | 10/2018 | Rosenbluth |
| 2018/0344339 A1 | 12/2018 | Cox |
| 2018/0361116 A1 | 12/2018 | Quick |
| 2019/0046219 A1 | 2/2019 | Marchand |
| 2019/0070401 A1 | 3/2019 | Merritt |
| 2019/0150959 A1 | 5/2019 | Cox |
| 2019/0184076 A1 | 6/2019 | Gourlay |
| 2019/0231373 A1 | 8/2019 | Quick |
| 2019/0321071 A1 | 10/2019 | Marchand |
| 2020/0030504 A1 | 1/2020 | Igarashi |
| 2020/0046368 A1 | 2/2020 | Merritt |
| 2020/0164117 A1 | 5/2020 | Culhane |
| 2020/0178991 A1 | 6/2020 | Greenhalgh |
| 2021/0022766 A1 | 1/2021 | Bruzzi |
| 2021/0093758 A1 | 4/2021 | Corrales |
| 2021/0113224 A1 | 4/2021 | Dinh |
| 2021/0186537 A1 | 6/2021 | Buck |
| 2021/0186812 A1 | 6/2021 | Pennie |
| 2021/0187244 A1 | 6/2021 | Buck |
| 2021/0315598 A1 | 10/2021 | Buck |
| 2021/0316127 A1 | 10/2021 | Buck |
| 2021/0402086 A1 | 12/2021 | Jokaji |
| 2022/0104839 A1 | 4/2022 | Horowitz |
| 2022/0104840 A1 | 4/2022 | Horowitz |
| 2022/0125456 A1 | 4/2022 | Horowitz |
| 2022/0184290 A1 | 6/2022 | Herzlinger |
| 2022/0226555 A1 | 7/2022 | Sunenshine |
| 2022/0240959 A1 | 8/2022 | Quick |
| 2022/0330960 A1 | 10/2022 | Buck |
| 2022/0346800 A1 | 11/2022 | Merritt |
| 2022/0346813 A1 | 11/2022 | Quick |
| 2022/0346814 A1 | 11/2022 | Quick |
| 2023/0015259 A1 | 1/2023 | Buck |
| 2023/0046775 A1 | 2/2023 | Quick |
| 2023/0062809 A1 | 3/2023 | Merritt |
| 2023/0233311 A1 | 7/2023 | Merritt |

FOREIGN PATENT DOCUMENTS

| | | |
|---|---|---|
| AU | 2018328011 | 3/2020 |
| AU | 2019321256 A1 | 3/2021 |
| CA | 2939315 | 12/2015 |
| CA | 3002154 | 4/2017 |
| CA | 3074564 | 3/2019 |
| CA | 3114285 A1 | 2/2020 |
| CN | 1278713 | 1/2001 |
| CN | 1486758 | 4/2004 |
| CN | 108472052 | 8/2018 |
| CN | 109069790 | 12/2018 |
| CN | 110312481 | 10/2019 |
| CN | 112867455 A | 5/2021 |
| EP | 0518975 B1 | 5/1997 |
| EP | 2897536 | 7/2015 |
| EP | 3094363 | 11/2016 |
| EP | 3364891 | 8/2018 |
| EP | 3389757 | 10/2018 |
| EP | 3528717 | 8/2019 |
| EP | 3836855 A4 | 8/2022 |
| EP | 3362116 B1 | 6/2023 |
| JP | H025976 | 1/1990 |
| JP | 2003521286 | 7/2003 |
| JP | 2006015058 | 1/2006 |
| JP | 2007319272 | 12/2007 |
| JP | 6438495 | 12/2018 |
| JP | 2018537229 | 12/2018 |
| JP | 2018538027 | 12/2018 |
| JP | 2021534851 A | 12/2021 |
| WO | 9945835 | 9/1999 |
| WO | 2005079678 A1 | 9/2005 |
| WO | 2006029270 A1 | 3/2006 |
| WO | 2006063199 | 6/2006 |
| WO | 2006100651 A1 | 9/2006 |
| WO | 2010119110 | 10/2010 |
| WO | 2011144336 | 11/2011 |
| WO | 2012156924 | 11/2012 |
| WO | 2014093845 A1 | 6/2014 |
| WO | 2014141226 | 9/2014 |
| WO | 2015071852 A2 | 5/2015 |
| WO | 2016067246 A1 | 5/2016 |
| WO | 2016071524 | 5/2016 |
| WO | 2017070702 | 4/2017 |
| WO | 2017106877 | 6/2017 |
| WO | 2019050765 | 3/2019 |
| WO | 2021076954 | 4/2021 |
| WO | 2022082213 | 4/2022 |

OTHER PUBLICATIONS

Greenfield et al., Transvenous Removal of Pulmonary Emboli by Vacuum-Cup Catheter Technique, Journal of Surgical Research, vol. 9, No. 6(Jun. 1969) pp. 347-352.

International Search Report and Written Opinion for PCT/US2012/032291 mailed on Aug. 10, 2012, 14 pages.

International Search Report and Written Opinion for PCT/US2012/032295 mailed on Jul. 6, 2012, 13 pages.

International Search Report and Written Opinion for PCT/US2012/032306 mailed on Aug. 13, 2012, 12 pages.

International Search Report and Written Opinion for PCT/US2012/032311 mailed on Sep. 7, 2012, 14 pages.

International Search Report EP03252158_AESR dated Aug. 29, 2003, 1 page.

International Search Report EP08864356_SESR dated Apr. 1, 2014.

International Search Report PCT-NL-08-050399 ISR dated Feb. 13, 2009, 3 pages.

International Search Report PCT-US-08-072352 IPRP dated Nov. 4, 2008.

International Search Report PCT-US-12-032291 IPRP dated Aug. 10, 2012.

International Search Report PCT-US-12-032299 IPRP dated Oct. 2, 2012.

(56) References Cited

OTHER PUBLICATIONS

International Search Report PCT-US-12-032299 ISR dated Oct. 2, 2012.
International Search Report PCT-US-12-032299_WOSA dated Oct. 2, 2012.
International Search Report PCT-US-12-032306 IPRP dated Aug. 13, 2012.
International Search Report PCT-US-12-032306 ISR dated Aug. 13, 2012.
International Search Report PCT-US-12-032306_WOSA dated Aug. 13, 2012.
International Search Report PCT-US-12-032311 IPRP dated Sep. 7, 2012.
International Search Report PCT-US-12-032311_ISR dated Sep. 7, 2012.
International Search Report PCT-US-12-032311_WOSA dated Sep. 7, 2012.
Nael et al., Endovascular Management of Central Thoracic Veno-Occlusive Diseases in Hemodialysis Patients: A Single Institutional Experience in 69 Consecutive Patients, Journal of Vascular Interventional Radiology, vol. 20, No. 1, 2009, pp. 46-51.
Non-Final Office Action in U.S. Appl. No. 12/187,121, mailed Mar. 22, 2011, 14 pages.
Notice of Allowance dated Jan. 25, 2023 for U.S. Appl. No. 16/458,529 (pp. 1-2).
Notice of Allowance dated Nov. 1, 2022 for U.S. Appl. No. 16/458,529 (pp. 1-5).
Notice of Allowance dated May 12, 2022 for U.S. Appl. No. 16/797,188 (pp. 1-11).
Office Action cited in U.S. Appl. No. 12/187,121 mailed May 18, 2011, 14 pages.
Office Action dated Jan. 13, 2023 for U.S. Appl. No. 17/170,782 (pp. 1-12).
Office Action dated Jan. 19, 2023 for U.S. Appl. No. 16/279,216 (pp. 1-66).
Office Action dated Sep. 23, 2022 for U.S. Appl. No. 16/279,216 (pp. 1-10).
Office Action dated Apr. 8, 2022 for U.S. Appl. No. 16/279,216 (pp. 1-14).
Office Action dated Dec. 17, 2021 for U.S. Appl. No. 16/279,216 (pp. 1-11).
Office Action dated Dec. 30, 2020 for U.S. Appl. No. 16/279,216 (pp. 1-10).
Office Action dated Jul. 5, 2022 for U.S. Appl. No. 16/458,529 (pp. 1-8).
Office Action dated Jul. 12, 2021 for U.S. Appl. No. 16/279,216 (pp. 1-12).
Office Action dated Mar. 8, 2021 for U.S. Appl. No. 16/454,644 (pp. 1-9).
PCT International Search Report based on PCT/US2008/072352 dated Nov. 4, 2008, 1 page.
Valji, et al, Pulsed-Spray Thrombolysis of Arterial and Bypass Graft Occlusion, American Roentgen Ray Society, pp. 617-621 (Mar. 1991).
Behrens G, Bjarnason H. Venous Thromboembolic Disease: The Use of the Aspiration Thrombectomy Device AngioVac. Semin Intervent Radiol. 2015.
Hansman, Heather. "This Pump Could Make Blood Transfusions Safer and Cheaper in the Developing World." Smithsonian Magazine. Nov. 20, 2015, https://www.smithsonianmag.com/innovation/pump-could-make-blood-transfusions-safer-and-cheaper-developing-world-180957250/#:~:text=The%20Hemafuse%2C%20which%20looks%20like,where%20it%20can%20be%20retransfused (accessed Apr. 21, 2024).
Notice of Allowance dated May 21, 2024 for U.S. Appl. No. 16/778,657 (pp. 1-9).
Notice of Allowance dated Jun. 17, 2024 for U.S. Appl. No. 16/778,657 (pp. 1-2).
Sisu Global. "The Hemafuse." Jun. 2018, https://sisuglobal.health/hemafuse. (accessed Apr. 21, 2024).

* cited by examiner

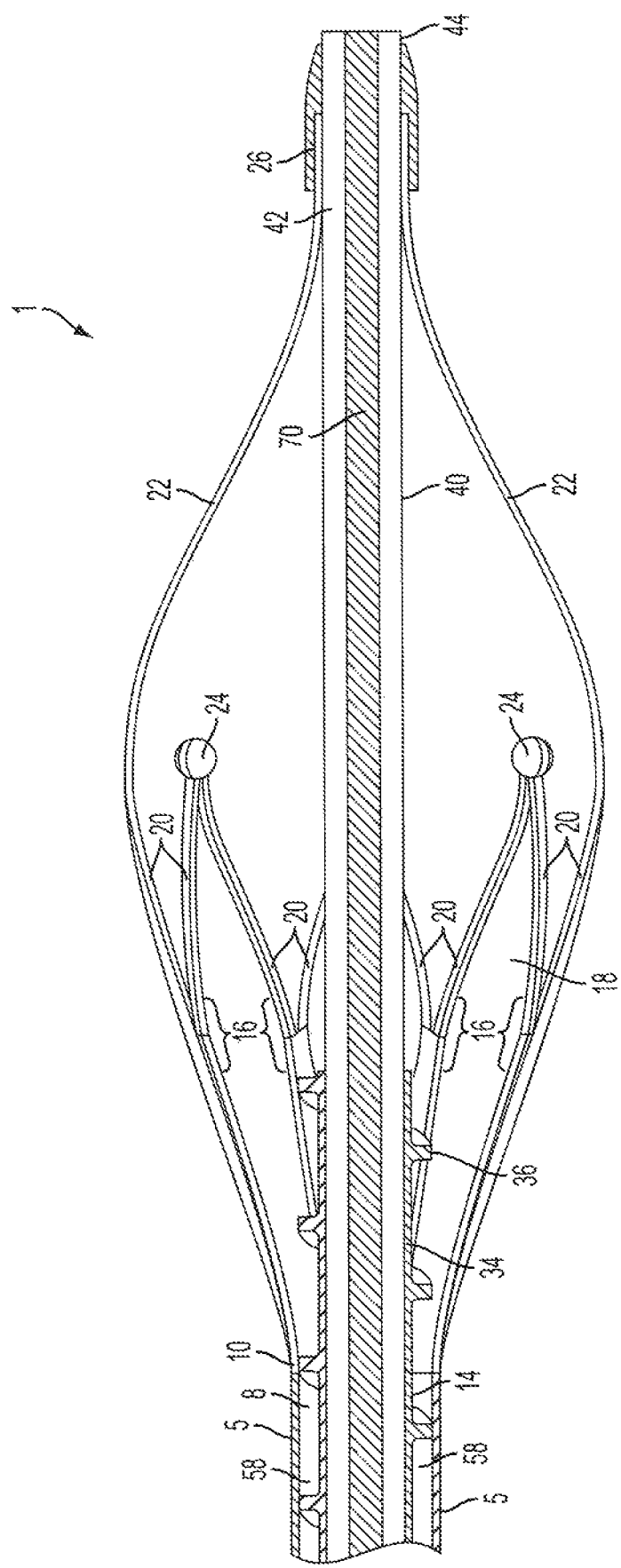

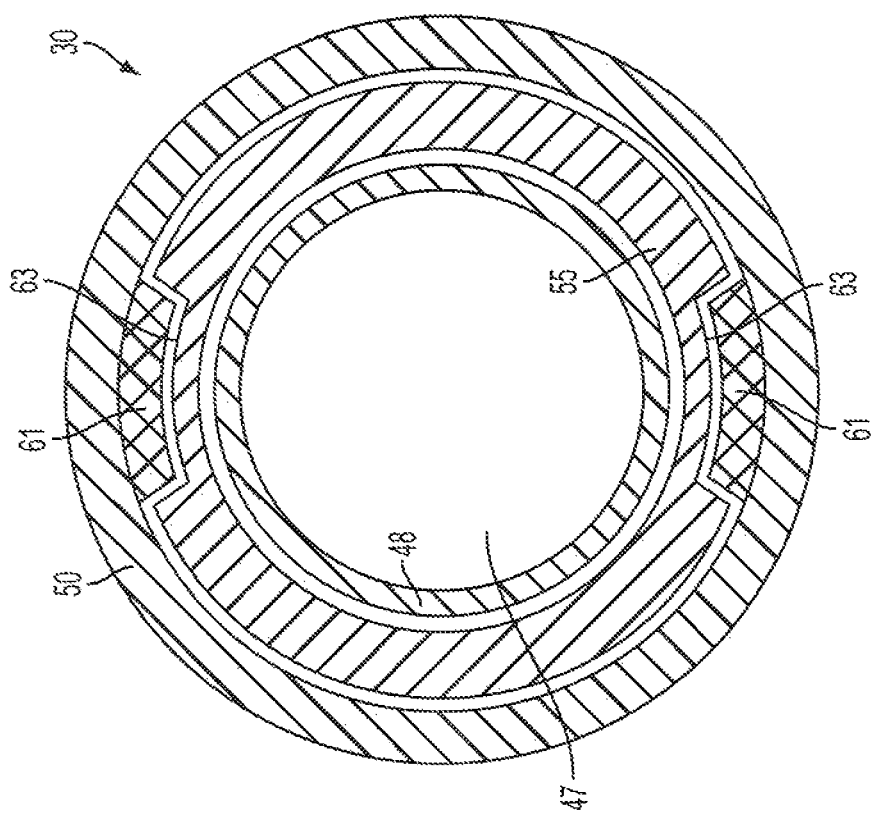

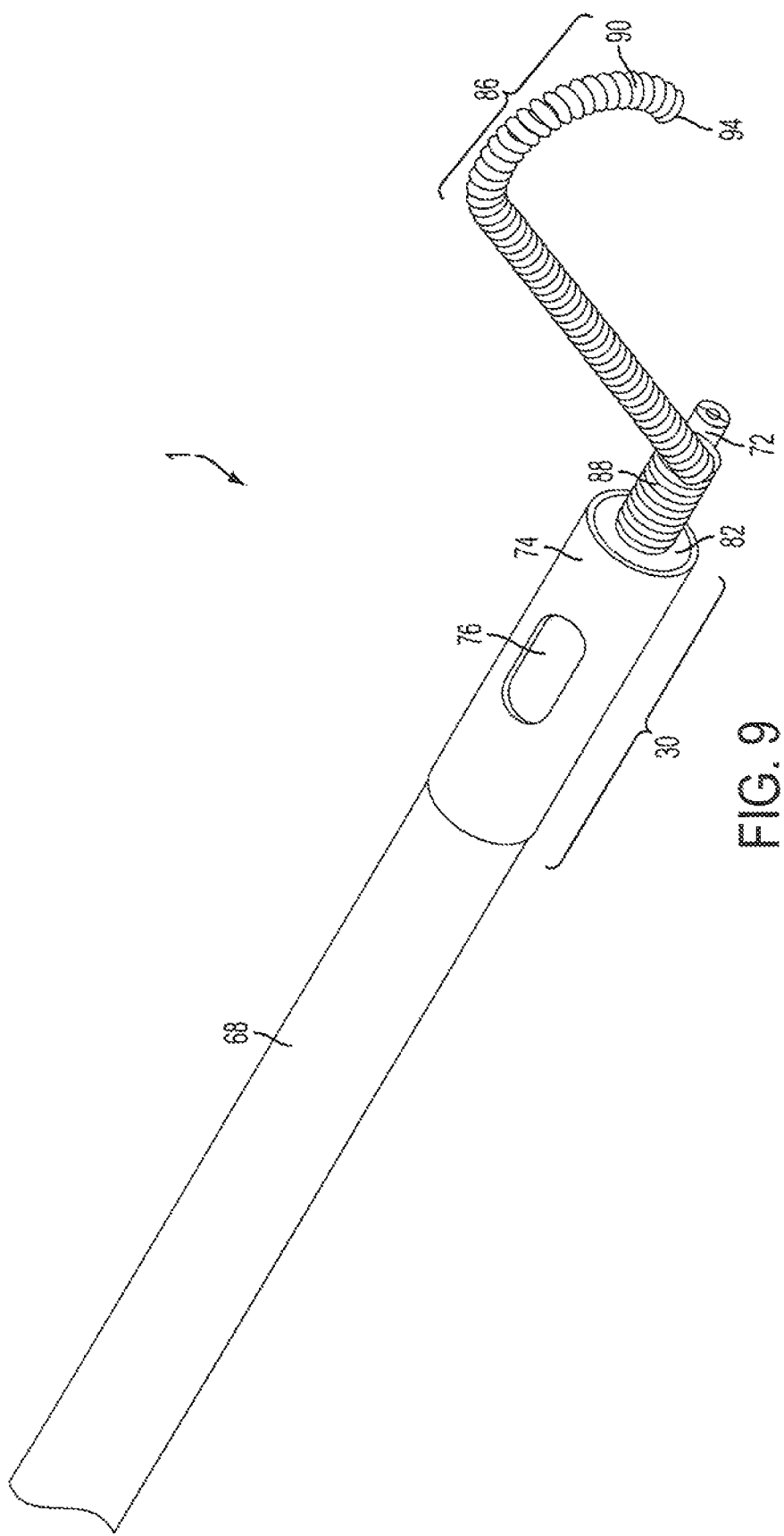

DEVICE AND METHOD FOR REMOVING MATERIAL FROM A HOLLOW ANATOMICAL STRUCTURE

CROSS REFERENCE TO RELATED APPLICATIONS

This application is a continuation-in-part of U.S. patent application Ser. No. 16/797,188, filed Feb. 21, 2020, which claims priority to U.S. patent application Ser. No. 14/708,355, filed May 11, 2015, which claims priority under 35 U.S.C. § 119(e) to U.S. Provisional Application No. 61/452,838, filed Mar. 15, 2011, U.S. Provisional Application No. 61/521,494, filed Aug. 9, 2011, and U.S. Provisional Application No. 61/585,348, filed Jan. 1, 2012, all of which are incorporated herein by reference.

BACKGROUND

Common types of treatment for removal of thrombus include fluid delivery, such as a lytic or other blood thinning medication. For example, a doctor may deliver a desired drug, such as lytic, to the treatment site adjacent to the clot in order to break down the clot matter. This manner of treatment may result in small pieces of clot remaining in the vessel after treatment, commonly attached to the vessel wall. Problems with known methods of clot removal is it's a common requirement for the patient to remain overnight in the hospital or the treatment may not completely remove the clot from the vessel. An object of this invention is to provide a mechanical means for aiding in the complete removal of clot material.

FIELD OF THE INVENTION

The present invention relates generally to devices for removing material from a hollow anatomical structure. More specifically, the invention relates to mechanically treating the targeted area with an elongated device having an expandable or inverted centering element, a drive shaft attached to a rotatable macerator element for breaking up, dislodging, or dissolving clot material, and an aspiration or vacuum source for removal of clot material. Additionally, the device contains open fluid communication channels and is capable of delivering various fluids, drugs or other medical preparations to a treatment site within a lumen of a blood vessel or another cavity or lumen within a patient's body.

SUMMARY OF THE DISCLOSURE

According to the principles of the present invention, a medical device for removing material from a hollow anatomical structure is provided. The device may include a hollow shaft member having a proximal and distal end and a drive shaft coaxially disposed within hollow shaft member. The drive shaft has a proximal and distal end and the proximal end may be attached to a motor or other drive mechanism. The device may also include an expandable or inverted centering element disposed near the distal end of the elongated shaft. The expandable or inverted segment may expand to a predetermined shape automatically upon deployment from a sheath, or alternatively the expandable or inverted segment may be hinged to the distal end of the shaft for manual expansion.

The device includes a macerator element near the distal end of the hollow shaft. The macerator element may be attached to the distal end of the drive shaft. The macerator element may be comprised of an auger element, rotating element, shearing member coaxially disposed and freely rotatable within an outer tubular extension, a rotating wire, or any combination of these various elements. The macerator element rotates along the central axis of the device to aid in mechanically removing, dissolving, disrupting, liquefying, or breaking down clot material from within a hollow anatomical structure. The rotations per minute and means for removing the clot material may change depending on the embodiment of macerator element being used. The device may include an aspiration or vacuum element to aid in removal of clot material. The device may be used in combination with a distal protection element, such as an expandable filter or inflatable balloon member.

A method for removing material from a hollow anatomical structure is provided, which includes the following steps. If used, the distal protection element may be placed at the treatment site. The device described above may be inserted near the treatment site by either back-loading it over a pre-placed guidewire or by inserting the device through a pre-placed procedure sheath. The expandable or inverted segment may expand to a predetermined shape automatically upon deployment from a sheath, or alternatively the expandable or inverted segment may be manual expanded and deployed. Once the device is properly in place, the drive shaft is attached to the motor mechanism which is then activated. As the drive shaft is rotated this also rotates the maceration element. Once macerator element has been activated the aspiration mechanism is then activated. Procedure is performed as the macerator element removes, dissolves, disrupts. liquefies, or breaks down clot material from within a hollow anatomical structure and this material is removed through the aspiration area. Optionally, the user may elect to deliver fluid through the device at any time throughout the procedure. Once procedure is complete the device is removed.

In one embodiment is a device for removing undesirable material from a body. The device comprising a catheter shaft comprising a catheter shaft lumen and a catheter shaft distal end portion; a drive shaft comprising a drive shaft lumen and a drive shaft distal end portion, the drive shaft coaxially positioned within the catheter shaft lumen; a macerator assembly coupled to the catheter shaft distal end portion and the drive shaft distal end portion; a guidewire tube comprising a guidewire tube distal end, the guidewire tube coaxially positioned within the drive shaft lumen and extending a select distance distally beyond the drive shaft distal end portion, and the guidewire tube distal end coupled to a leading distal tip of the device; an expandable centering cage comprising an expandable centering cage distal end coupled to the leading distal tip; and wherein the drive shaft and the macerator assembly are independently moveable relative to the guidewire tube.

Wherein the expandable center cage further comprises an expandable center cage distal section and a cover positioned over at least a portion of the expandable center cage distal section.

Wherein the cover is configured to capture and/or entrap the undesirable material within the expandable centering cage.

The device further comprising an cage control tube comprising a cage control tube distal end, the cage control tube distal end coupled to an expandable centering cage proximal end; the cage control tube coaxially positioned over the catheter shaft.

Wherein the cage control tube is configured to adjust an expanded diameter of the expandable centering cage.

Wherein the device further comprising an aspiration channel in fluid communication with the macerator assembly.

Wherein the expandable centering cage comprises a first set of legs and a second set of legs, the first set of legs extend a select distance distally beyond the expansion control tube distal end, and the second set of legs extend a select distance distally beyond a distal end of the first set of legs.

Wherein the first set of legs comprise a first bifurcate wire assembly, and wherein the second set of legs comprise a second bifurcate wire assembly.

Wherein the first bifurcate wire assembly is coupled to the second bifurcate assembly at least two junction points.

Wherein the bifurcate wire assembly comprise up to eight total junction points.

Wherein the catheter shaft, the drive shaft, and the macerator assembly are coaxially independently moveable relative to the expandable centering cage.

Wherein the catheter shaft, the drive shaft, and the macerator assembly are coaxially independently movable relative to the expansion control tube.

Wherein the catheter shaft, the drive shaft, and the macerator assembly are configured to be coaxially movable between a first treatment position and a second treatment position.

Wherein the catheter shaft, the drive shaft, and the macerator assembly are configured to be coaxially movable between the first treatment position and the second treatment position while the guidewire tube and the expandable centering cage remains stationary.

In one embodiment a method for removing undesirable material from a hollow anatomical structure is described. The method comprising inserting a device into the hollow anatomical structure, the device comprising: a catheter shaft comprising a catheter shaft lumen and a catheter shaft distal end portion; a drive shaft comprising a drive shaft lumen and a drive shaft distal end portion, the drive shaft coaxially positioned within the catheter shaft lumen; a macerator assembly coupled to the catheter shaft distal end portion and the drive shaft distal end portion; a guidewire tube comprising a guidewire tube distal end, the guidewire tube coaxially positioned within the drive shaft lumen, and the guidewire tube distal end coupled to a leading distal tip of the device; an expandable centering cage comprising an expandable centering cage distal end, an expandable centering cage collapsed position, and an expandable centering cage expanded position, the expandable centering cage distal end coupled to the leading distal tip; and wherein the drive shaft and the macerator assembly are independently moveable relative to the guidewire tube; advancing the leading distal tip, at least a portion of the guidewire tube, and the expandable centering cage in the collapsed position through the undesirable material; deploying the expandable centering cage to the expanded position; retracting the device to capture at least a portion of the undesirable material within the expandable centering cage; activating the macerator assembly; advancing the catheter shaft, the drive shaft, and the macerator element within the expandable centering cage to macerate at least a portion of the captured undesirable material.

The method further comprising rotating the expandable centering cage to increase the likelihood of dislodging undesirable material.

The method further comprising inserting a guidewire into the hollow anatomical structure; placing the guidewire through a guidewire lumen of the guidewire tube; and advancing the device over the inserted guidewire.

The method further comprising retracting the catheter shaft, the drive shaft, and the macerator element within the expandable centering cage; and repositioning the catheter shaft, the drive shaft, and the macerator element within the expandable centering cage to macerate at least a portion of the captured undesirable material.

The method further comprising wherein the device further comprising an expansion control tube, further comprising the step: moving the expansion control tube to adjust the diameter of the expandable centering cage.

The method further comprising moving the expansion control tube to collapse the expandable centering cage.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, wherein:

FIG. 2B illustrates a partial cross-sectional view of the distal portion of the device showing the expandable centering element and auger element with an inner shaft extending to the distal end of the centering element.

FIG. 4C illustrates a cross-sectional view of the device taken along lines B-B of FIG. 5.

FIG. 9 is a partial, isometric view of a macerator assembly with a shearing macerator element and a rotating wire element for macerating the clot mass.

FIG. 1C illustrates an enlarged, cross-sectional view of the manually expandable cage section in an undeployed position.

DETAILED DESCRIPTION OF THE INVENTION

Figure 1A:
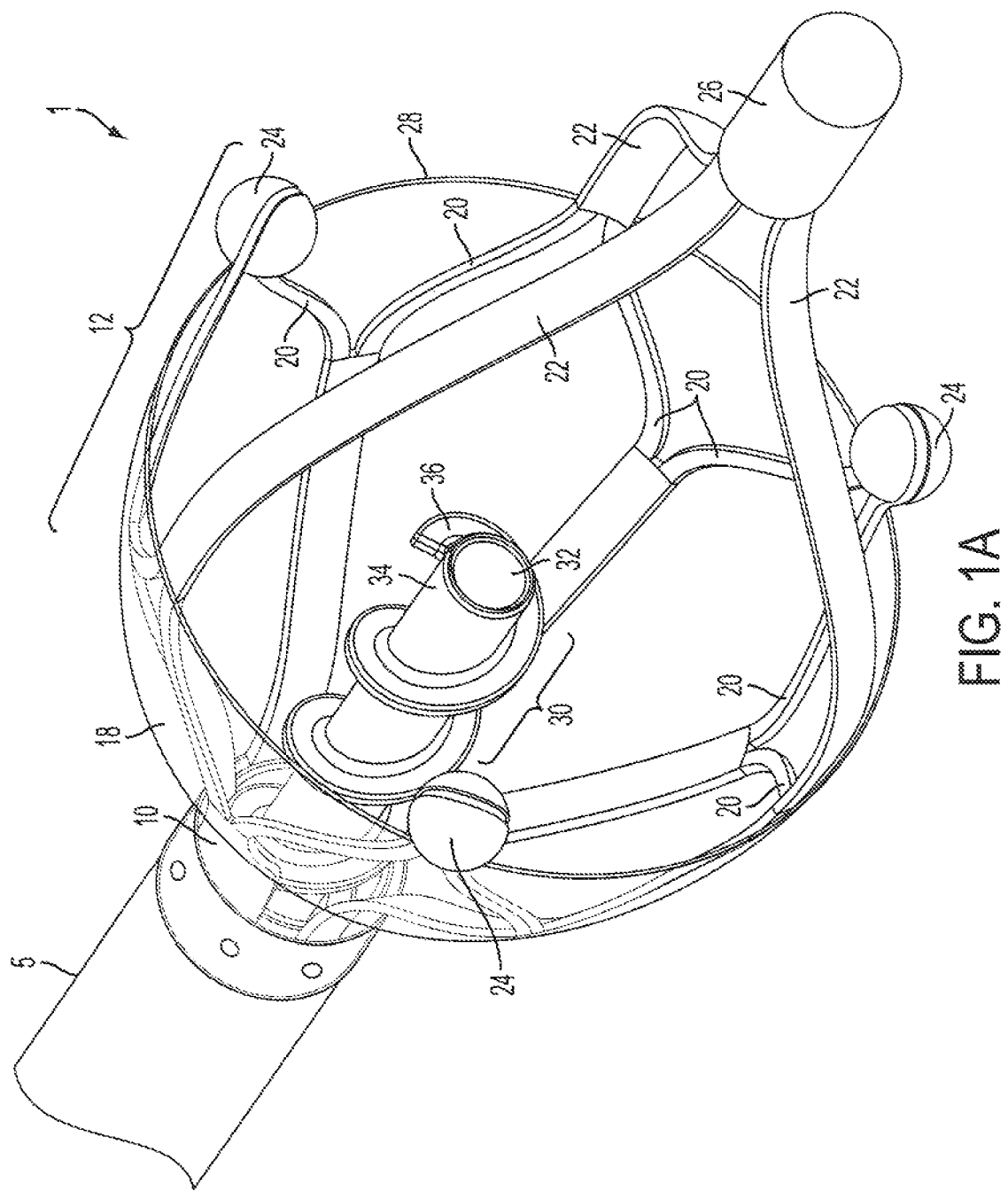
FIG. 1A depicts an isometric partial view of the distal portion of the device showing the expandable centering element and auger element.
Figure 1B:
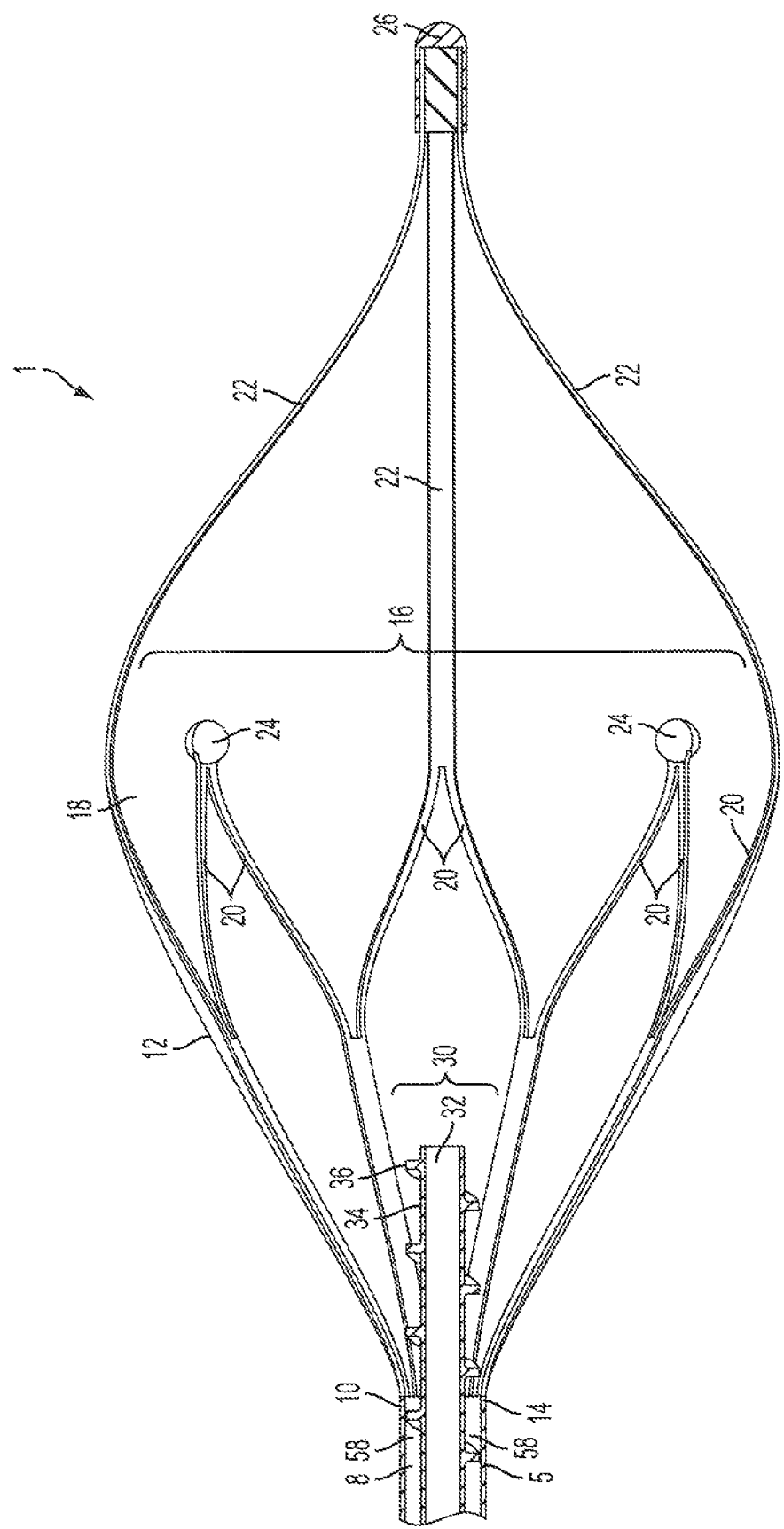
FIG. 1B illustrates a partial plan side view of the distal portion of the device showing the expandable centering element and auger element.

The present invention can be understood more readily by reference to the following detailed description and the examples included therein and to the figures and their previous and following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

As used herein, the term "proximal" denotes the direction closer to the operator and the term "distal" denotes the direction closer to (inserted into) the patient.

The clot removal device of the present invention allows a user to mechanically dislodge, disrupt, dissolve, liquefy, break-down or remove a clot, thrombus or other build-up of material formed against a vessel wall. This invention is advantageous for treatment of build-up of material formed against a vessel wall because the material will be mechanically detached and removed away from the vessel wall which reduces reformation of localized clot post treatment. The treatment device may allow the user to manually control various aspects of the clot removal, including but not limited to the expansion and collapse of an expandable centering device, cage, filter or inverted centering element, the speed or rotation of the macerator element, and the aspiration of dislodged and broken down clot material for complete removal from the vessel. Additionally, the invention allows for the option of delivery of fluid to the treatment site.

Referring now in detail to the drawings, in which like reference numerals indicate like parts or elements throughout the several views, in various embodiments, presented herein is a treatment device intended for the removal of clot material from a vessel.

FIGS. 1A-2B illustrate one aspect of the invention wherein thrombus may be removed from a vessel using clot removal device 1. The clot removal device 1 may be comprised of an elongate outer shaft 5, a macerator element 30, expandable member 12, and aspiration area 58. The outer shaft 5 has a through lumen 8, as shown in FIG. 1B, which extends from a proximal end of the device (not shown) to a proximal end 10 of an expandable member 12 where the through lumen 8 terminates in a distal end 14. Clot removal device 1 may be in the range of 6 F to 20 F in size so as to facilitate removal of clot from both small and large vessels. A preferred size of the clot removal device 1 may be 8 F wherein the outer shaft 5 may have an outer diameter of 0.103 inches and an inner diameter of 0.086 inches.

An advantage of the expandable member 12 is that it may be compressed during insertion of the device 1, and once device 1 is placed at treatment site expandable member 12 may expand out radially to center the macerator element 30 within center of vessel lumen. Expandable member 12 may be comprised of a frame 16. When expanded, frame 16 extends radially outward from the distal end 14 of shaft 5 to a maximum diameter before converging radially inward toward distal leading end 26. Frame 16 is comprised of proximal legs which split into wire members 20. Adjacent wire members 20 extend distally and converge either at an atraumatic bead 24 or to form a plurality of distal frame legs 22. The wire members 20 may be made from a shape memory material, such as nitinol or stainless steel, so that the expandable member 12 may be compressed or collapsed during insertion and then fully expanded to a preset shape once at the target site. Alternatively, cover 18 may be positioned over the frame 16. The cover 18 may be either a permeable material or non-permeable material.

In the depicted embodiment the plurality of distal frame legs 22 may extend from the remaining alternate converging wire members 20 distally in an inward direction toward the longitudinal axis of the clot removal device 1. Distal frame legs 22 terminate in a distal leading end 26. Distal frame legs 22 may extend distally, approximately 0.5 inches to 2.0 inches, from a distal end 28 of the non-permeable material 18 to the distal leading end 26. Although the figures detail four distal frame legs 22, this may only be exemplary and any reasonable number of legs may be employed.

Distal leading end 26 and beads 24 may be used for atraumatic advancement of the clot removal device 1 through the vessel and for preventing perforation through the vessel wall. When expanded, the expandable member 12 centers the clot removal device 1 within the center of the target vessel. In its expanded position the expanded member 12 may have a diameter in the range of 10 mm to 20 mm. The user may advance the expandable member 12 towards the clot so distal frame legs 22 or beads 24 aid in mechanically agitating or disrupting the clot and assist in separating the clot mass from the vessel wall.

Clot removal device 1 further includes a macerator element 30. In this embodiment the macerator element 30 is comprised of an auger 32 element. Auger 32 consists of a longitudinal tube 34 body having a helical member 36 disposed along the outer surface of the tube 34. Auger 32 may be capable of clockwise and/or counter-clockwise movement. Longitudinal tube 34 may either consist of a solid or a hollow closed end tubular member. The auger 32 may be coaxially disposed within the through lumen 8 of the outer shaft 5 of the clot removal device 1. The auger 32 may extend approximately 0.25 inches to 5.0 inches from the distal end 14 of the outer shaft 5.

Figure 2A:
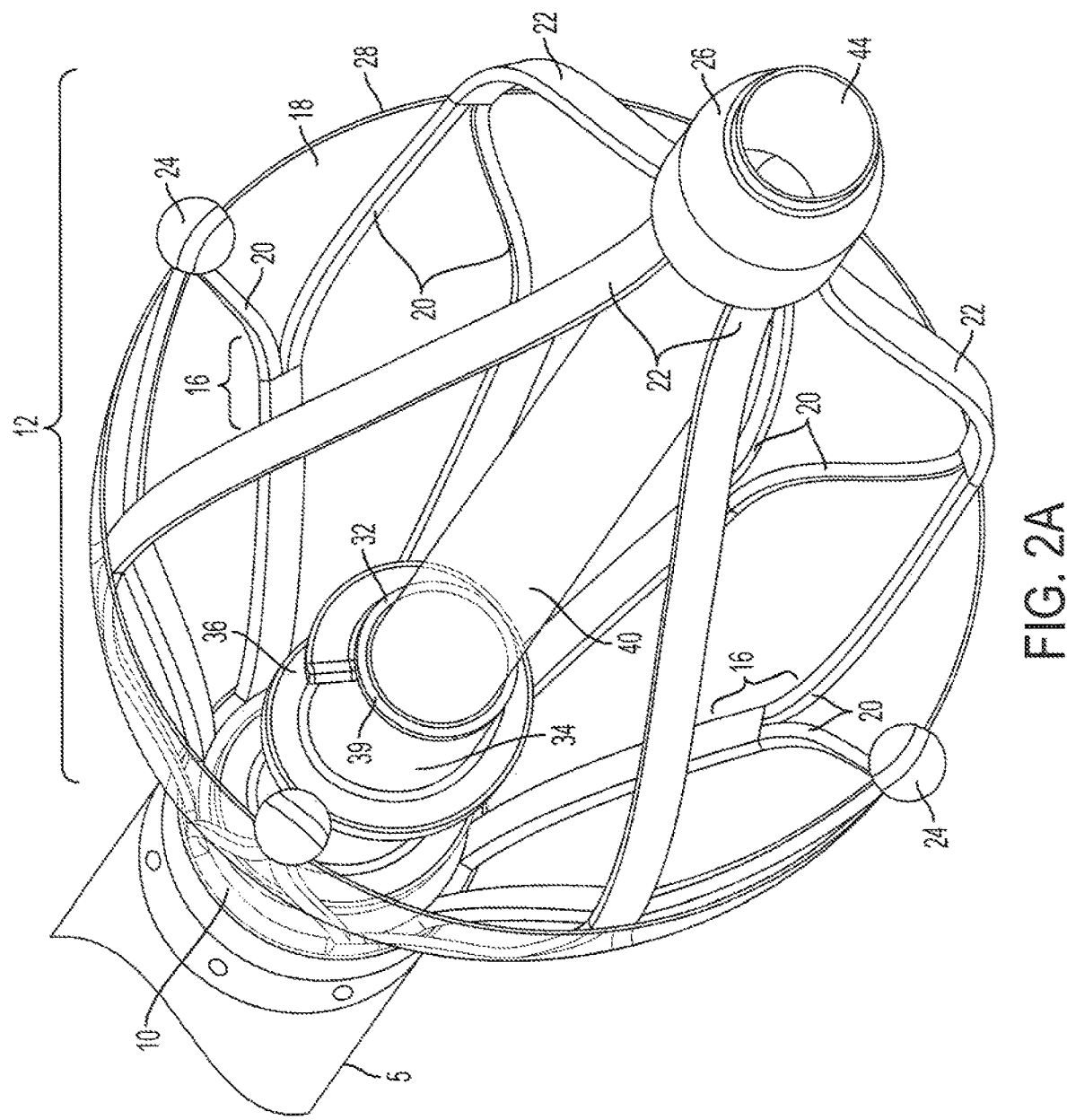
FIG. 2A depicts an isometric partial view of the distal portion of the device showing the expandable centering element and auger element with an inner shaft extending to the distal end of the centering element.

Alternatively, this embodiment may be used over a guidewire, as seen in FIG. 2A-2B. For example, coaxially positioned within lumen 38 of the auger 32 may be an inner shaft 40 which extends from the proximal end of the device and emerges from distal end 39 of the auger 32. Inner shaft 40 includes an inner through lumen 42 and further extends through the expandable member 12 to terminate at an open distal tip 44 to facilitate advancement of guidewire through the expandable cage portion of the device. The inner through lumen 42 of inner shaft 40 may provide for the introduction and removal of medical devices known in the art, such as guidewires, distal protection devices or occlusion balloons. As one example shown in FIG. 2B, a guidewire or distal occlusion element 70 may be advanced through the inner through lumen 42 and positioned distally of the target treatment area to capture any residual emboli created by the clot removal procedure. Alternatively, the device 1 may also be back-loaded over a guidewire that has already been placed at treatment site. Once the device 1 and distal occlusion element are in place, the auger 32 may then be activated and further advanced toward the clot to mechanically break down the clot material into smaller pieces. The user may aspirate the broken down clot material for removal through the aspiration area 58.

The auger 32 rotates around the central axis via connection to a drive shaft. The auger 32 may have the ability of being advanced and/or retracted within the through lumen 8 outer shaft 5 or may be stationary during use. The drive shaft may be secured to the inner lumen 38 of the auger 32 by conventional techniques such as, but not limited to, dog bone coupling, spline coupling, press fit, use of a known adhesive, or other known methods for coupling with ability to rotate. When activated, rotation of the drive shaft causes rotation of the auger 32 in either a clockwise or counter-clockwise direction. During use the auger 32 may be rotated approximately up to 5,000 RPMs and may have a pitch in the range of 0.5 helical members per inch to 10 helical members per inch, with a preferred pitch of 8 helical members per inch. Although a pitch of 8 helical members per inch may be preferred, conceivably, the auger 32 may have helical members that vary in dimension per inch along the length of the auger 32.

Rotation of the auger 32 causes the clot mass to be drawn into an annular space 58 defined between the helical member 36 and the through lumen 8 outer shaft 5. As the clot mass is drawn into this annular space the clot may be sheared, chopped, or macerated into smaller fragments and may be aspirated. Clot removal device 1 may also be attached to an external vacuum syringe or pump (not shown) which provides the clot removal device 1 with the ability to aspirate small clot fragments from within the vessel and/or annular space of the clot removal device 1 for removal. The auger 32 and external vacuum syringe or pump may work together or independently to remove thrombus particles from the vessel and/or clot removal device 1.

For the method of this embodiment the clot removal device 1 may be introduced into the target vessel or other anatomical site using minimally invasive access techniques known in the art. During insertion, the expandable member 12 may be collapsed within a procedure sheath (not shown). The clot removal device 1 may be advanced into position adjacent the clot. The procedure sheath may be proximally retracted allowing for deployment of the expandable member 12. Distal leading end 26 of the legs 22 provides for atraumatic advancement or retraction of the clot removal device 1 through the vessel after expansion.

Expansion of the expandable member 12 centers the macerator element 30 of clot removal device 1 within the vessel. During expansion of the expandable member 12 the beads 24 aid in preventing perforation through the vessel wall. Upon proper positioning of the clot removal device 1 within the vessel the auger 32 may be advanced distally towards the thrombus or other material being removed from vessel (not shown). Activation of the driveshaft causes rotation and advancement of the auger 32 allowing helical member 36 to disrupt the clot by engaging and entangling materials within the clot, particularly fibrin fibers which make up a substantial portion of the clot material. Auger 32 may be advanced and/or retracted while rotating to disrupt the clot material. Clot material not aspirated through the movement of the auger 32 may be aspirated through aspiration area 58. The expandable member 12 may be rotated to assist in the dislodging or detaching of the clot from the vessel wall.

Although the current design anticipates disruption of the clot material without the use of a lysing agent, a practitioner might optionally use a lysing agent to further enhance treatment outcome during the procedure. The lysing agent may be introduced through the through lumen 8 of the outer shaft 8 or through the luminal space through the auger 32.

Upon completion of the procedure, if the auger 32 was advanced, the auger 32 may then be retracted to its original position and the clot removal device 1 may be withdrawn within the procedure sheath, thereby collapsing the expandable member 12 where any potentially remaining clot particles may be captured and removed as the clot removal device 1 may be withdrawn from the patient. This method contemplates clot disruption and removal with minimum risk of injury to the vessel.

Figure 3:
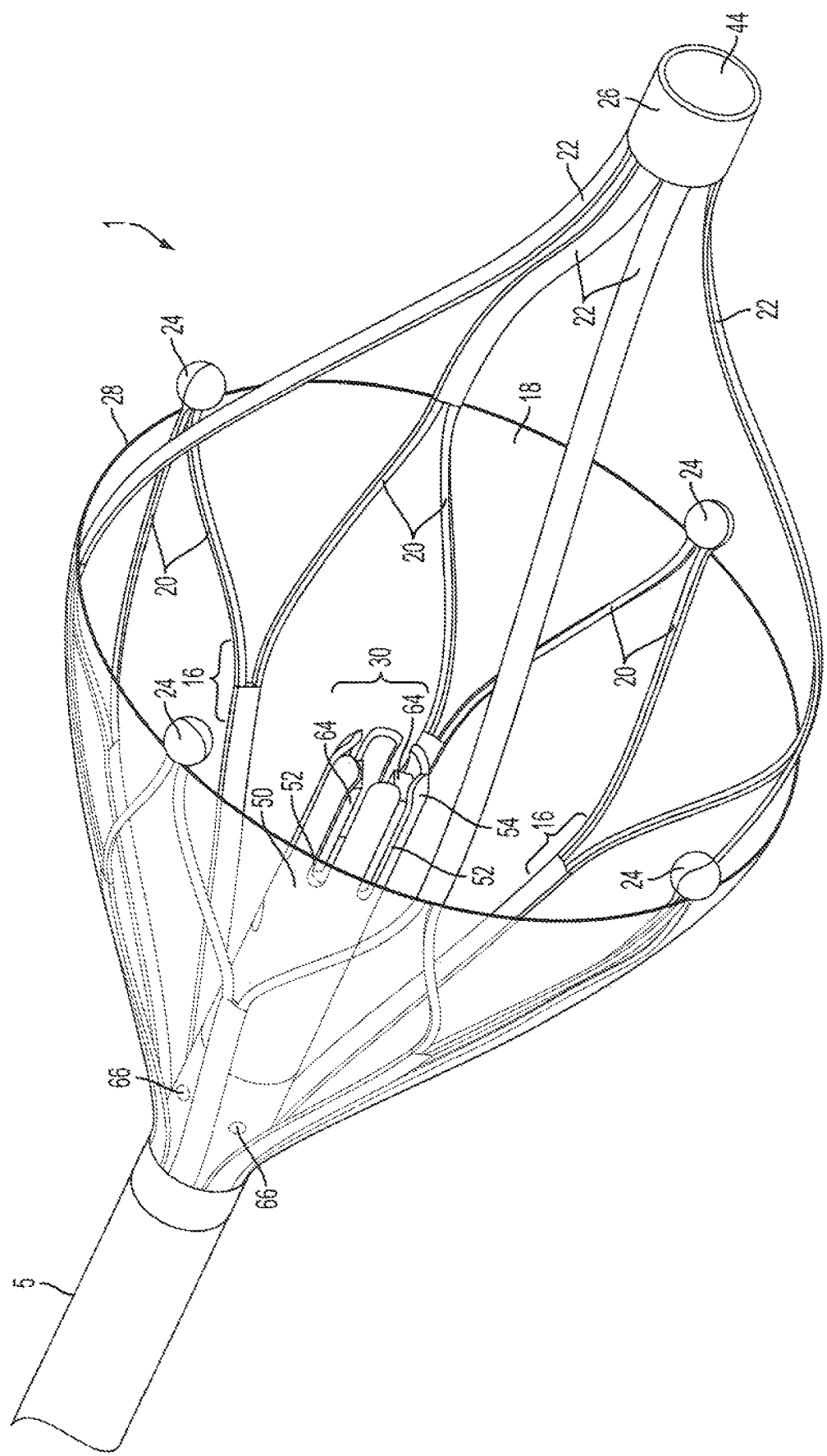
FIG. 3 is a partial, isometric view of the distal portion of the device illustrating another embodiment of the expandable centering element and rotating macerator element.
Figure 4A:
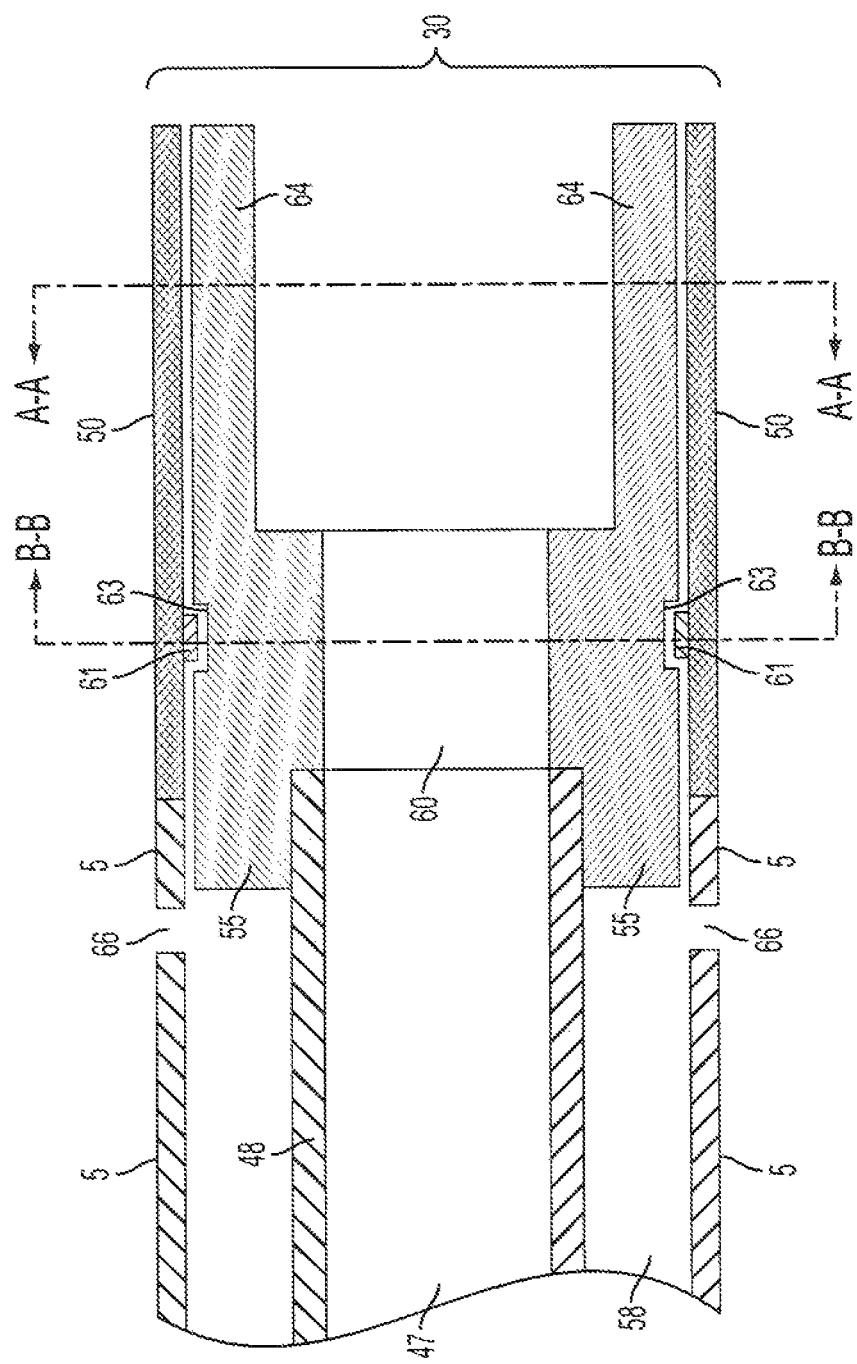
FIG. 4A is a partial, cross-sectional view of the distal portion the embodiment of FIG. 3.

FIGS. 3-4C illustrate yet another aspect of the invention. The clot removal device 1 is similar as describe above, however in this embodiment the maceration element 30 is comprised of a rotating member 64. An advantage of the macerator element 30 depicted in this embodiment, and similarly depicted in embodiments shown in FIGS. 12A-13C, is the rotating member 64 is capable of rotating at high speeds and when used in combination with aspiration or vacuum a vortex is created to aid in removal of material from vessel, as described in more detail below. The macerator element 30 of this embodiment consists of tubular extension 50 securely attached to the distal end of the outer shaft 5 and a rotating member 64 attached to the distal end of a drive shaft 48, as seen in FIG. 4A. Tubular extension 50 may be attached to the outer shaft 5 by conventional techniques such as, but not limited to, welding, adhesive bonding or step attachment and adhesive bonding, to the outer shaft 5. Tubular extension 50 includes a either a single slot 52 or a plurality of slots 52 or cut-outs. The slots 52 may be formed in a distal end 54 of the tubular extension 50.

As shown in FIG. 4A, a longitudinal drive shaft 48 may be coaxially disposed within outer shaft 5 and extends therethrough for attachment to a motor at proximal end (not shown). Near the distal end of the outer shaft 5 may be aspiration holes 66. The aspiration holes 66 may be created by drilling a hole through outer shaft 5, proximal end of tubular shaft 50, or both. A suction or vacuum apparatus (not shown) may be attached at proximal end of outer shaft 5 so when suction is applied this forces fluid and material to travel from inside vessel lumen through the aspiration holes 66 into aspiration area 58 for removal.

Figure 4B:
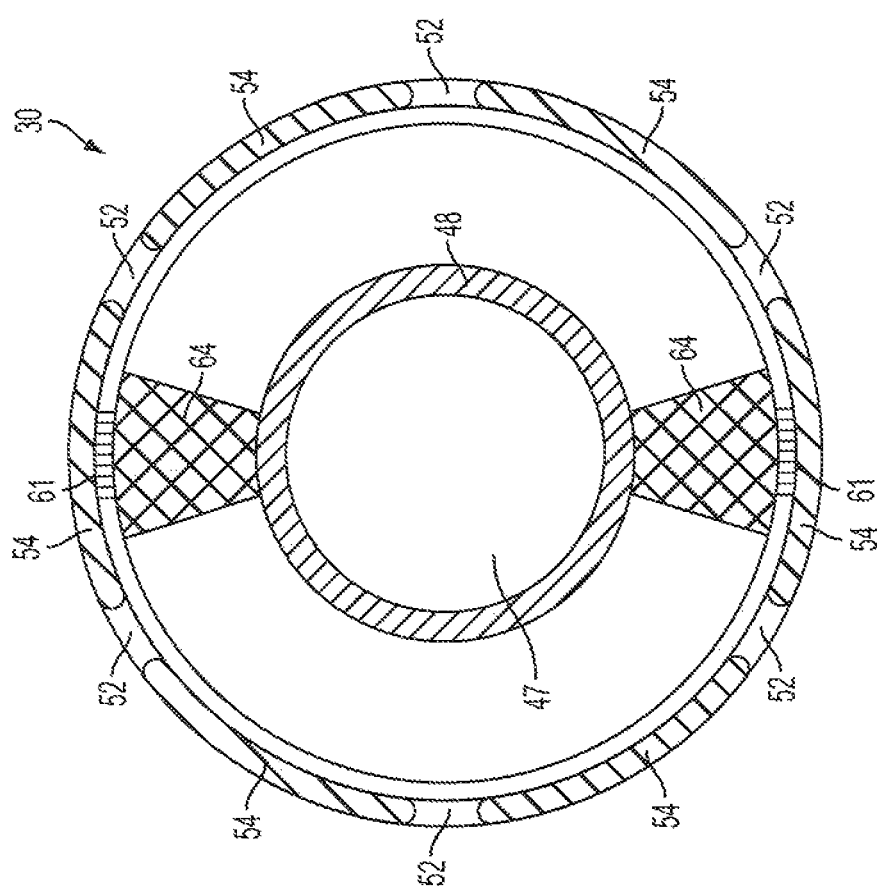
FIG. 4B illustrates a cross-sectional view of the device taken along lines A-A of FIG. 4A.
Figure 5:
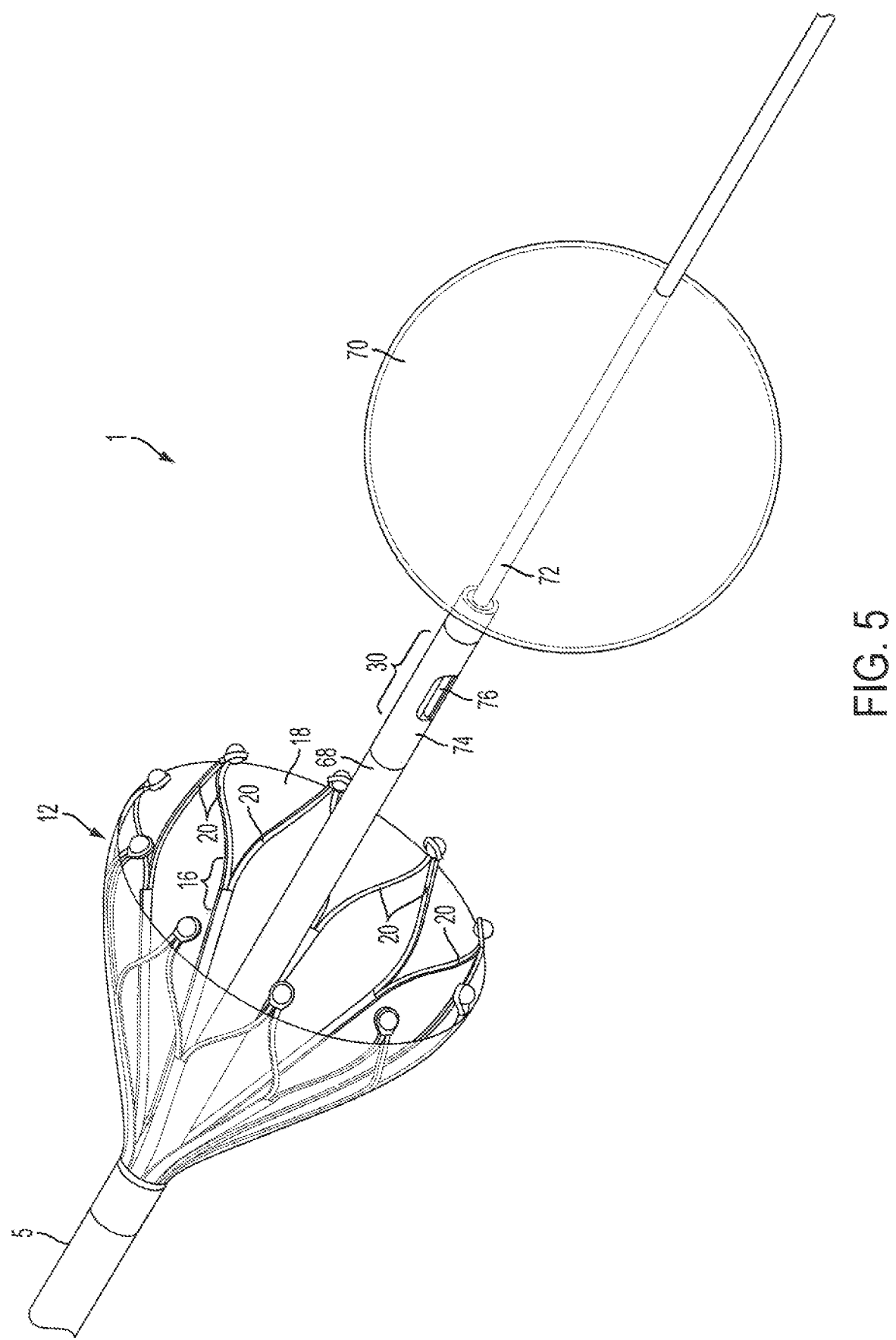
FIG. 5 is a partial, isometric view illustrating another embodiment of the expandable centering element and shearing rotating macerator element, and the device being used in combination with an embolic protection device in the form of an inflatable balloon.

The rotating member 64 may be made of PEEK, plastic, metal such as nitinol or stainless steel, or any other suitable material. The rotating member 64 may freely spin or rotate along the longitudinal axis within the distal ends 54 of tubular extension 50, as seen in FIG. 4B. A hole may be created in the distal end 55 of the rotating member 64. The size of this hole may be slightly larger than the outer diameter of the distal end 60 of the drive shaft 48 so that the distal end 60 of the drive shaft 48 may be securely inserted and fastened to the rotating member 64 via a press fit or interference fit. Alternatively, the rotating member 64 may be attached by conventional techniques such as, but not limited to, press fit, interference fit, welding, adhesive bonding or step attachment and adhesive bonding, to the distal end 60 of the drive shaft 48.

To prevent the rotating member 64 from unwanted shifting or unintended advancement inside the inner tube 5 a bulge, protuberance, extension, or bump 61 and groove 63 system may be used, as seen in FIG. 4C. The bump 61 may be an inward extension of the tubular extension 50 or an additional element connected to the inner wall of tubular extension 50. The bump 61 is sized to fit within a corresponding groove 63, notch or cut-out of the rotating member 64. Such a system will allow the rotating member 64 to freely spin and rotate within the tubular extension 50 while simultaneously preventing rotating member 64 from unintended shifting proximally or distally along the longitudinal axis.

The drive shaft 48 is rotated by activation of a motor. Conceivably, the drive shaft 48 may be capable of clockwise and/or counterclockwise movement. Because the rotating member 64 is securely attached to drive shaft 48 both elements will rotate at the same speed. The drive shaft 48 and rotating member 64 of this embodiment may rotate up to 200,000 RPMs (rotations per minute). Rotation of the rotating member 64 within the tubular extension 50 combined with aspiration or vacuum through aspiration holes 66 may create a vortex within the vessel lumen. The vortex is created by the spinning, flowing, and swirling of turbulent fluid around the centrally located macerator element 30, such as the high speed rotation of rotating member 64. The vortex creates a force within vessel lumen that aids in pulling and detaching the clot away from the vessel wall. For example, a vortex may be created within vessel lumen and aid removal of clot material when the drive shaft 48 and rotating member 64 are rotated at speeds ranging from 10,000 rpms-80,000 rpms. In addition to creating a vortex, the rotating member 64 may be advanced towards the clot so the rotating member 64 physically cut, chop, shear, and macerate the thrombus. The combination of a dissolving clot material with the creation of a vortex and the mechanical breakdown of the clot material by the rotation of the rotating member 64 result in breaking the clot into significantly small particles and aides in drawing the macerated material into the aspiration area 58 for removal.

Referring now to FIGS. 5-8C, yet another embodiment of the clot removal device 1 is shown. In this embodiment, the clot removal device 1 may be comprised of an outer shaft 5 having a through lumen 8, an inner shaft 68, a macerator element 30 comprising of a shearing member 80. This embodiment may also have an expandable centering element 12 as described above and be using in combination with an occlusion shaft 72 having a distal occlusion element 70. If the expandable centering element 12 is used it may be securely attached near the distal end of either the outer shaft 5 or inner shaft 68. Clot removal device 1 for this embodiment may be in the range of a 6 F to 20 F in size so as to facilitate removal of clot from both small and large vessels. The shearing member 80 may be able to rotate up to approximately 10,000 rpms.

Figure 6:
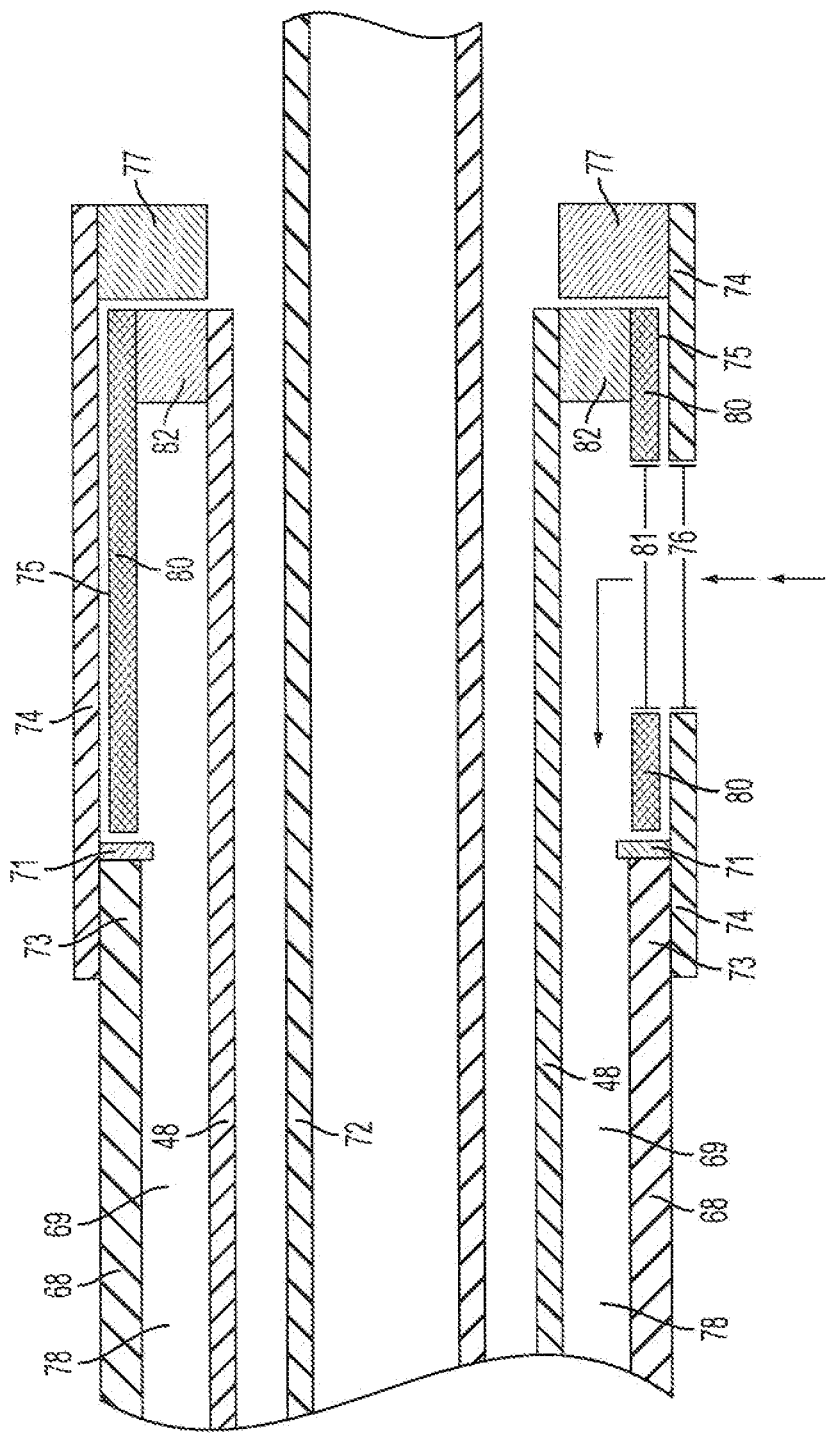
FIG. 6 is a partial, cross-sectional view of the macerator element the embodiment of FIG. 5.
Figure 7:
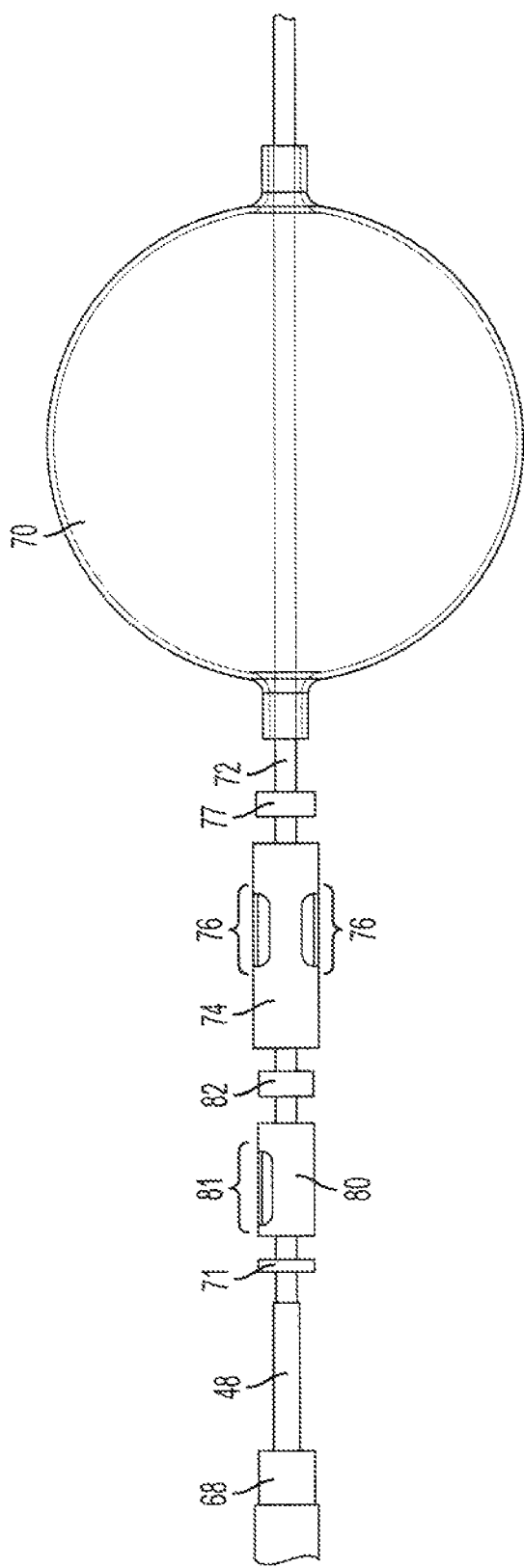
FIG. 7 depicts an assembly view of the distal portion of the device of FIG. 6.

The maceration element 30 of this embodiment consists of a stationary tubular extension 74 with a rotating shearing member 80 coaxially disposed within lumen 75 of the tubular extension 74, as seen in FIG. 6. The tubular extension 74 may be securely attached to the distal end 73 of the inner shaft 68 by conventional techniques such as, but not limited to, welding, adhesive bonding or step attachment and adhesive bonding. Tubular extension 74 includes either a single cut out 76 or a plurality of cut-outs formed by removing part of the sidewall of the tubular extension 74. The inner shaft 68 may be coaxially disposed within lumen 8 of an outer shaft 5 and extend along the entire length thereof to the proximal end (not shown) of the outer shaft 5. The inner shaft 68 may be moved independently of, or free from constraint, the outer shaft 5 so as to advance and/or retract the macerator element 30 while holding outer shaft 5 stationary. Alternatively, in another embodiment it is conceivable that inner shaft 68 is fixed relative to the outer shaft 5 so that the inner shaft 68 and outer shaft 5 move in unison.

A drive shaft 48 may be coaxially disposed within lumen 69 of the inner shaft 68 and extend therethrough to form an aspiration area 78 within the lumen 69 of the inner shaft 68. The shearing portion 80 may be coaxially disposed within the lumen 75 of the tubular extension 74 and securely attached to the distal end of the drive shaft 48 via an attachment member 82. The attachment member 82 may be secured to the distal end of the drive shaft 48 by conventional techniques such as, but not limited to, welding, adhesive bonding or step attachment and adhesive bonding. The shearing member 80 may be a tubular shape with a single cut-out 81.

A proximal collar 71 is used to prevent shearing member 80 from unwanted or unintended movement within lumen 69 of inner shaft 68. The proximal collar 71 may be either a bulge, protuberance, or extension of the inner wall of the tubular extension 74 or an additional element. Proximal collar 71 may be securely attached to the distal end of the inner shaft 68 or the inner wall of tubular extension 74. A distal collar 77 may be used to prevent the shearing member 80 from unwanted or unintended forward movement. The distal collar 77 may be either a bulge, protuberance, or extension of the inner wall of the tubular extension 74 or an additional element. The attachment member 82, proximal collar 71 and distal collar 77 may be made from metal or plastic and is secured by conventional techniques such as, but not limited to, welding, adhesive bonding or step attachment and adhesive bonding.

An external vacuum syringe or pump (not shown) may be attached to the clot removal device 1. The dislodged and broken-down clot material is aspirated by first entering through the cut outs 76 of the tubular extension 74, through the cut outs 81 of the shearing member 80, and finally enters the lumen 69 of the inner shaft 68 for removal from the body, as shown by arrows in FIG. 6.

Figure 8A:
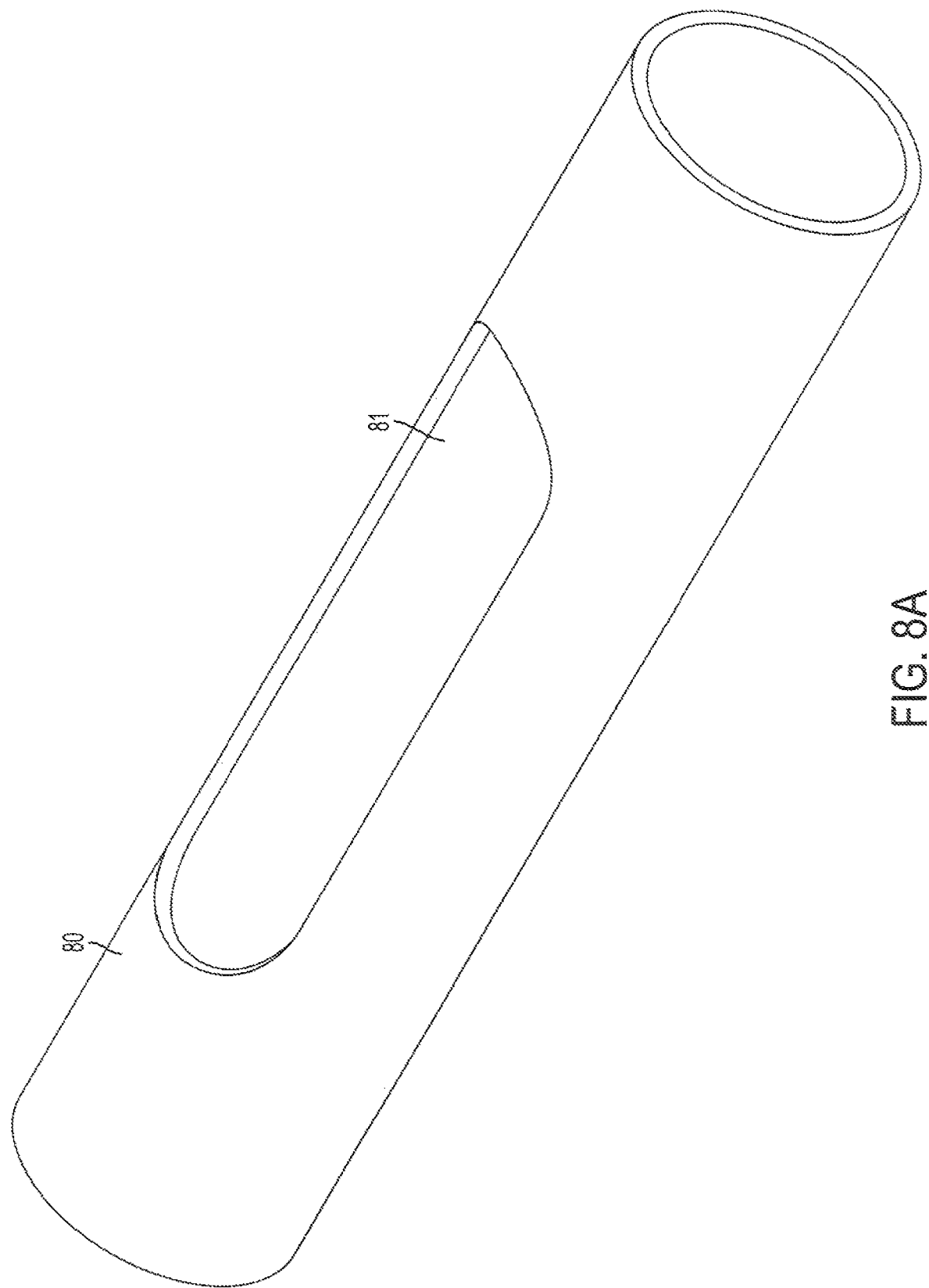
FIG. 8A is an isometric view of a rotatable shearing member.
Figure 8B:
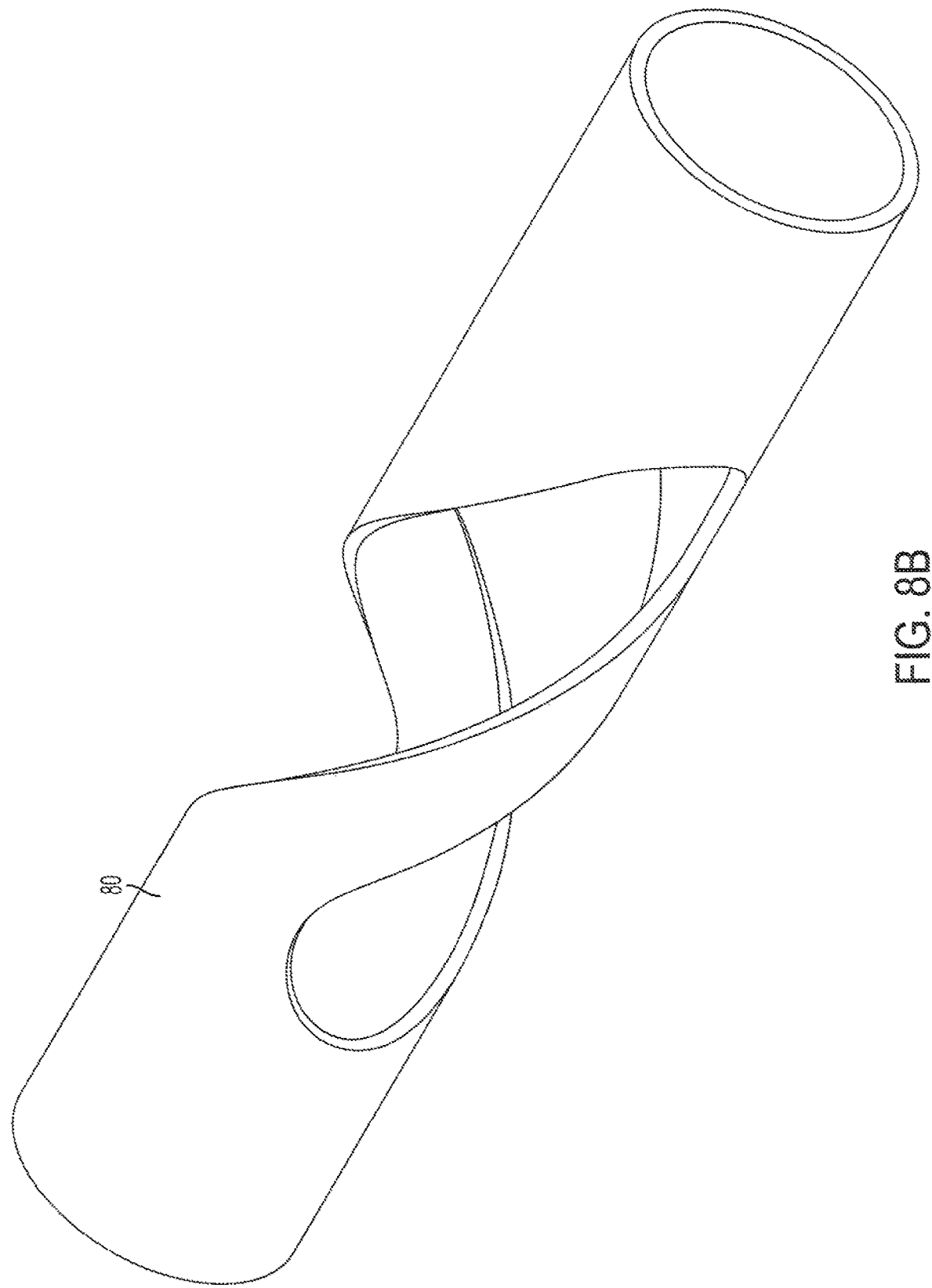
FIG. 8B is an isometric view of another embodiment of a rotatable shearing member.
Figure 8C:
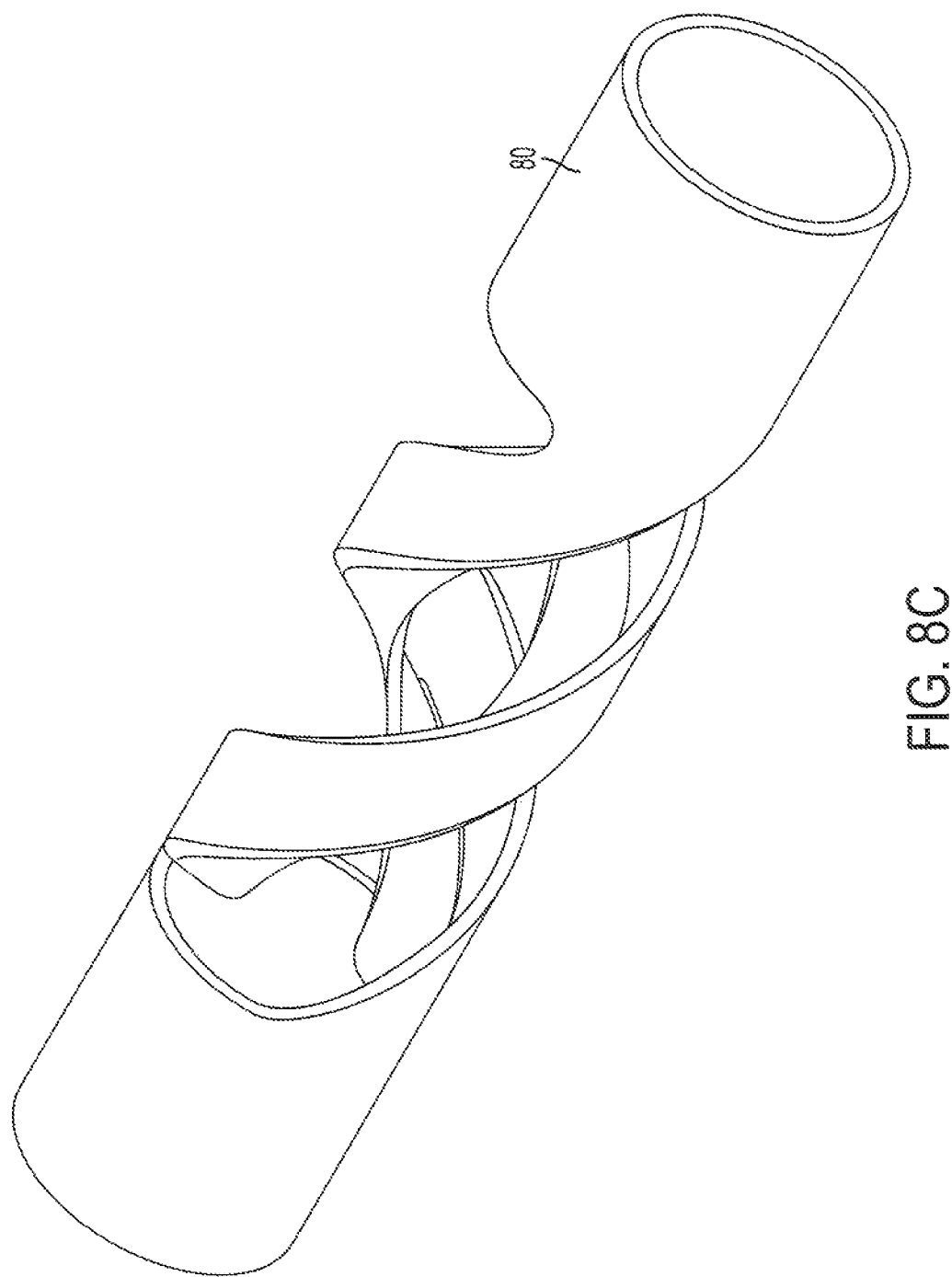
FIG. 8C is an isometric view of another embodiment of a rotatable shearing member.

The different embodiments of shearing portion 80 are seen in FIGS. 8A-8C. As seen in FIG. 8A the shearing member 80 may be a tubular shape with a single cut-out 81. Additionally, as seen in FIG. 8B-8C, the shearing member 80 may have multiple arrangements.

This embodiment may also comprise a distal occlusion element 70. Advantages of using distal occlusion element 70 include aiding in the removal of clot material and/or prevent unintended traveling or migration of dislodged clot material. The distal occlusion element 70 may comprise of either a compliant or non-compliant inflatable balloon, an embolic protection filter, an expandable wire filter, or other devices capable of expanding within vessel lumen.

The occlusion element 70 may be attached to an occlusion shaft 72 that is independent and freely movable within lumen 69 of inner shaft 68. Alternatively, occlusion shaft 72 may be securely attached to the distal end of the inner shaft 68 and move in unison together. The distal most end of the occlusion shaft 72 may comprise either a stiff end or a floppy tip end as known in the art.

Figure 10:
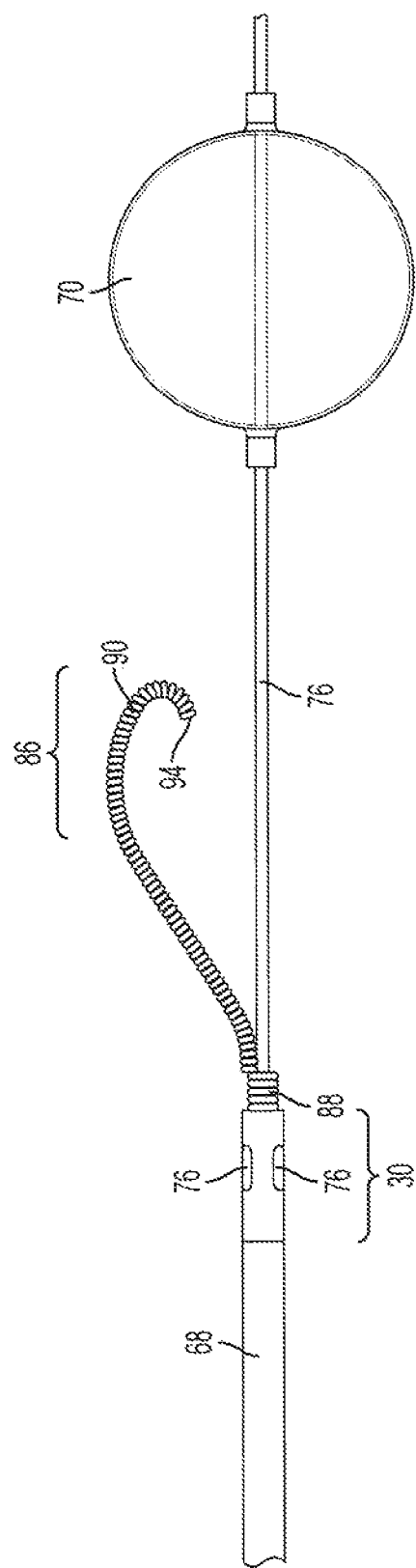
FIG. 10 is a partial side wide of a shearing macerator assembly with a rotating wire and a distal embolic protection element in the form of a balloon.
Figure 11A:
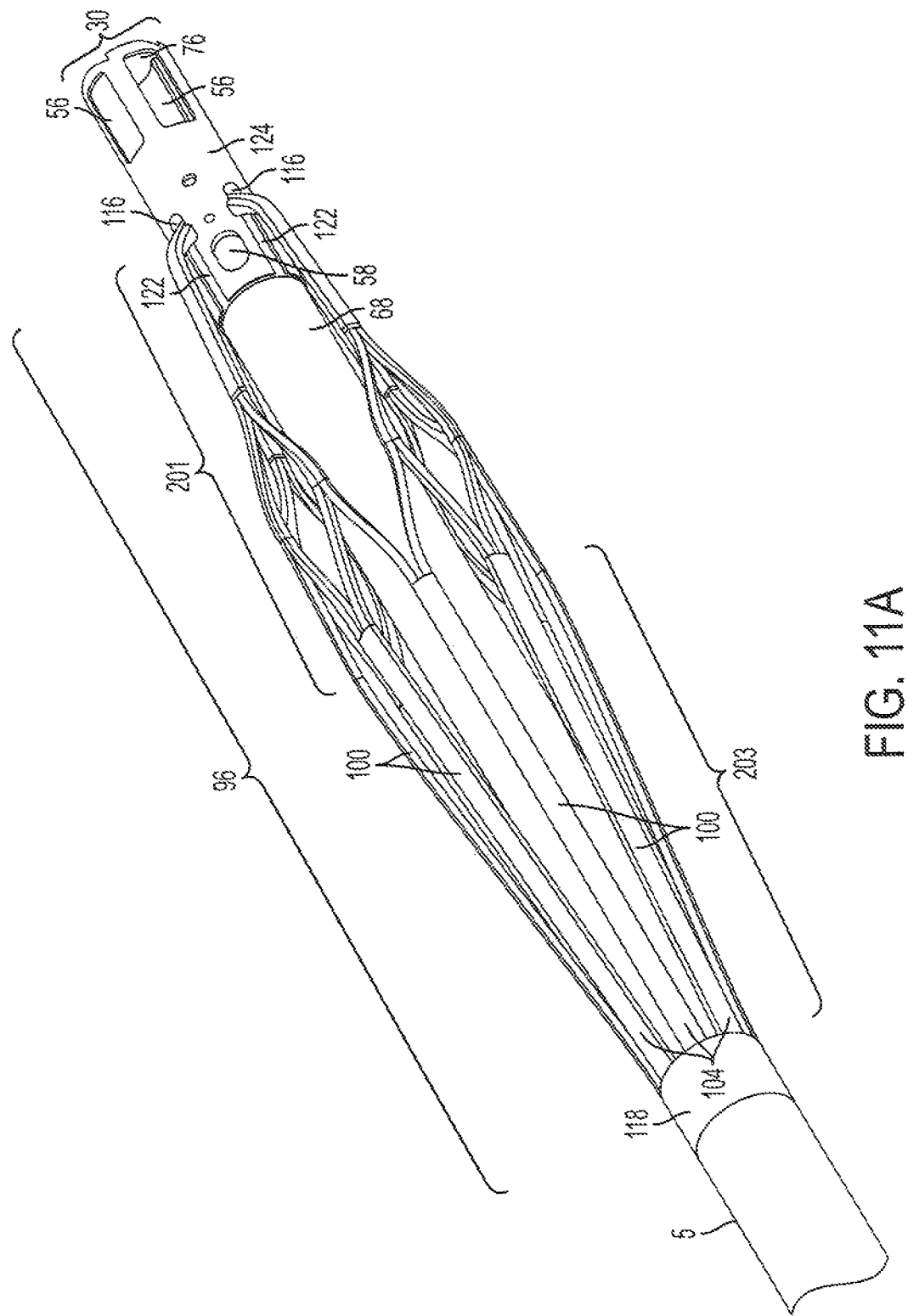
FIG. 11A depicts a partial, isometric view of the distal portion of the device illustrating a manually expandable cage in a retracted, undeployed position.
Figure 11B:
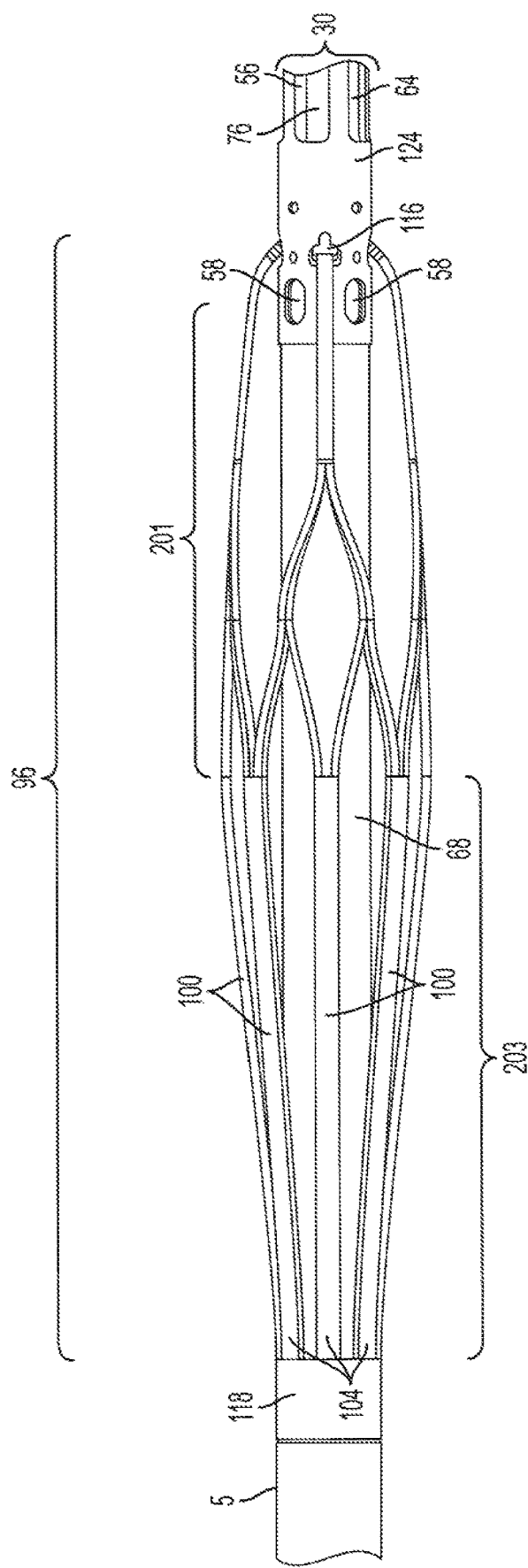
FIG. 11B is a partial, plan view of the distal portion of the device depicting the manually expandable cage in a retracted, undeployed position.
Figure 11C:
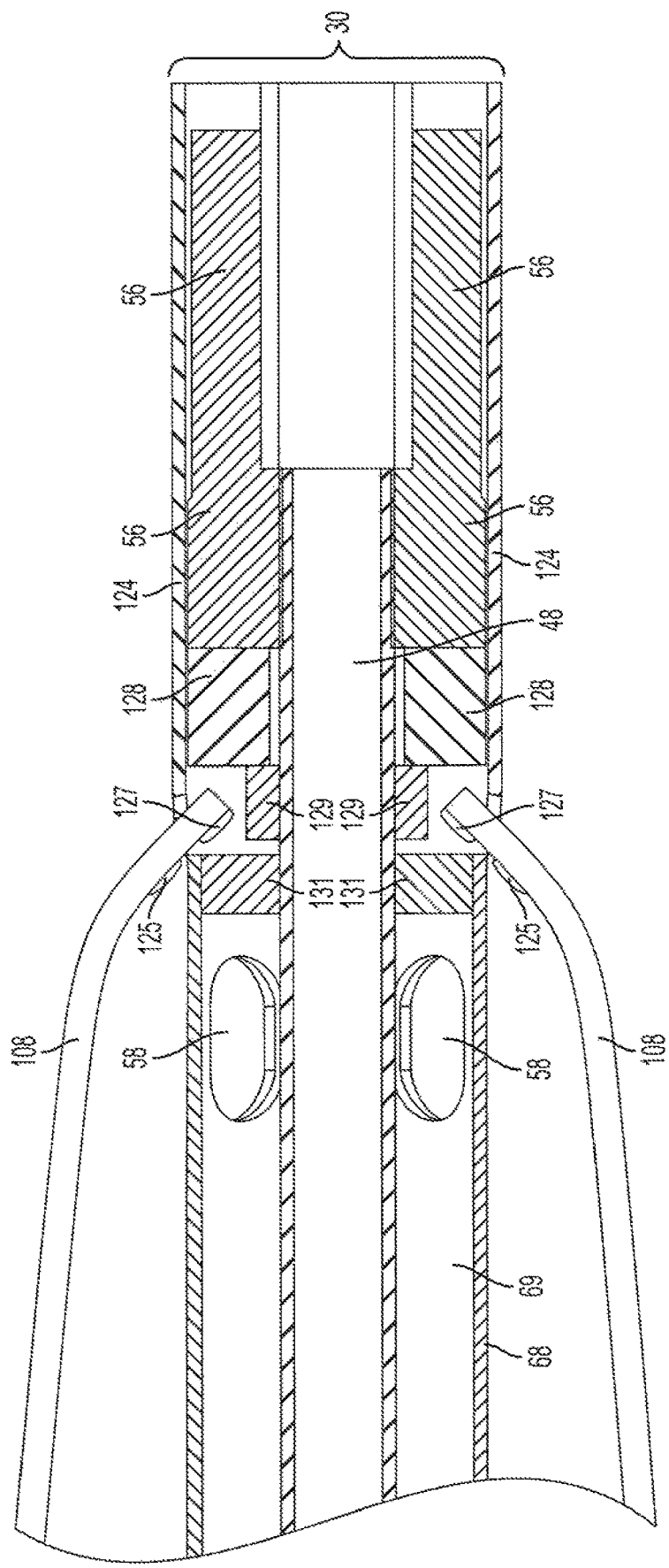

As seen in FIGS. 9-10, yet another embodiment of the device is shown. In this embodiment the clot removing device 1 is similar to what has been described and shown above but further includes a rotating wire 86 element. The rotating wire 86 element may be attached near the distal end of the drive shaft 48. An advantage of this embodiment is that as the wire 86 rotates, either clockwise or counterclockwise, it aids in breaking up and mechanically disrupting the material into smaller pieces. The rotating wire element 86 comprises a core 88 and an outer coil 90. The rotating wire 86 is coaxially attached to the device by securing the core 88 to the drive shaft 48 abutting the distal collar member 82. By securing the wire 86 to the drive shaft 48 the wire 86 will rotate at the same speed as the drive shaft 49 and shearing member 80.

The core 88 may be a solid piece of metal, such as stainless steel or nitinol, or plastic and coaxially or otherwise surrounded by an outer coil 90. The core 88 may be a single piece that has been laser cut, stamped, coiled, or compressed to form a predetermined shape. The outer coil 90 may be a solid piece of metal, such as stainless steel or nitinol, or plastic and securely attached to the core 88 via any known method of adhesion, such as welding, adhesives, or other securement means. An advantage of using an outer coil 90 to surround the core 88 is so the rotating wire 86 may have a "floppy tip" design, as known in the art, which aids in preventing damaging the vessel wall during rotation.

The wire 86 may comprise of many different shapes and size, including a straight design, coil, helix shape, or even circular. The distal occlusion shaft 72 may be coaxially disposed within the lumen of the drive shaft 48 therefore extending beyond the wire 86. The distal end 94 of the wire 86 may be independent and freely movable relative to the occlusion shaft 72 or alternatively the distal end 94 may be securely attached (not shown) to the occlusion shaft 72.

Figure 12A:
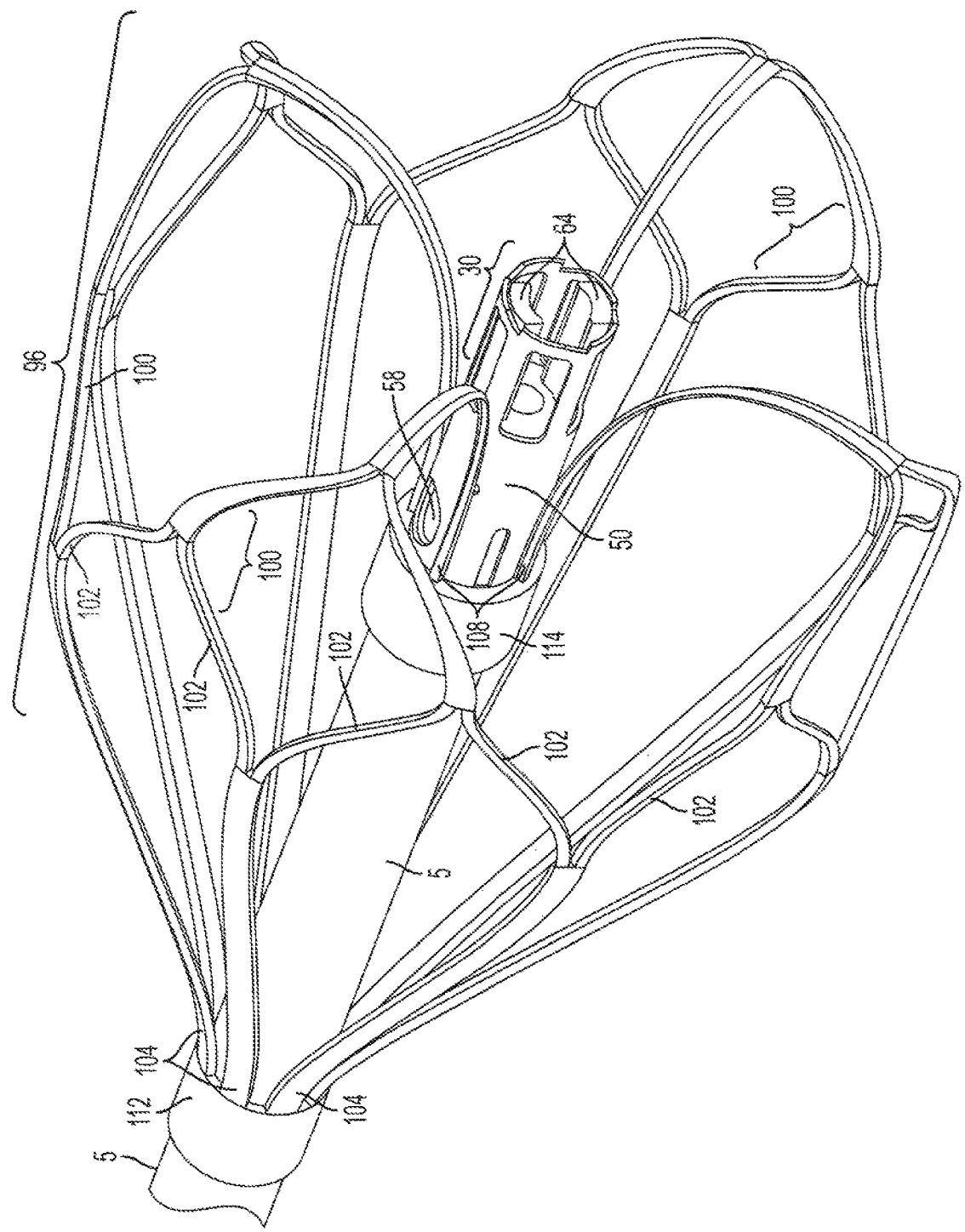
FIG. 12A is a partial, isometric view of the distal portion of the device illustrating an expandable cage in a deployed position.
Figure 12B:
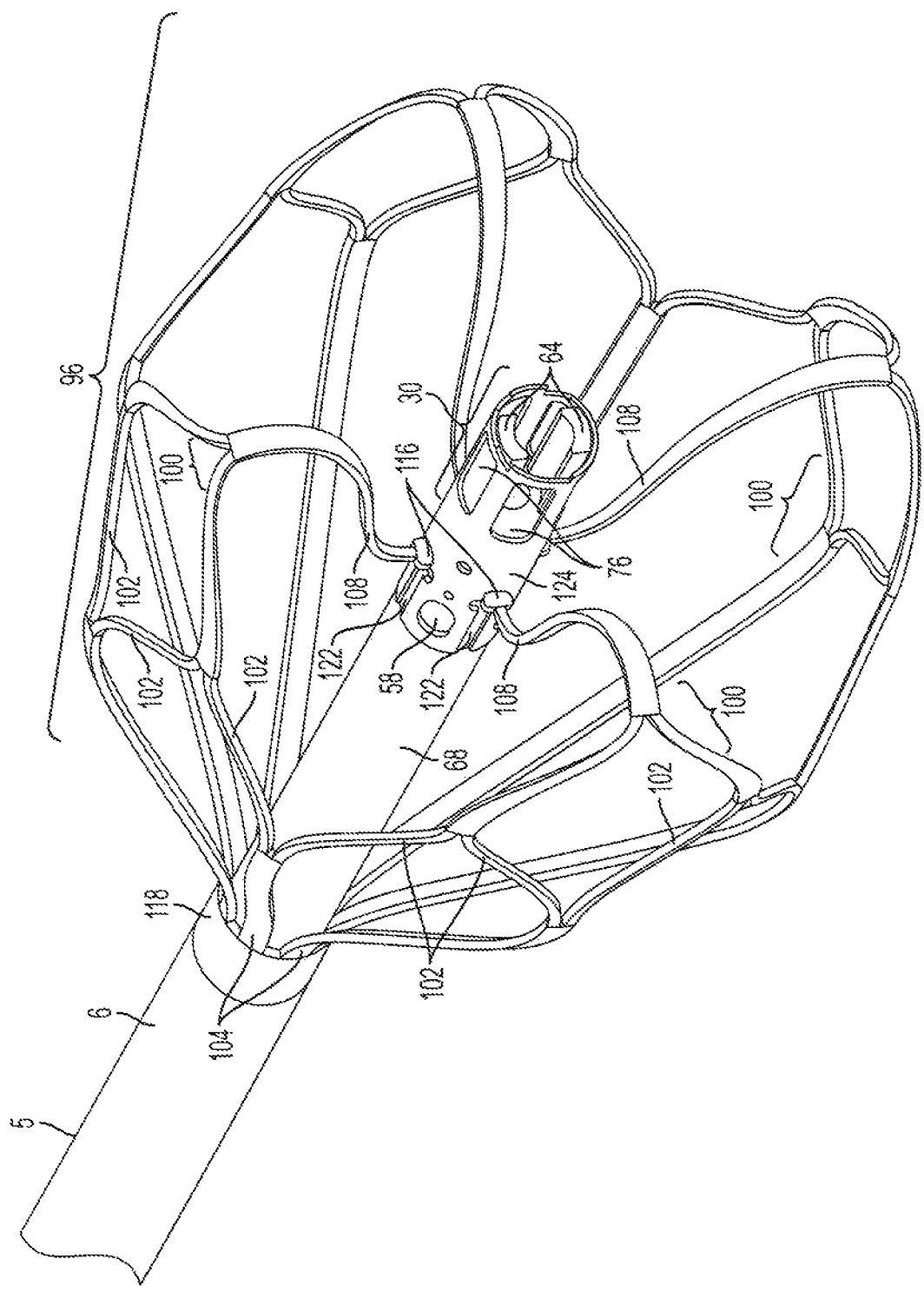
FIG. 12B is a partial, isometric view of the distal portion of the device illustrating a manually expandable cage in a deployed position.
Figure 12C:
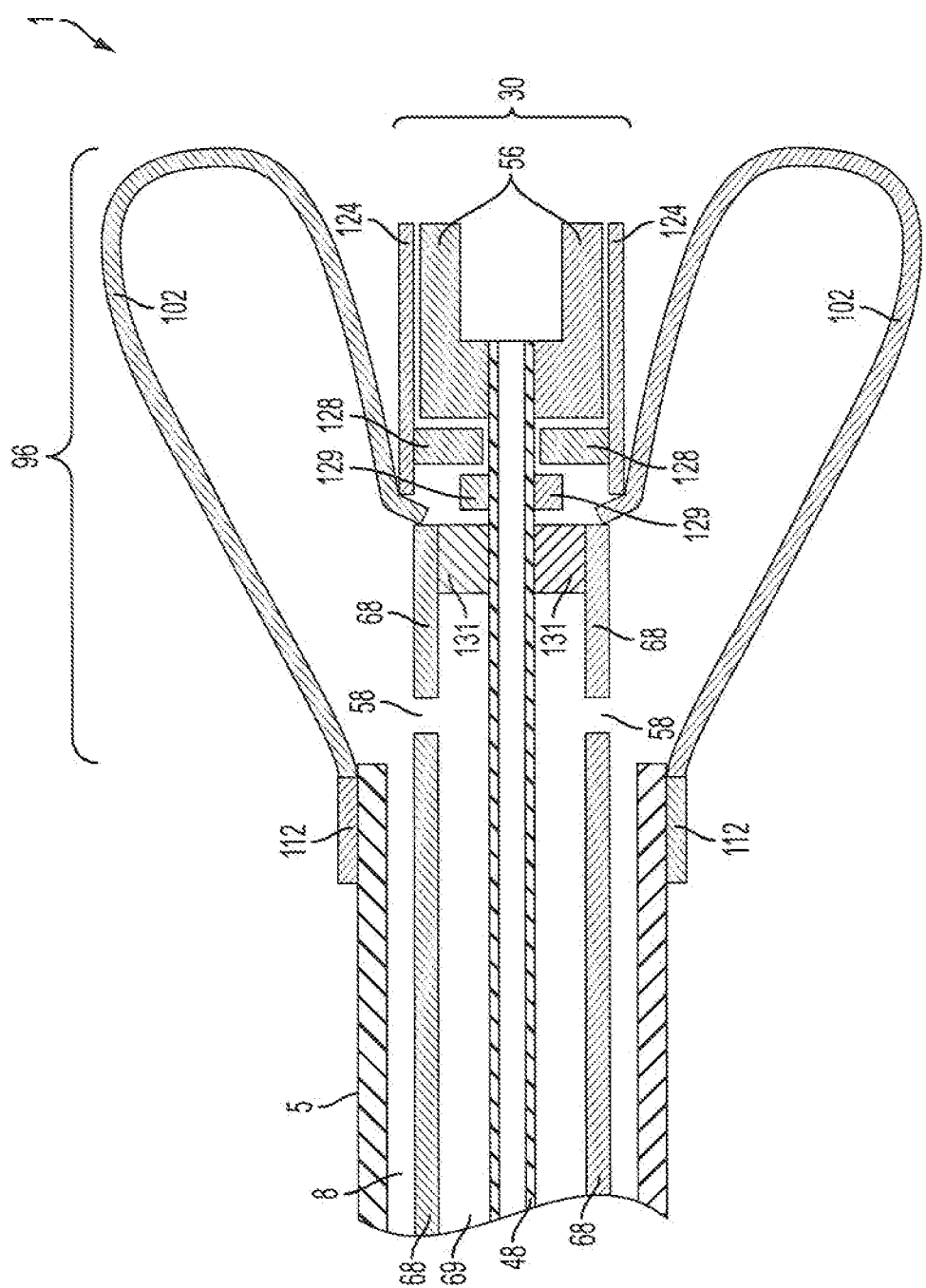
FIG. 12C illustrates an enlarged, cross-sectional view of the manually expandable cage section in a partially deployed position.
Figure 13:
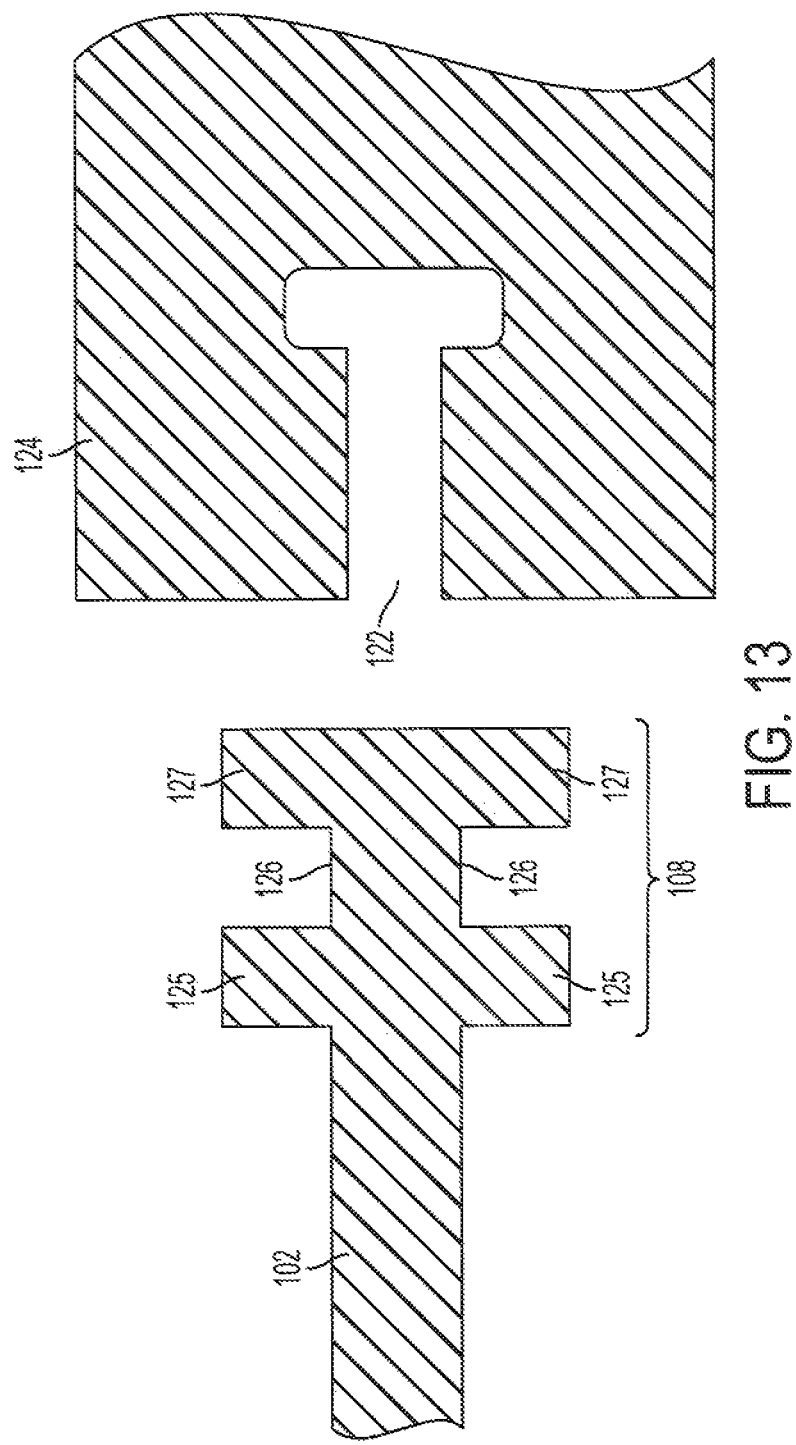
FIG. 13 is a further enlarged, cross-sectional view of the manually expandable cage section illustrating the position of the distal ends of the wire legs of the cage.

As seen in FIGS. 12A-13 yet another embodiment of the clot removal device 1 is shown. This embodiment of the clot removal device 1 is similar as to what was described above in FIG. 3-FIG. 4C, however in this embodiment the expandable member 12 element has been replaced with an inverted expandable centering element 96. An advantage of an expandable centering element 96 after it has become inverted or expanded, as described in more detail below, the apex of the centering element 96 may be parallel or in front of the distal most end of the macerator element 30. Another benefit of this embodiment is that when the device is used in tortuous anatomy the expandable centering element 96 will be less likely to catch, snag, engage, or rupture the vessel walls, and in turn promote advancement of the clot removal device 1. Yet another advantage of this embodiment is less chance for unwanted advancement or "snow plowing" of the clot material away from the macerator element 30. Clot removal device 1 for this embodiment may be in the range of a 6 F to 20 F in size so as to facilitate removal of clot from both small and large vessels.

The expandable centering element 96 is attached to the clot removal device 1 via an secured attachment 116. The secured attachment 116 provides the user the ability to manually expand or invert the expandable centering element 96. For this embodiment the outer shaft 5 coaxially surrounds and is freely moveable relative to the inner shaft 68. An advantage of this embodiment is that during placement of the clot removal device 1 the expandable centering element 96 may be collapsed, pulled taut, or "non-inverted", as seen in FIG. 12A-12C. A non-inverted or collapsed expandable centering element 96 may facilitate advancement, placement, adjustment during use, or removal of the device 1. When expandable centering element 96 is in the non-inverted or collapsed position the proximal bulge 125 of the secured attachment 116 is pulled taut and toward the proximal end of the device, as shown in FIG. 12C. Conversely, when the expandable centering element 96 is in the inverted or expanded position the proximal bulge 125 of the secured attachment 116 is pushed toward the distal end of the device, as seen in FIG. 13B.

The user may manually "invert" or expand the centering element 96 so the apex of the expandable centering element 96 may be parallel or slightly proximal of the macerator element 30, as seen in FIG. 12B-12C. The expandable centering element 96 may be inverted or expanded by holding the outer shaft 5 stationary and retracting the inner shaft 68 or holding the inner shaft 68 stationary and advancing outer shaft 5.

In this embodiment the proximate end 104 of each converging wire member 102 may be attached to the distal end 6 outer shaft 5 via an outer shaft collar 118. The wire members may be made from a shape memory material such as nitinol, or other material such as stainless steel or plastic. The distal ends 108 of the wire members 102 may be securely attached to the distal end of the inner shaft 68 via a secured attachment 116. The secured attachment 116 allows for distal and proximal movement of the distal ends 108 of the wire members 102 while securely coupling the distal bulge 127 of each wire member 102 within the empty space abutting the distal end of the inner shaft 68.

The macerator element 30 of this embodiment comprises of an outer tubular extension 124 having either a single cut out 76 or slot or a plurality of cut-outs or slots and rotating finger elements 56. Extending coaxially along the lumen 69 of inner shaft 68 is the drive shaft 48 with its distal end securely attached to rotating finger elements 56 via a press fit, or interference fit. Alternatively, other macerator elements described above may be used in combination with the inverted expandable centering element 96, such as the rotating member 64, shearing member 80, auger 32, or rotating wire 86.

To prevent the drive shaft 48 from unwanted forward or backward movement a proximal stopper 131 and distal stopper 128 are used in combination with crimp tube 129. The proximal stopper 131 abuts the distal most end 123 of the inner shaft 68 and is securely attached to tubular extension 125 via conventional techniques such as, but not limited to, welding or adhesive bonding. The proximal stopper 131 may be an additional element attached to inner wall of inner shaft 68 or a bulge, protuberance, or extension of the inner wall of the inner shaft 68. The crimp tube 129 may be crimped or securely attached to the drive shaft 48 at a position between the proximal stopper 131 and distal stopper 128. The distal stopper 128 may be attached to the tubular extension 124 via conventional techniques such as, but not limited to, welding or adhesive bonding, at a selected distance distal from the end of the crimp tube 129. The proximal stopper 131 may be an additional element attached to inner wall of the tubular extension 124 or a bulge, protuberance, or extension of the inner wall of the tubular extension 124. The proximal stopper 131, distal stopper 128 and crimp tube 129 may be made from hypo-tubing, metal, plastic, or other suitable material. In use, the crimp tube 129 is enclosed between the proximal stopper 131 and distal stopper 128 in order to prevent the drive shaft 48 from unintentionally advancing or retracting within lumen 69 of inner shaft 68.

The tubular extension 124 is securely attached to inner shaft 68 via conventional techniques such as, but not limited to, welding or adhesive bonding. An aspiration area 58 is created by drilling a hole through tubular extension 124 and inner shaft 68 near the distal end of the macerator shaft 68. This aspiration area 58 creates an open channel or hole from the lumen 69 of the inner shaft 68 through the body of the shaft 68 and tubular extension 124. In use, the user may elect to apply suction or vacuum through the lumen 69 of the inner shaft 68 which may create a vortex within the vessel and aspirate clot material through aspiration area 58.

As seen in FIG. 13 distal ends 108 of the wire members 102 may have a proximal bulge 125, a groove or notch 126, and a distal bulge 127, creating an "H" shape at the distal end 108. The tubular extension 124 may comprise slits 122 along the proximal end. The number of slits 122 correspond with the number of distal ends 108 requiring securement via the secured attachment 116. Prior to attaching tubular extension 124 to inner shaft 68 the notch 126 of the distal end 108 of the wire member 102 is slid into the slits 122 on the proximal end of the tubular extension 124. The tubular extension 124 is then securely attached to the distal end of the inner shaft 68 by conventional techniques such as, but not limited to, welding or adhesive bonding. After tubular extension 124 is securely attached to inner shaft 68 the secure attachment 116 is created because the distal bulge 127 will be securely enclosed within the empty space abutting the distal end of the inner shaft 68 while the proximal bulge 125 will be located and freely movable atop the tubular extension 124. The notch 126 will be enclosed between the distal end of the inner shaft 68 and the slit 122 of the tubular extension 124.

As seen in FIG. 12A, yet another embodiment of the inverted expandable centering element 96 is shown. The proximal end 104 of each wire member 102 may be securely attached to the outer shaft 5 at a proximal collar 112. The distal ends 108 of each wire member 102 are securely attached to the outer shaft 5 at a distal collar 114. In this embodiment, the distance between proximal collar 112 and distal collar 114 is fixed. Clot removal device 1 may be in the range of a 6 F to 20 F in size so as to facilitate removal of clot from both small and large vessels. The proximate collar 112 is securely attached to the outer shaft 5 via conventional techniques such as, but not limited to, adhesive bonding. The distal ends 108 of the wire members 102 may be inverted, meaning bent inward towards the shaft 5 and then back towards the proximal collar 114, and securely attached to the outer shaft at a distal collar 114. The distal collar 114 may be securely attached to the inner shaft 68 via conventional techniques such as, but not limited to, adhesive bonding. Alternatively, if no inner shaft 68 is used then the distal collar 114 may be securely attached to distal end of the outer shaft 5.

Other attachment configurations are also possible, such as attaching the distal ends 108 of the wire members 102 at the same position along the distal end 6 of the outer shaft 5. Further, the wire members 102 of the expandable centering element 96 may be made of a number of different materials capable of expanding to a pre-determined shape, such as stainless steel or nitinol.

In use the clot removal device 1 may be introduced into the target vessel or other anatomical site using minimally invasive access techniques known in the art. If a distal occlusion element 70 is being used in combination with the device 1 the user may elect to place the occlusion element 70 using known techniques in the art prior to insertion of the device 1. Once the distal occlusion element 70 has been properly inserted and placed beyond the clot, the device 1 may be backloaded over a pre-placed guidewire. Alternatively, the user may elect to insert the device 1 at the target area and then insert the distal occlusion element 70 into through lumen of the drive shaft 48.

During insertion the expandable member 12 or expandable centering element 96 may be collapsed within a procedure sheath to aid in advancement and placement of the device 1. The clot removal device 1 may be advanced into position adjacent the clot. The procedure sheath may be retracted, or the device 1 may be advanced holding the sheath stationary, allowing for automatic deployment of the expandable member 12 or expandable centering element 96, or manual expansion of the expandable member 12 or expandable centering element 96 may be done by the user if required.

Placement and expansion of the expandable member 12 or inverted expandable centering element 96 centers the macerator element 30 of the clot removal device 1 within the vessel lumen. An advantage of centering the clot removal device 1 within the vessel lumen is that the macerator element 30 will be less likely to engage, damage, rupture, or puncture the vessel wall. Another advantage of centering the macerator element 30 is the decrease in likelihood of clogging or disrupting the movement of the macerator element 30. Once fully expanded, the expandable member 12 or expandable centering element 96 may either be held stationary during use or may be advanced toward the clot mass to aid in the removal of clot material.

After the macerator element 30 and distal occlusion element 70 are in place the drive shaft 48 may be activated. The speed and rotation of the drive shaft 48 will depend on the type of macerator element 30 being used and the requirements of the treatment. Activation of the drive shaft 48 may cause either clockwise or counterclockwise rotation of macerator element 30. Upon activation of the drive shaft 48 and rotation of the macerator element 30 the material for removal, such as a clot, will start to macerator, break down, separate, chop, or remove clot from the vessel.

Although the current design anticipates disruption of the clot material without the use of a lysing agent, a practitioner may optionally consider the use of a lysing agent in combination with the use of the device 1 at any time during the procedure. The device and method for introducing the lysing agent may be at the discretion of the practitioner. However, if a practitioner elects to use the clot removal device 1 in combination with a lysing agent or other drug this fluid may be introduced into the through lumen 8 of the outer shaft 5 or through the lumen 68 of the inner shaft 68 and injected into the vessel.

Once the clot has been significantly broken down into smaller pieces and removed through aspiration or vacuum, the distal occlusion element 70 may be retracted toward the expandable member 12 or expandable centering element 96 to aid in the capture of any loose clot fragments and disengagement of any clot mass remaining attached to the vessel wall. The essentially smaller clot particles and the liquefied clot material disposed within the lumen 69 of the inner shaft 68 may be fully removed from the vessel to a location external of the clot removal device 1.

Upon completion of the procedure, the distal occlusion element 70 and macerator element 30 may be retracted within the through lumen 8 of the outer shaft 5, or optionally through a procedure sheath if no outer sheath 5 is being used. The expandable member 12 or expandable centering element 96 may then be retracted within the procedure sheath thereby removing any potentially remaining clot particles may be captured in the expandable member 12 or expandable centering element 96. The clot removal device 1 may then be withdrawn from the patient. This method contemplates clot disruption and removal with minimum risk of injury to the vessel.

Figure 14:
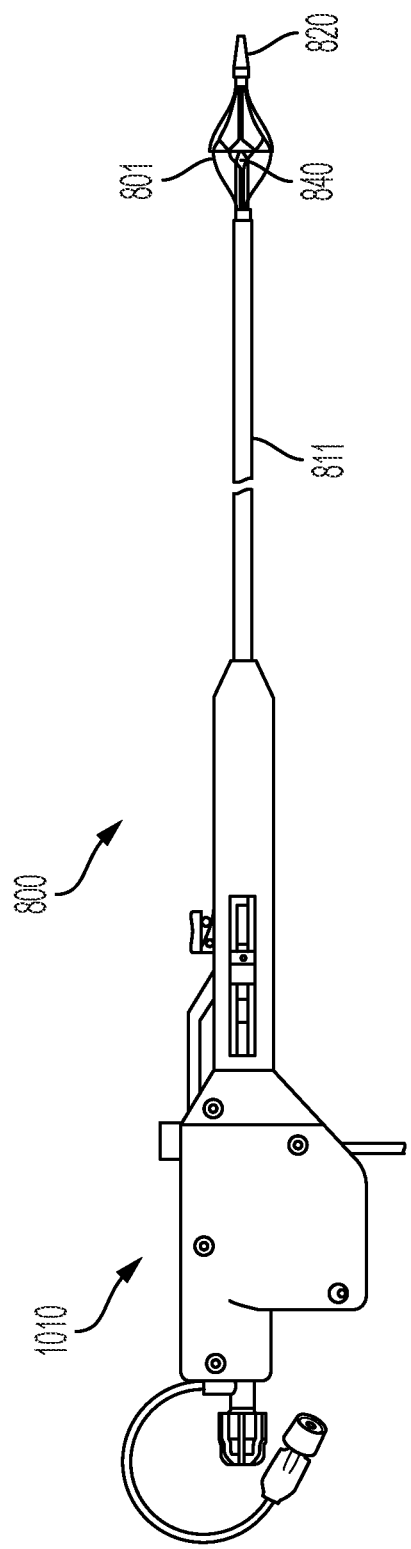
FIG. 14 illustrates a plan view of another embodiment of a device for the removal of undesirable material from an anatomical structure.

Another embodiment of the clot removal device 800 is shown in FIG. 14-FIG. 24. FIG. 14 illustrates clot removal device 800 which is comprised of a handle 1010, an elongated body 811, an expandable centering cage 801 disposed near the distal end of the elongated body, a macerator assembly 840 and a leading distal tip 820. During insertion of clot removal device 800, expandable centering cage 801 is in a compressed position within a slidable sheath. Once positioned in the desired anatomical location, the sheath is retracted to deploy cage 801 in an expanded position as shown in FIG. 14. The device may include a motor (not shown) attachable to the proximal section of handle 1010 for rotating a drive shaft 805 in connection with a macerator assembly 840, as will be described in more detail below. As with the other embodiments described herein, clot removal device 800 may be used to mechanically dislodge, disrupt, liquefy, break down and remove a clot, thrombus or other build-up of material formed within and against a vessel wall.

Figure 15:
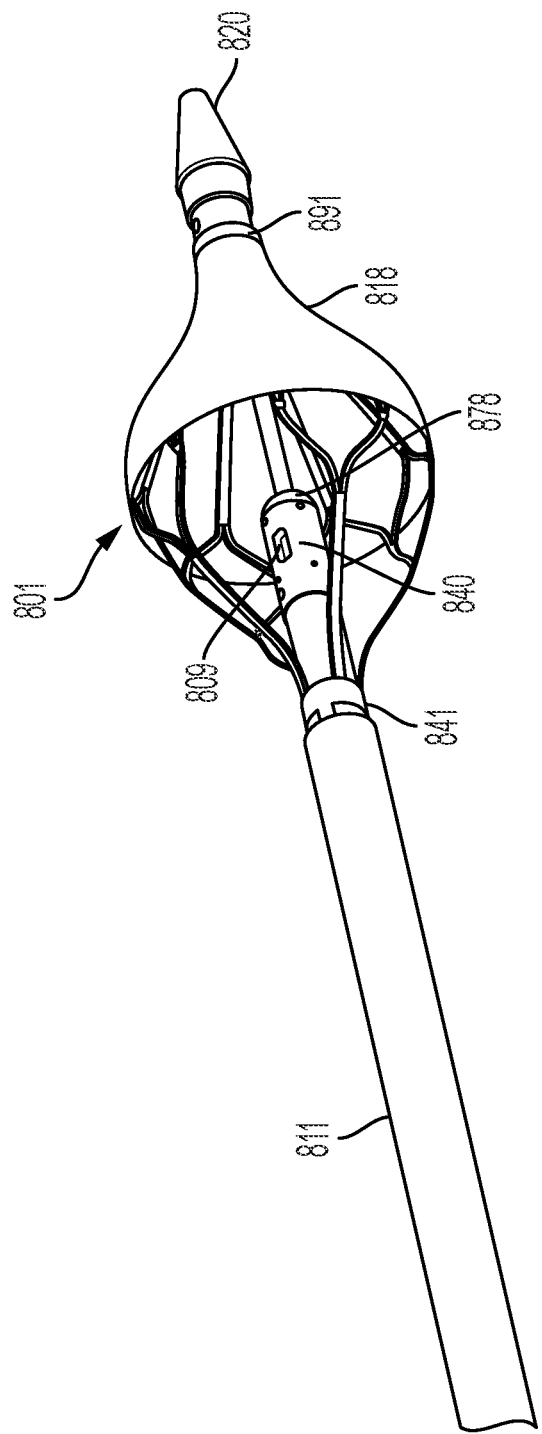
FIG. 15 is a partial, isometric view depicting the distal portion of the device of FIG. 14 with the expandable centering element and macerator.
Figure 16:
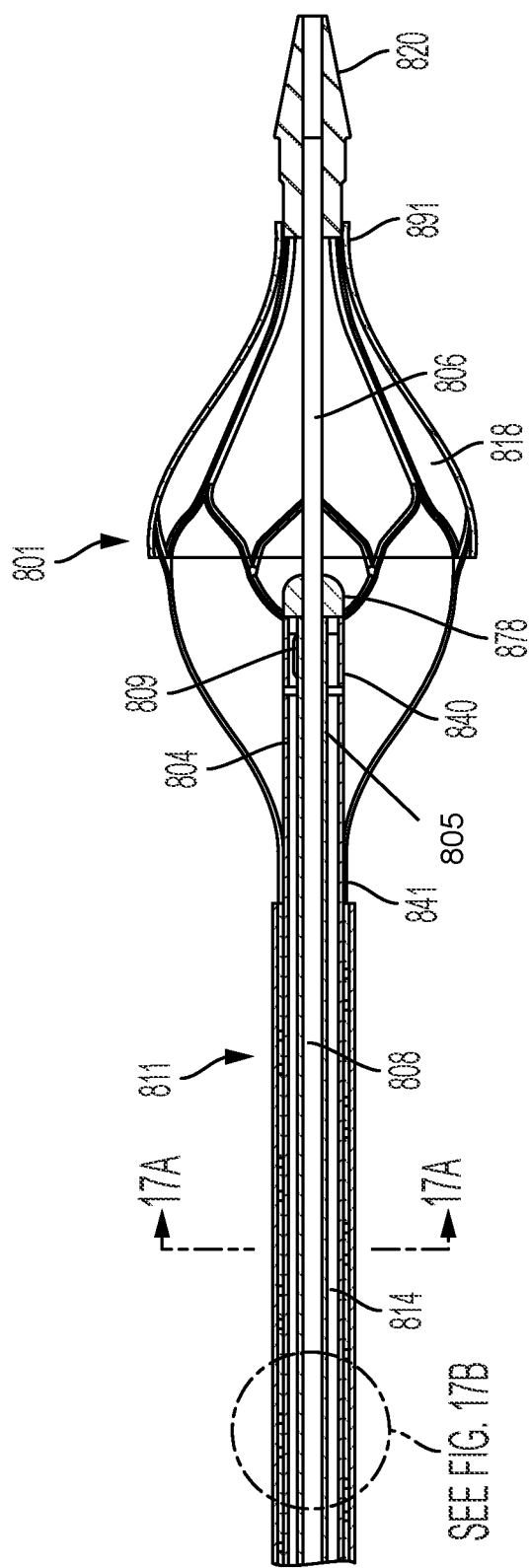
FIG. 16 is a partial, longitudinal cross-sectional view of FIG. 15.
Figure 24:
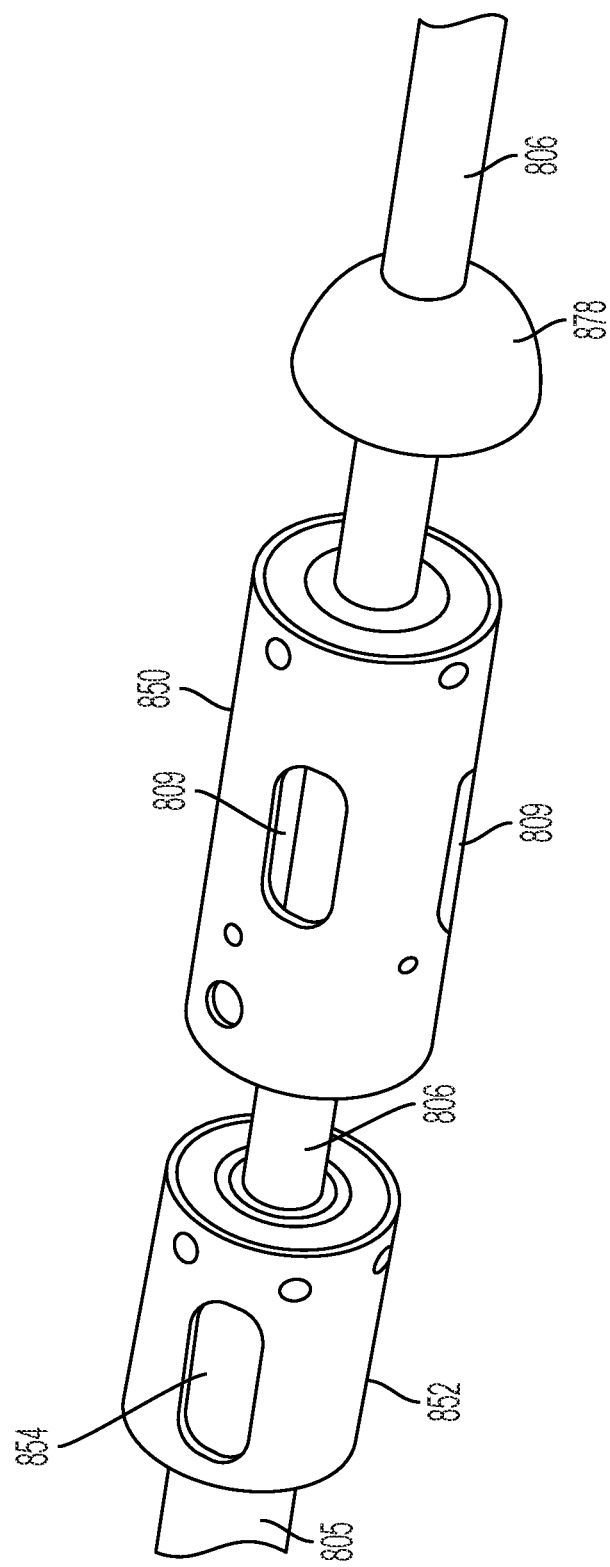
FIG. 24 illustrates an embodiment of the macerator assembly shown from an isometric view.

FIGS. 15 and 16 depict isometric and cross-sectional views of the distal portion of the device of FIG. 14 showing details of elongated body 811, expandable centering cage 801 and shearing rotating macerator 840. The device includes a leading distal tip 820 connected to the distal portion of the expandable centering cage 801 via distal collar 891. The expandable centering cage 801 also includes a proximal collar 841 which is connected to a cage control tube 803, as will be described in more detail with reference to FIG. 18. A cover film 818 is positioned over a distal portion of expandable centering cage 801. Macerator assembly 840 is shown positioned within the expandable centering cage 801. Macerator assembly 840 includes a one or more shearing windows 809 and a macerator terminating cap 878, as shown in FIG. 24.

Centering the macerator assembly 840 within the self-expanding centering cage 801 and providing the device with a leading distal tip 820 reduces the risk of inadvertent damage or perforation of the vessel wall during advancement and retraction of the device through the vessel. Specifically, the expandable centering cage 801 provides a barrier between the vessel wall and the cutting portion of the macerator 840 in both the expanded and compressed configurations. The cover film 818 acts as a clot and debris-retaining mechanism, isolating the clot mass from free-flowing blood. It also provides a smooth outer surface to reduce the likelihood of inadvertent vessel wall damage.

Figure 17B:
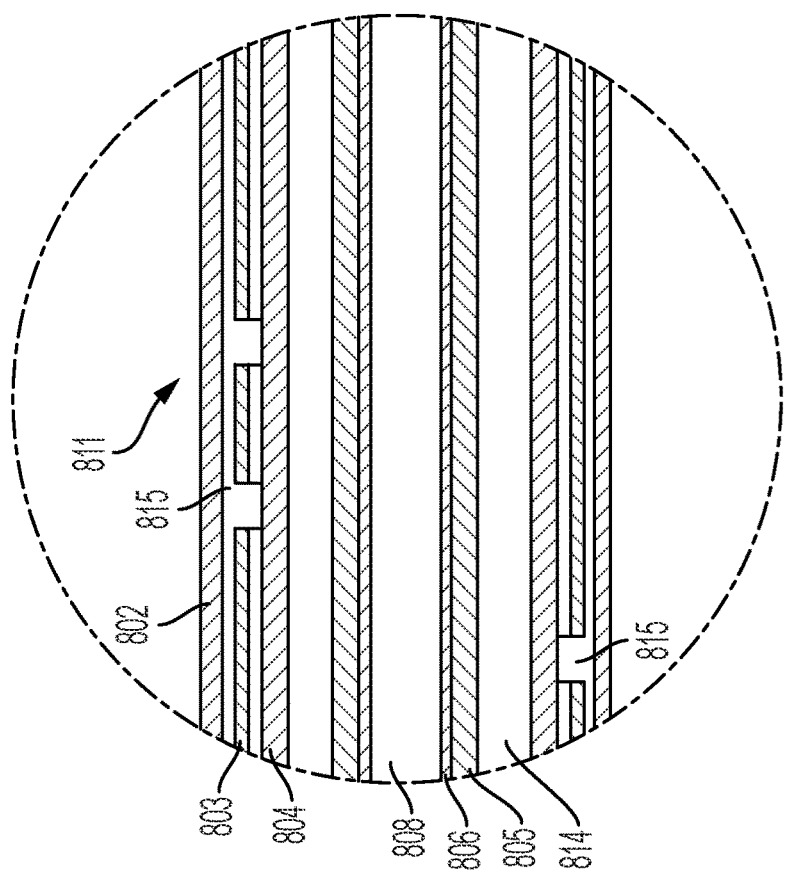
FIG. 17B is an enlarged longitudinal cross-sectional view of the elongated body section shown in FIG. 16.
Figure 17A:
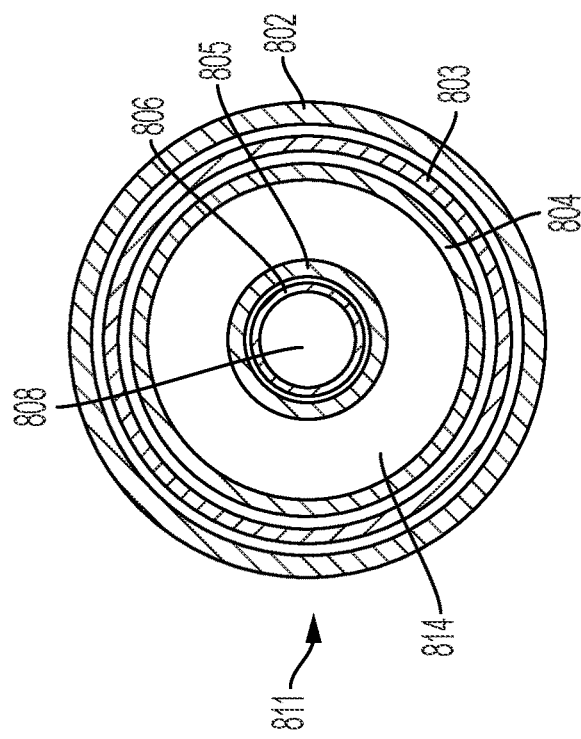
FIG. 17A is enlarged cross-sectional view of the elongated body taken along lines 17A-17A of FIG. 16.

FIG. 17A illustrates enlarged cross-sectional view of the device's elongated body 811 taken along lines 17A-17A of FIG. 16. FIG. 17B illustrated an enlarged longitudinal cross-sectional view of the device's elongated body shown within circle 17B of FIG. 16. As shown, elongated body 811 is comprised of slideable outer sleeve 802 coaxially surrounding a proximal cage control tube 803, a main catheter shaft 804, and a hollow drive shaft 805 positioned within the main catheter shaft 804. An aspiration lumen 814 is thus formed in the coaxial space between inner wall of shaft 804 and the outer wall of drive shaft 805. Coaxially positioned within the drive shaft lumen is a guidewire receiving tube 806, having a guidewire lumen 808. Guidewire receiving tube 806 extends distally past the end of elongated body 811, macerator assembly 840, through the expandable centering cage 801, terminating within the leading distal tip 820 of the device, as most clearly shown with reference to FIG. 16.

The outer sleeve 802 is capable of being retracted or advanced via an activation mechanism 1011 on the handle 1010 (shown in FIG. 18) of the device to either expand or collapse the expandable centering cage 801. The cage sizing element 1012 on handle 1010 is in connection with proximal cage control tube 803 and may be manipulated to change the maximum expanded diameter of the expandable centering cage 801. This feature may be advantageous in that a single device may be used in vessels of different diameters as well as a single vessel which vary in diameter in the target treatment area. The cage control tube 803 extends from the handle 1010 to a proximal collar 841 of the expandable centering cage 801 where the distal end of tube 803 is securely attached to the proximal collar 841, as shown more clearly in FIG. 15 and FIG. 16. Control tube 803 may include a series of cutouts 815, shown in FIG. 17B, which positioned in a predefined pattern along working length of control tube 803. Cutouts 815 impart additional flexibility to proximal cage control tube 803 to improve trackability through the vessel as the device 800 is advanced and retracted.

The main catheter shaft 804 is coaxially positioned within the cage control tube 803 lumen and extends distally beyond distal end of tube 803, where it is coupled to the macerator assembly 840. As shown in FIG. 16 and FIG. 24, macerator assembly 840 is coupled to the distal end of catheter shaft 804. Macerator assembly 840 terminates in a macerator termination cap 878, which fluidly seals the distal end of the aspiration lumen 814. The maceration element 840 of this embodiment may consists of a stationary outer macerator sleeve 850 coaxially surrounding an inner macerator sleeve 852. Other maceration configurations are also contemplated. Macerator assembly 840 provides both a shearing function and an entry point for clot fragments to be pulled into aspiration lumen 814.

Outer macerator sleeve 850 may include one or more shearing windows 809, (as shown in FIG. 15). In one embodiment sleeve 850 comprises three shearing windows 809. Inner macerator sleeve 852 is comprised of a single shearing window 854. The drive shaft 805 extends from a motor through the elongated body 811 and terminates within the macerator assembly 840 distal of outer macerator shearing windows 809. When activated, the motor may be capable of rotating the drive shaft 805 up to 10,000 RPMs (rotations per minute) in either a clockwise or counterclockwise direction. Because the inner macerator sleeve 852 is attached to the drive shaft 805, it also rotates. Suction may be used to draw a portion of the clot through the outer shearing window 809 of the stationary outer macerator sleeve 850, where it sheared by the rotating action of the inner macerator sleeve 852. When the inner shearing window 854 comes into alignment with one of the plurality of outer shearing windows 809, the clot fragment created by the shearing motion is drawn into the aspiration lumen 814 for removal from the patient. Having only one inner shearing window 854 ensures that the alignment of the inner and outer window creates only one fluid flow channel to the catheter lumen and that channel is formed at the location of the sheared clot segment. Thus, free flowing blood surrounding the clot is not inadvertently aspirated into the catheter aspiration lumen 814.

In one embodiment, the motor may be capable of generating a rotation speed of 2000 to 4000 RPMs. The combination of the independently moveable macerating element 840 and shearing windows 809 are sufficient to disrupt the clot mass without the need to create a vortex flow as previously described. Accordingly, lower rotation speeds may be used to remove clot. Having a lower rotation speed has several advantages. The motor may be battery-powered, thereby resulting in a less expensive, single-use, disposable device design. A device operating at higher rotation speeds requires a more robust handle design comprised of components that can withstand higher friction and heat levels generated by the speed of rotation. Less heat and friction will be generated at lower speeds, thereby allowing the use of lightweight, less expensive device components.

Figure 18:
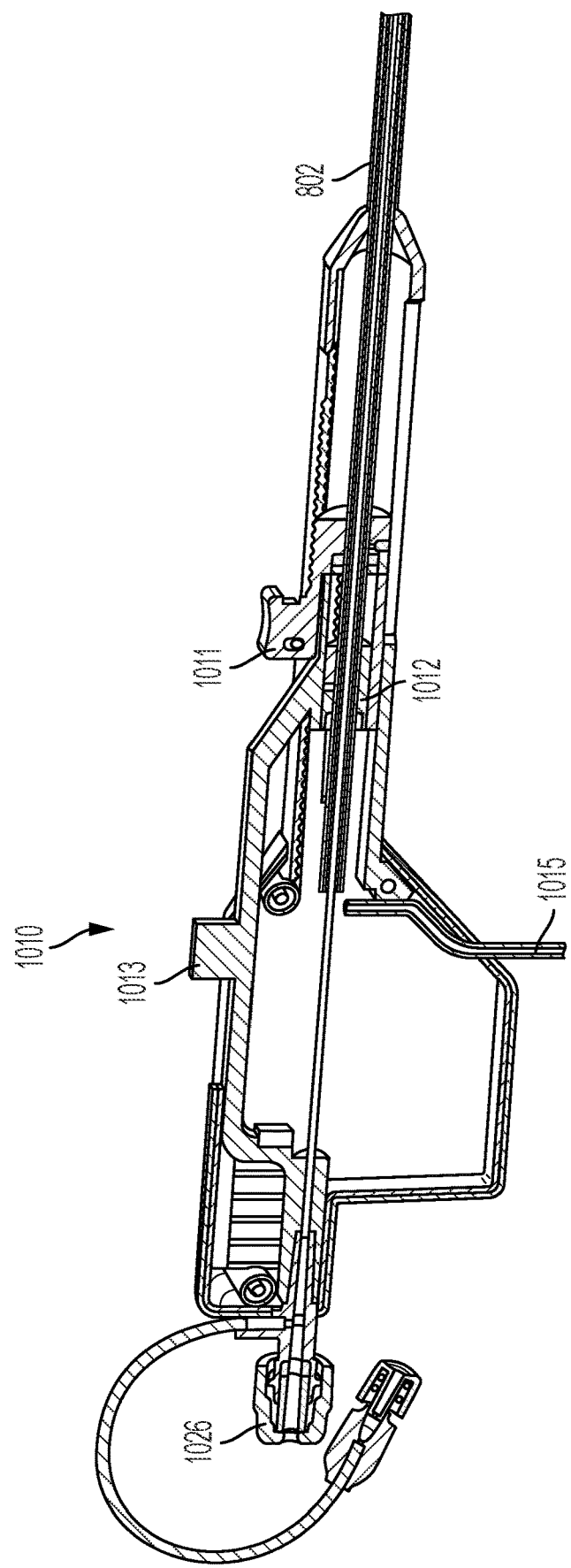
FIG. 18 is an isometric, partial cross-sectional view of an embodiment of the handle portion of the device.

FIG. 18 depicts one embodiment of the proximal handle 1010 of clot removal device 800. Some elements within the handle 1010 have been removed for clarity purposes. As shown, handle 1010 includes an activation element 1011 which controls movement of an outer sleeve 802, a cage sizing element 1012 which is connected control tube 803 and controls the diameter of expandable centering cage 801, and a macerator positioning element 1013 which may be used to adjust the position of the macerator assembly 840 relative to the expandable centering cage 801, as will be described in detail with reference to FIG. 21A-21C. The handle 1010 also includes an extension tube 1015 extending therefrom for connection to an aspiration pump or other device capable of creating a suction force. Extension tube 1015 is in fluid communication with aspiration lumen 814. Extending from the proximal end of handle 1010 is a port 1026 through which a guidewire may be inserted. Within the handle, port 1026 is in connection with guidewire receiving tube 806. Port 1026 may be of a touhy-borst design.

Figure 22:
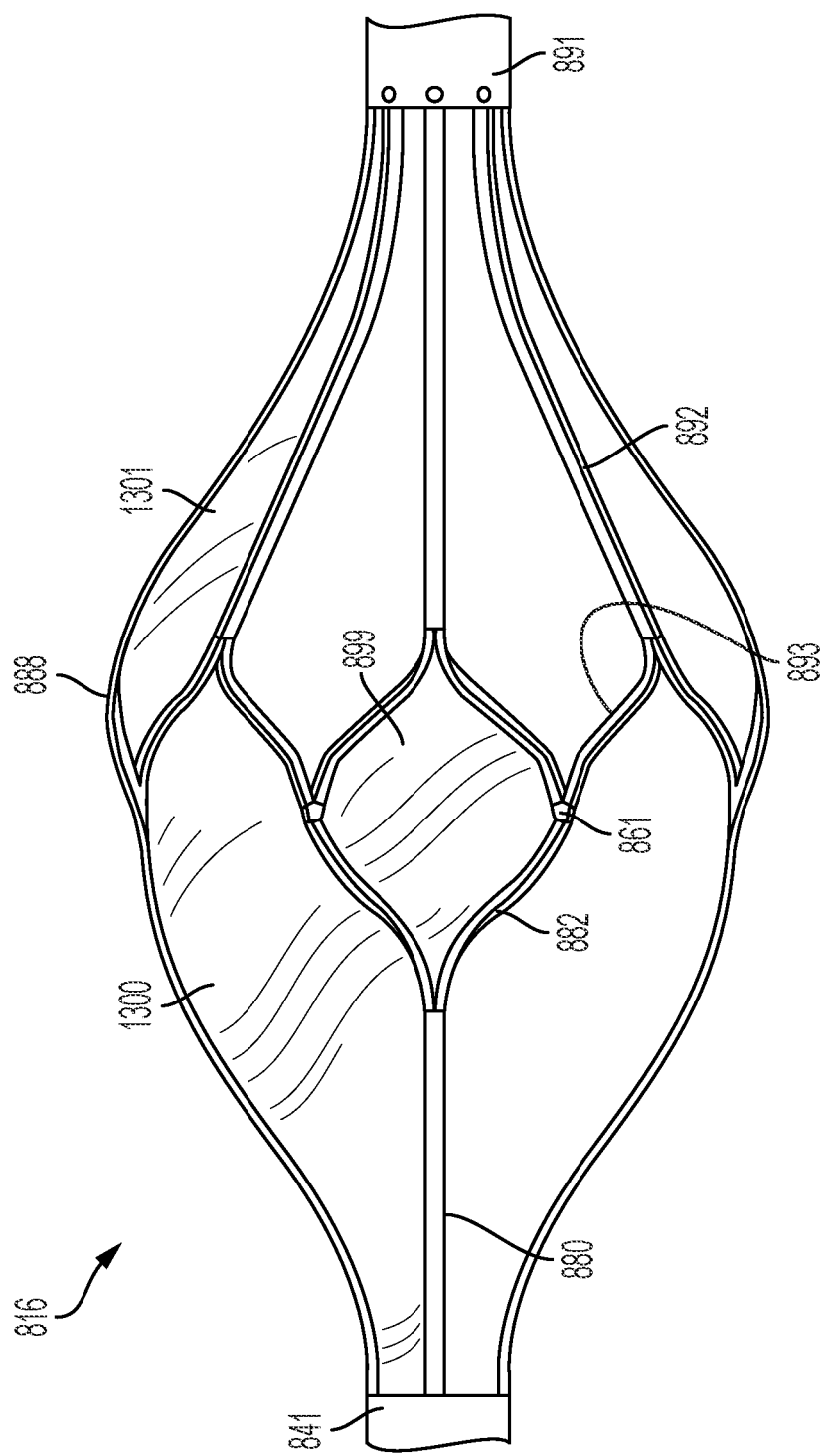
FIG. 22 depicts an enlarged, plan view of the distal expandable centering element frame.

The expandable centering cage 801 will now be described with reference to FIG. 19 and FIG. 22. Expandable centering cage 801 is comprised of frame 816, shown in FIG. 22. When expanded, frame 816 extends radially outward from proximal collar 841 to an expanded diameter 888 at substantially the center point of the expandable centering cage before converging radially inward toward distal collar 891. The expandable centering cage 801 comprises a collapsed position (not shown), an expanded position, and a fully expanded position. The expandable centering cage 801 is typically in the collapsed position (not shown) during insertion and removal from the body. The expandable centering cage 801 is in the fully expanded position when the expanded diameter 888 is equal to a maximum diameter of the expandable centering cage 801. The expanded diameter 888 ranges between the diameter of the centering cage 801 at the fully collapsed position (not shown) and the maximum diameter of the expandable centering cage 801. Frame 816 is comprised of proximal legs 880 which bifurcate into proximal diverging wire members 882. In one embodiment, the proximal legs 880 may be four in number, which bifurcate to create eight wire members 882. Frame 816 is also comprised of distal legs 892 extending proximally from distal collar 891. Distal legs 892 bifurcate to form distal wire members 893. In one embodiment, distal legs 892 may be six in number. Distal and proximal wire members 882 and 893 meet at junction 861 to form a series of diamond-shaped patterns 899 (shaded for clarity). Junction points 861 are positioned at or adjacent to the expanded diameter 888 of expandable centering cage 801 and are designed to provide multiple, spaced pressure contact points with the vessel wall. For example, in a frame 816 embodiment having four proximal legs 880, the number of junctions 861 contacting the vessel wall will be eight. A design with multiple junction points 861 provides more reliable and consistent contact between the centering cage's expanded diameter 888 and the vessel wall, thus facilitating removal of clot segments adhering to the vessel wall.

The frame construction described herein is also designed to facilitate the movement and retention of larger, fibrotic clot masses into the central part of the expandable centering cage 801. Because proximal legs 880 extend to or near the expanded diameter 888 before bifurcating into diverging wire members 882, larger areas of open space 1300 are created between the adjacent proximal legs 880 (area 1300 shaded for clarity only). These spaces allow larger en masse clot masses to be captured within the cage 801. In one embodiment a total of four 1300 open spaces are formed by the proximal legs 880. In contrast, the number of distal legs 892 may be six in number, creating much smaller open areas 1301 (also shaded) which are designed to retain clot volume within the expandable centering cage 801. This asymmetrical cage design thus provides for initial capture of large clot mass as well as retention of that clot mass once captured.

Figure 19:
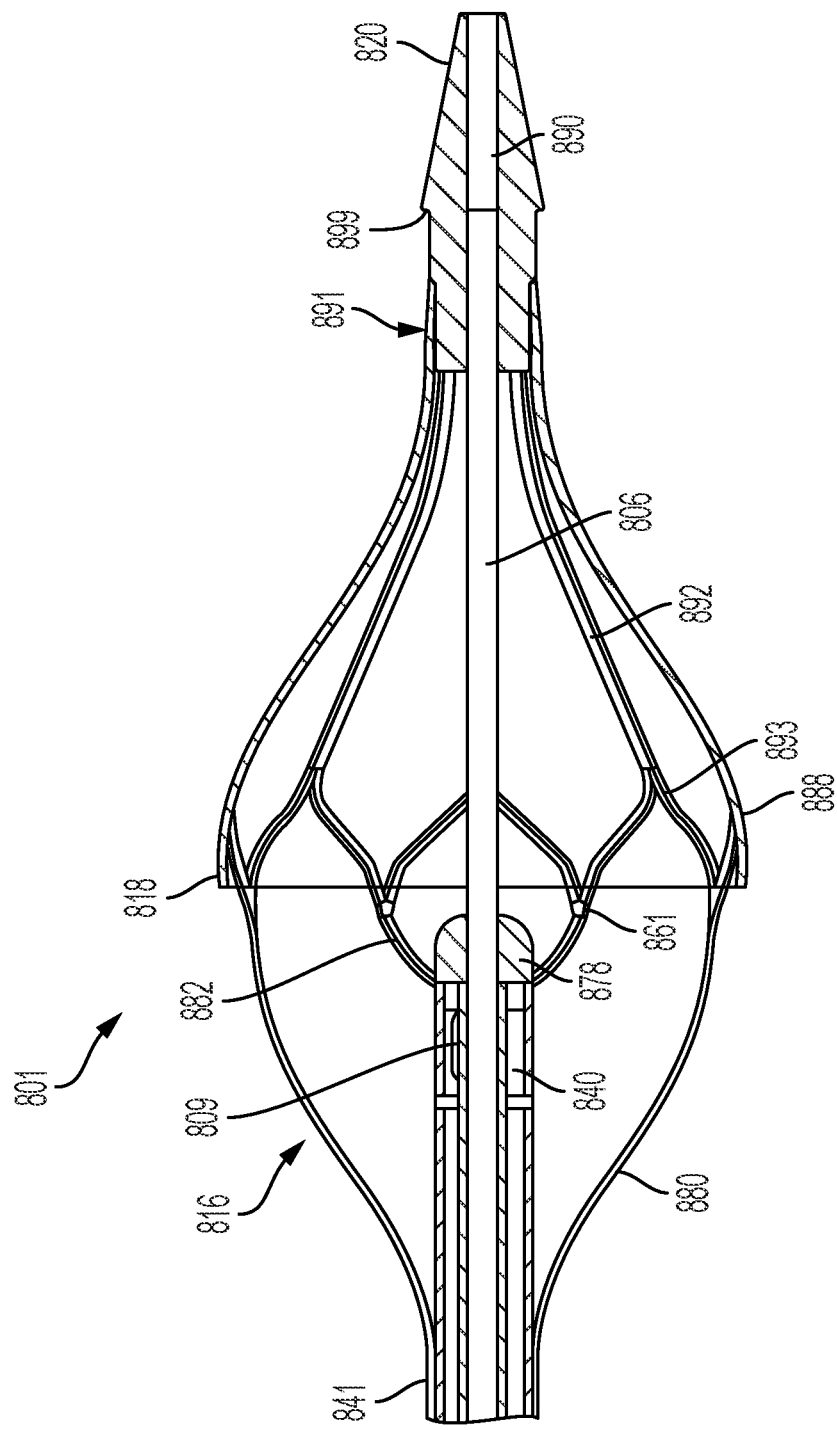
FIG. 19 is an enlarged cross-sectional view of the expandable centering element and rotating macerator.

As shown in FIG. 19, a cover film 818 may be positioned over the frame 816. Cover film 818 may be either permeable material, semi-permeable, or non-permeable material and formed using techniques known in the art including but not limited to heat molding one or more layers or a dipping process. Film cover 818 extends proximally from distal collar 891 to the center part of the frame 816 at or adjacent to expanded diameter 888. In use, the cover film 818 functions to capture and retain clot and clot debris prior to the material being drawn into the shearing window 809 of the macerator assembly 840. In one embodiment, cover film 818 may extend proximally beyond expanded diameter 888 to position the film in contact with vessel wall, thus ensuring debris does not migrate past the expandable centering cage 801 and the distal tip 820 of the device.

Still referring to FIG. 19, leading distal tip 820 is comprised of a proximal end, a distal end and a tip guidewire lumen 890 extending therethrough. As shown, the distal profile of tip 820 gradually tapers in a distal direction providing a smooth, atraumatic leading end of the device. The distal portion of guidewire receiving tube 806 is positioned within guidewire lumen 890 of tip 820. The proximal section of distal tip 820 includes a stepped-down outer diameter which is dimensioned to be positioned within the opening of distal collar 891 and permanently attached using techniques known in the art. Step up edge 899 of distal tip 820 is configured to abut against the distal end of the outer sleeve 802 (FIG. 15) when the sleeve is full advanced over the expandable centering cage 801. This design provides a smooth outer surface transition when the outer sleeve 802 is in place over the expandable centering cage 801, ensuring that during advancement of the device through the clot mass, as will be described in greater detail below, the device will not snag or catch on a venous valve, stenotic region or other variation in the profile of the vessel.

In an alternative embodiment (not shown), the expandable centering cage may configured to be "free-floating" and capable of automatically conforming to the vessel size without manual adjustment by a user. In the previously described embodiment, the proximal-most section of guidewire tube is glued or otherwise permanently connected to an internal location in the handle. By eliminating this connection point and allowing the guidewire tube limited longitudinal movement within the handle, frame, which is comprised of a shape memory metal, will automatically expand and contract based on the vessel size. Specifically, as vessel wall pressure is applied to the frame, the guidewire tube will longitudinally move within the handle in a distal direction. This movement will cause the distal tip of the device, which is connected to guidewire tube, to move in a corresponding distal direction, thus decreasing the diameter of the frame to match the vessel wall diameter. When within a larger diameter section of the vessel, frame will automatically expand until in contact with the vessel wall. Frame expansion corresponds with the guidewire tube proximal movement within the handle and a simultaneous proximal movement of the distal tip. This "floating" design of the expandable centering cage eliminates the need for the user to manipulate handle controls to set the desired centering cage diameter. Instead, the centering cage will automatically expand until in contact with the vessel wall. As the device is retracted or advanced through the vessel, the diameter of the centering cage will automatically adjust to the vessel diameter due to the shape memory characteristics of the centering cage material and the floating configuration of the guidewire tube. Thus, a single device may accommodate a wide range of vessels from the smaller, lower popliteal to the larger inferior vena cava and well as accommodating a wide range of diameters within a single treatment pathway.

Figure 20:
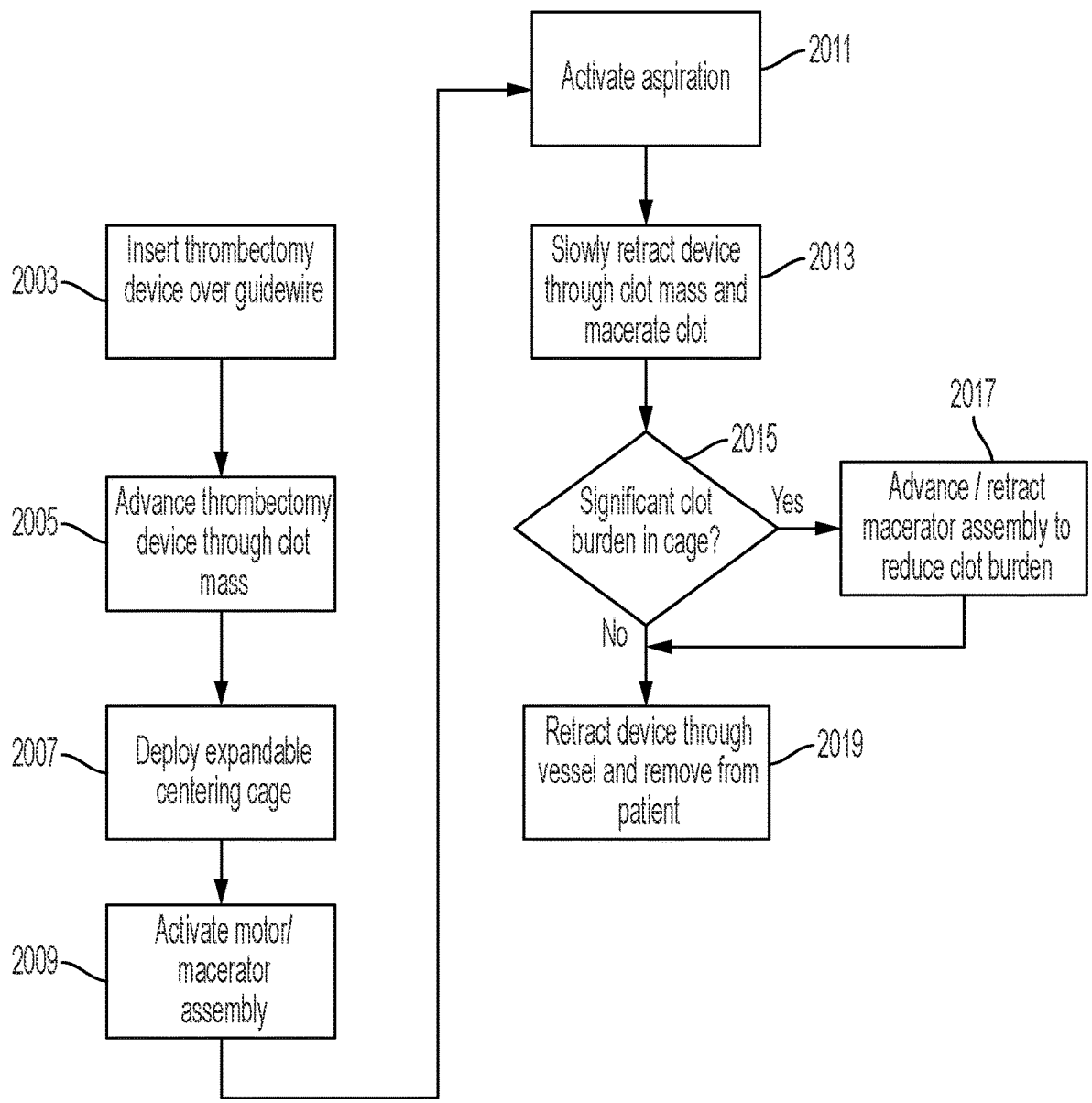
FIG. 20 illustrates one embodiment of the method of using the device of FIG. 15.

A method of using the clot removal device 800 of FIG. 15 will now be described with reference to FIG. 20. After the guidewire has been advanced through the clot mass, the centering cage 801 in a collapsed position is threaded over the guidewire 2003. The tapered leading distal end 820 of the device is used to advance the distal portion of the device through the clot mass 2005. Once positioned on the far side of the clot, the expandable centering cage 801 is deployed 2007. When deployed, the expandable centering cage aligns macerator assembly 840 of clot removal device 800 within the center of the vessel. In its deployed position, the expanded centering cage 801 may have a diameter in the range of 6 mm to 25 mm, although other expanded diameters are within the scope of this disclosure. The expandable centering cage may be manually adjusted to match the inner vessel wall diameter by manipulating the cage sizing element 1012 on handle 1010. If the "free-floating" design previously described is employed, the expandable centering cage 801 will automatically expand until it meets and conforms to the vessel wall.

Placement and expansion of the expandable member 801 centers the macerator assembly 840 within the vessel lumen. An advantage of centering the clot removal device 800 within the vessel lumen is that the macerator assembly 840 is not likely to engage, damage, rupture, or puncture the vessel wall as frame 816 provides a spacing barrier between the macerator and the vessel wall. After the expandable member 801 is expanded to the desired diameter, the drive shaft 805 may be activated using the motor, which causes activation of the macerator functionality 2009. A suction or vacuum apparatus is activated assist in the movement of clot material into the macerator 2011 and through the aspiration lumen into a waste receptacle.

With the macerator activated, the user slowly retracts device further into the clot mass 2013. In the event that the clot mass is adherent to the vessel wall, the user may manually rotate the device which causes the expandable centering cage 801 to rotate against the vessel wall. This gentle scraping technique may be used to dislodge any clot segments adhering to the vessel wall. The cover film 818 provides protection against abrasion, puncture or other damage to the wall during such rotation.

Figure 21A:
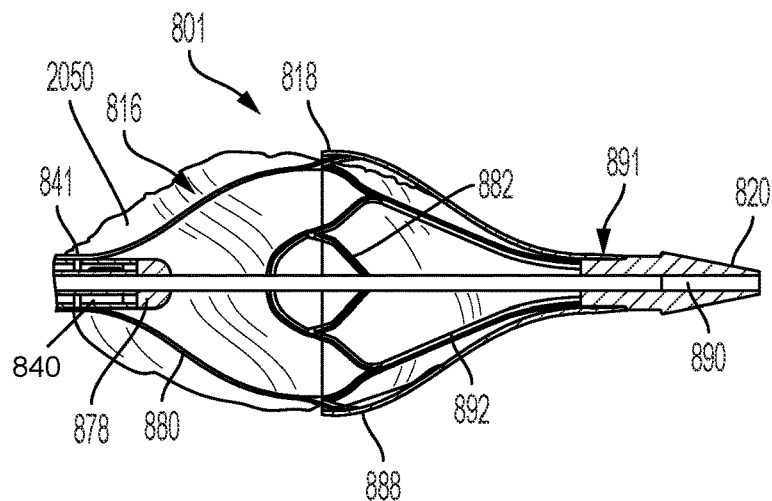
FIG. 21A-21C illustrates partial, cross-sectional views of a clot mass positioned within an expandable centering element with the shearing rotating macerator in a first position as shown in FIG. 21A, a second position as shown in FIG. 21B, and a third position as shown in FIG. 21C.
Figure 21B:
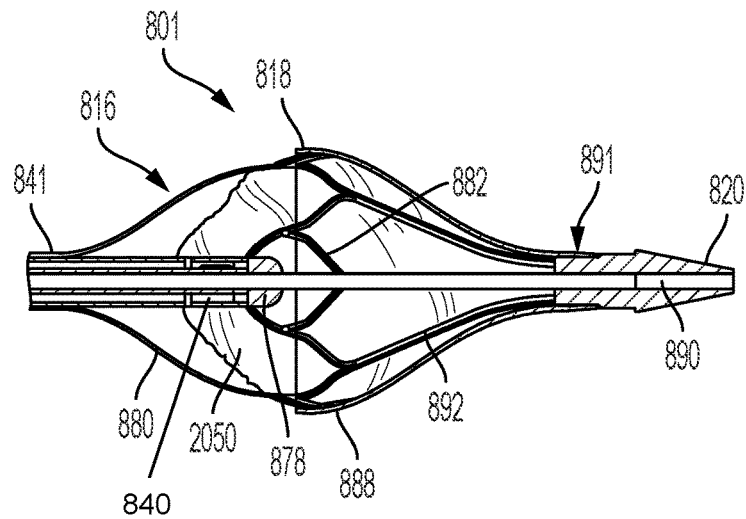
Figure 21C:
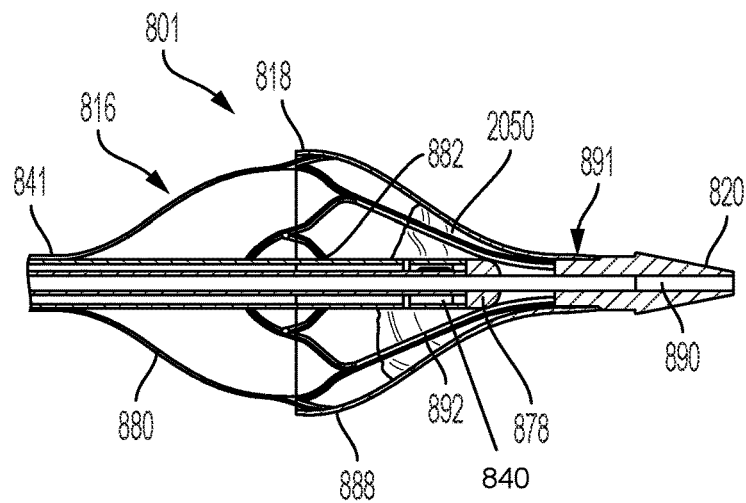

If the expandable centering cage 801 becomes overburdened with clot material 2015, the inner shaft of the macerator may be independently advanced and retracted 2017 while the centering cage remains stationary. Portions of the clot mass adjacent to macerator assembly 840 are successively drawn into shearing window 890 and macerated into small fragments. These fragments then are removed through the catheter elongated body 811 by the suction force being applied to the device. FIGS. 21A-21C illustrate how movement of the macerator assembly 840 independently of the expandable centering cage 801 aids in the disruption and removal of even large, fibrous clot masses. FIG. 21A depicts clot mass 2050 captured within the expandable centering cage 801 and extending from adjacent to the distal collar 891 proximally past the proximal collar 841. Macerator assembly 840 with leading distal cap 878 is shown positioned within the proximal portion of clot mass 2050. After the macerator and suction has been activated, the proximal portion of the clot mass 2050 will be sheared by the rotating movement of the drive shaft 805 within macerator 840, creating smaller clot masses which are aspirated through aspiration lumen 814 as previously described. As the proximal portion of the clot 2050 volume is reduced in this manner, the user may advance the macerator further distally into the remaining clot burden within the expandable centering cage 801, as shown in FIG. 21B. Specifically, the macerator positioning element 1013 on handle 1010 may be manipulated by the user to place of the macerator assembly 840 in a desired location relative to the centering cage 801. Again, the clot mass 2050 adjacent to the macerator assembly is drawn into the shearing windows 809 and sheared into smaller pieces. Continued suction draws more clot mass into the macerator to further reduce clot size. Any clot burden remaining trapped within the distal section of the expandable centering cage 801 can be captured, macerated and aspirated by further advancement of the macerator toward distal collar 891, as shown in FIG. 21C. Continued advancement and retraction of the macerator will result in the subsequent clearing of substantially all the clot burden present within the centering cage 801.

Once the clot mass within the expandable centering cage 801 has been macerated into smaller pieces and removed through aspiration or vacuum, the device is retracted further and the process is repeated on any additional clot segments present within the vessel. In summary, the device described herein can effectively remove even large, mature, attached clot masses through the combined actions of retraction and advancement, maceration, and rotation.

Retracting the device allows the expandable centering cage 801 to follow the natural contour of the vessel more easily than if the expandable centering cage was advanced through the vessel and may avoid the leading distal tip 820 from inadvertently becoming entangled a side branch vessel opening. If the device is be retracted through a vein, complications caused prolapse of venous valve leaflets is avoided. In addition, this approach also allows the pockets behind the valves, locations where clot commonly accumulates, to be cleared as the expanded centering cage contacts and moves the valves in the direction of blood flow. Specifically, the expandable centering cage 801 will push valve leaflets up against vessel wall as it is retracted, resulting in the dislodgement of clot located behind the leaflet. Retraction of the device also aids in the capture of any loose clot fragments and disengagement of any clot mass remaining attached to the vessel wall.

Referring back to FIG. 20, after the clot mass has been removed, the user retracts the clot removal device 800 through the vessel 2019 with the expandable centering cage in an expanded position. The expandable centering cage is then collapsed by advancing the slidable outer sleeve over the frame 816, after which the device is removed from the patient 2021.

In any of the above methods of removing undesirable material from a vessel, a temporary vessel occlusion device known in the art may used to further ensure that any dislodged, free-floating debris does not embolize.

Figure 23:
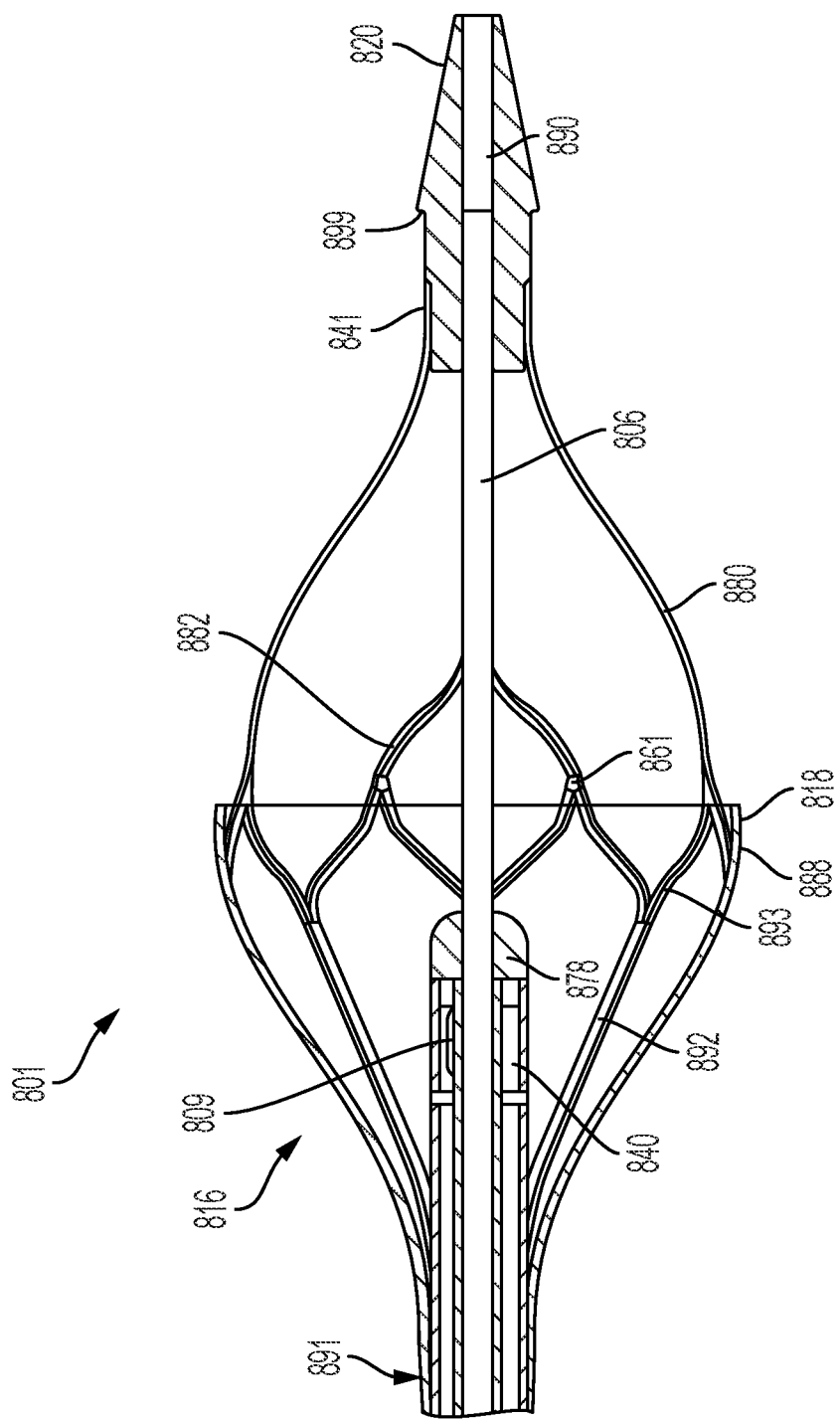
FIG. 23 illustrates another embodiment of the distal portion of the device shown from a plan view.

Referring now to FIG. 23, yet another embodiment of the clot removal device 800 and method of use is illustrated. FIG. 23 depicts the distal end section of the device 800 which is designed to retrieve and macerate clot or other material while being advanced through the vessel, rather than during retraction through the vessel. As shown, frame 816 of the expandable centering cage 801 is in a reversed position on the device (180 degrees offset from the previous embodiment). Also in contrast to the previous embodiment, membrane 818 is positioned over the proximal half of the centering cage 801 rather than the distal half. This design allows the clot segments to enter the expandable centering cage 801 through open spaces 1300 as device is advanced into the clot mass. The larger areas of open space 1300 allow en masse clot masses to be captured within the expandable centering cage 801 and positioned for maceration. The smaller open spaces 1301 between legs 892 and the proximal position of the membrane 818 ensure captured clot is retained within the expandable centering cage 801 for maceration by macerating element 878.

In use, the device is inserted in the popliteal or other lower leg vein and advanced over a guidewire toward the clot mass. As the device is advanced further into the target clot mass, portions of the clot will enter the expandable centering cage 801 for maceration. As with the previous embodiments, the macerator assembly 840 may be advanced and retracted along the guidewire tube while the centering cage 801 remains stationary to sequentially fragment and aspire the entire clot burden within the centering cage. After macerating clot segments present within expandable centering cage 801, the device may be advanced further into the remaining clot body where additional clot segments are macerated and removed through aspiration lumen 814. Any the clot mass adhering to the vessel wall may be removed by manually rotating the device in either a clock-wise or counter clock-wise direction such that the expandable centering cage 801 at its expanded diameter 888 scrapes and dislodges any clot segments still adhering to the vessel wall. Once the entire clot burden has been removed from the vessel, the expandable centering cage is collapsed as previously described and the device is removed from the patient. There are several key advantages of the device and method of FIG. 25, including simplified access and eliminating the need to maneuver the device through and past the clot prior to activating aspiration and maceration.

In summary, the design described herein combines disengagement of the clot from the vessel wall, sequential maceration of the entire clot burden and aspiration for removal of clot fragments to remove even dense, fibrous clot masses which cannot be removed en masse without the use of lytics. Thus, in one advantage of this embodiment, the macerator 840 may be positioned at multiple locations within the captured clot burden, to ensure complete maceration and removal of the entire clot burden.

The invention claimed is:

1. A system for removing undesirable material from a body, the system comprising:
    an outer shaft, an intermediate shaft, and an inner shaft;
    wherein the intermediate shaft is configured to be coaxially inserted within a lumen of the outer shaft and coaxially over the inner shaft, and wherein the intermediate shaft is uncoupled at a distal end from the outer shaft and the inner shaft, and is independently translatable and rotatable relative to the outer shaft and the inner shaft;
    a helical macerator member at the distal end of the intermediate shaft;
    an aspiration source configured to be operatively fluidly coupled to the lumen of the outer shaft and generate a suction force within the outer shaft to draw undesirable material into the outer shaft; and
    wherein the helical macerator member is configured to operatively engage the undesirable material within the outer shaft, and wherein the helical macerator member is configured to disrupt the undesirable material within the outer shaft upon rotation of the intermediate shaft.

2. The system of claim 1, wherein the suction force within the outer shaft is configured to suction the disrupted undesirable material.

3. The system of claim 1, wherein the outer shaft includes a reinforcing element having at least one wire member.

4. The system of claim 3, wherein the outer shaft includes an expandable element.

5. The system of claim 4, wherein the expandable element is positioned at a distal end of the outer shaft.

6. The system of claim 4, wherein the expandable element comprises a cover composed of a permeable material or non-permeable material.

7. The system of claim 3, wherein the at least one wire member includes a plurality of wires having a proximal wire section and a distal wire section, and wherein a number of interconnection locations of the proximal wire section is greater than a number of interconnection locations of the distal wire section.

8. The system of claim 3, wherein the at least one wire member includes shape memory material, nitinol, stainless steel or plastic.

9. The system of claim 1, wherein the intermediate shaft is capable of manual rotation.

10. The system of claim 1, wherein the helical macerator member is configured to macerate the undesirable material within an annular space defined between the helical macerator member and the outer shaft.

11. The system of claim 1, wherein the intermediate shaft is configured to be manually rotated to disrupt the undesirable material within the outer shaft.

12. A system for removing undesirable material from a body, the system comprising:
- an outer shaft, an intermediate shaft, and an inner shaft, the outer shaft being an elongate outer shaft and the inner shaft being an elongate inner shaft;
- wherein the intermediate shaft is configured to be coaxially inserted within a lumen of the outer shaft and coaxially over the inner shaft, and wherein the intermediate shaft is uncoupled at a distal end from the outer shaft and the inner shaft, and is independently translatable and rotatable relative to the outer shaft and the inner shaft
- a helical macerator member at the distal end of the intermediate shaft;
- an aspiration source configured to be operatively fluidly coupled to the lumen of the outer shaft and generate a suction force within the outer shaft to draw undesirable material into the outer shaft; and
- wherein the helical macerator member is configured to operatively engage the undesirable material within the outer shaft, and wherein the helical macerator member is configured to disrupt the undesirable material within the outer shaft upon rotation of the intermediate shaft.

13. The system of claim 12, wherein the suction force within the outer shaft is configured to suction the disrupted undesirable material.

14. The system of claim 12, wherein the reinforcing element includes at least one wire member.

15. The system of claim 14, wherein the outer shaft includes an expandable element.

16. The system of claim 15, wherein the expandable element is positioned at a distal end of the outer shaft.

17. The system of claim 15, wherein the expandable element comprises a cover composed of a permeable material or non-permeable material.

18. The system of claim 14, wherein the at least one wire member includes a plurality of wires having a proximal wire section and a distal wire section, and wherein a number of interconnection locations of the proximal wire section is greater than a number of interconnection locations of the distal wire section.

19. The system of claim 14, wherein the at least one wire member includes shape memory material, nitinol, stainless steel or plastic.

20. The system of claim 12, wherein the intermediate shaft is capable of manual rotation.

* * * * *